United States Patent [19]

Nebel et al.

[11] Patent Number: 6,083,881
[45] Date of Patent: Jul. 4, 2000

[54] PYRAZOLE DERIVATIVES AS HERBICIDES

[75] Inventors: Kurt Nebel, Hochwald; Hans-Georg Brunner, Lausen, both of Switzerland; Georg Pissiotas, Lörrach, Germany

[73] Assignee: Novartis Corporation, Summit, N.J.

[21] Appl. No.: 08/765,388

[22] PCT Filed: Jun. 22, 1995

[86] PCT No.: PCT/EP95/02435

§ 371 Date: Jan. 6, 1997

§ 102(e) Date: Jan. 6, 1997

[87] PCT Pub. No.: WO96/01254

PCT Pub. Date: Jan. 18, 1996

[30] Foreign Application Priority Data

Jul. 5, 1994 [CH] Switzerland .................. 2151/94

[51] Int. Cl.[7] .................. A01N 43/56; C07D 231/16; C07D 405/10
[52] U.S. Cl. ................ 504/280; 548/365.7; 548/375.1
[58] Field of Search .............. 548/375.1, 365.7; 504/280

[56] References Cited

U.S. PATENT DOCUMENTS 4,621,084  11/1986  Takaya et al. .

FOREIGN PATENT DOCUMENTS

| | | |
|---|---|---|
| 0112623 | 7/1984 | European Pat. Off. . |
| 0120589 | 10/1984 | European Pat. Off. . |
| 0361114 | 4/1990 | European Pat. Off. . |
| 0443059 | 8/1991 | European Pat. Off. . |
| 0210265 | 6/1984 | Germany . |
| 2300173 | 12/1990 | Japan . |
| 3093774 | 4/1991 | Japan . |
| 6065239 | 3/1994 | Japan . |
| 9206962 | 4/1992 | WIPO . |
| 9315074 | 8/1993 | WIPO . |
| 9502590 | 1/1995 | WIPO . |

OTHER PUBLICATIONS

Chemical Abstract, vol. 115, No. 9, 115:92260d (1991).
Chemcial Abstract, vol. 114, No. 17, 114:1642266 (1991).
Chemical Abstract, vol. 121, No. 7, 121:76197g (1994).
Chemical Abstract, vol. 112, No. 19, 112:178770v (1990).
Pharmazie 44(8), pp. 535–539 (1989).
Chemical Abstract, vol. 112, No. 3, 112:21206t (1990).
Chemical Abstracts, Chemical Substances, 12th Collective Index, vol. 107–115, 1987–1991, pp. 78343CS & 78428CS: RN [124344–96–3] & [124344–99–6].
Carbohydrate Research, No. 189, pp. 349–358 (1989).
Chemical Abstract, vol. 102, No. 25, 102:220868d (1985).
Chemical Abstracts, Chemical Substances, 11th Collective Index, vol. 96–105, 1982–1986, pp. 58069CS, 58070CS & 58071CS: RN [93618–33–8], [93660–30–1], [93618–36–1], [93618–54–3], [93618–34–9], [93618–52–1] and [93618–4–6].
Chemical Abstract, vol. 69, No. 15, 69:59155g (1968).
Khim.–Farm. Zh., 2(1), 16–22 (1968).
Chemical Abstract vol. 102, No. 9, 102:78877k (1985).
Chemical Abstracts, Chemical Substances, 11th Collective Index, vol. 96–105, 1982–1986, pp. 11970CS: RN [90348–03–1] and [94662–43–8].
Chemical Abstact, vol. 101, No. 7, 101:55016v (1984).
Chemical Abstracts, Chemical Substances, 11th Collective Index, vol. 96–105, 1982–1986, pp. 12117CS & 12124CS: RN [91119–98–1], [91119–97–0], [91119–94–7], [91119–93–6], [91119–95–8] [26518–71–8].
Indian Journal of Chemistry, Section B, vol. 22B(12), pp. 1236–1242 (1983).
Organic Reactions, vol. 18, 1 (1970).
Organic Synthesis vol. 49, pp. 81–85 (1969).
Comprehensive Organic Transformations, Editor R.C. Larock, p. 685, VCH 1989.
Tetrahedron, vol. 48, No. 42, pp. 9233–9236 (1992).
J. Chem. Soc. 1954, 1297.
"Vogel's Textbook of Practical Organic Chemistry", Longman 1989, pp. 938 et seq., 1006 et. seq. and 1084 et seq.
"Advanced Organic Chemistry", Editor J. March, McGraw–Hill Book Company, New York, 1985, pp. 816 et seq., 932 et seq., & 1057 et seq.
"Organikum" Editor J. A. Barth, Leipzig, 1993, pp. 425 et seq. and 439 et seq.
Arch. Pharm. 264, pp. 337–355 (1926).
Liebigs Annalen 437, pp. 297–308 (1924).
"Methodicum Chimicum", vol. 6, Georg Thieme Verlag, Stuttgart, p. 768 et seq. (1974).
"Methoden der Organischen Chemie" (Methods of Organic Chemistry) (Houben–Weyl), vol. E5, Georg Thieme Verlag Stuttgart, p. 1242 et seq. (1985).
"Methoden der Organischen Chemie" (Methods of Organic Chemistry)(Houben–Weyl), vol. E8b, Georg Thieme Verlag Stuttgart, p. 399 et seq. (1994).
"Pyrzaoles, Pyrazolines, Pyrazolidines, Indazoles and Condensed Rings", Editor R.H. Wiley, Interscience Publishers, New York, 1967, p. 1 et seq.
Tetrahedron Lett. 51, pp. 4907–4910 (1979).

*Primary Examiner*—Robert W. Ramsuer
*Attorney, Agent, or Firm*—William A. Teoli, Jr.

[57] ABSTRACT

Compounds of formula (I)

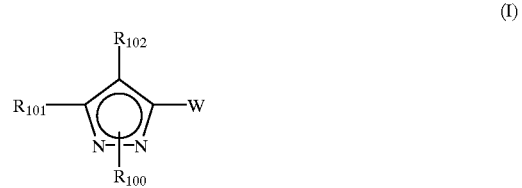

in which the substituents W, $R_{100}$, $R_{101}$ and $R_{102}$ are as defined 1; and the pyrazole N-oxides, salts, complexes and stereoisomer of the compounds of (I) have good pre- and post-emergence selective herbicidal properties. The preparation compounds and their use as herbicidal active compounds are described.

9 Claims, No Drawings

PYRAZOLE DERIVATIVES AS HERBICIDES

The present invention relates to novel herbicidally active pyrazole derivatives, processes for their preparation, compositions which comprise these compounds and their use for control of weeds, in particular in crops of useful plants, or for inhibiting plant growth.

Pyrazole compounds having a herbicidal action are known and are described, for example, in JP-A-03 093 774, JP-A-02 300 173 and JP-A-03 163 063.

Novel pyrazole derivatives having herbicidal and growth-inhibiting properties have now been found.

The present invention thus relates to compounds of the formula I

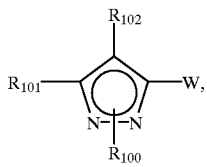

(I)

in which $R_{100}$ is hydrogen, $C_1$–$C_6$alkyl, $C_3$–$C_8$cycloalkyl, $C_3$–$C_8$cycloalkyl-$C_1$–$C_6$alkyl, $C_3$–$C_6$alkenyl, $C_4$–$C_8$cycloalkenyl, $C_4$–$C_8$cycloalkenyl-$C_1$–$C_6$alkyl, $C_3$–$C_6$alkynyl, phenyl, phenyl-$C_1$–$C_6$alkyl or cyano, where the groups listed for $R_{100}$, with the exception of hydrogen and cyano, can be substituted by halogen, $C_1$–$C_6$alkyl, $C_1$–$C_6$halogenoalkyl, cyano, nitro, —$COR_3$, —$X_3R_{04}$, —$COR_8$, —$NR_{56}R_{57}$ or —$NR_{56}OR_{57}$, in which $R_{56}$ and $R_{57}$ independently of one another are hydrogen, $C_1$–$C_8$alkyl, $C_1$–$C_8$halogenoalkyl, $C_3$–$C_8$alkenyl, $C_3$–$C_8$halogenoalkenyl, $C_3$–$C_8$alkynyl, $C_1$–$C_4$alkoxy-$C_1$–$C_8$alkyl, cyano-$C_1$–$C_8$alkyl, $C_1$–$C_8$alkoxycarbonyl-$C_1$–$C_4$alkyl, $C_3$–$C_7$cycloalkyl, $C_3$–$C_7$cycloalkyl-$C_1$–$C_4$alkyl, benzyl, $C_1$–$C_4$alkyl which is substituted by -N-morpholino, -N-thiomorpholino or -N-piperazino, di-$C_1$–$C_4$alkylamino-$C_1$–$C_4$alkyl, $C_1$–$C_4$alkylaminocarbonyl-$C_1$–$C_4$alkyl, di-$C_1$–$C_4$alkylaminocarbonyl-$C_1$–$C_4$alkyl, $C_1$–$C_4$alkoxycarbonyl or $C_1$–$C_4$alkylcarbonyl; or $R_{56}$ and $R_{57}$ together complete a 5-, 6- or 7-membered carbo- or heterocyclic ring; $R_3$ is halogen, —$X_4$—$R_5$, amino, $C_1$–$C_4$alkylamino, di-$C_1$–$C_4$alkylamino, $C_2$–$C_4$-halogenoalkylamino, di-$C_2$–$C_4$halogenoalkylamino, $C_1$–$C_4$alkoxy-$C_2$–$C_4$alkylamino, di-$C_1$–$C_4$alkoxy-$C_2$–$C_4$alkylamino, $C_3$- or $C_4$alkenylamino, diallylamino, -N-pyrrolidino, -N-piperidino, -N-morpholino, -N-thiomorpholino, -N-piperazino or —O—N=C($CH_3$)—$CH_3$; in which $X_4$ is oxygen or sulfur, and $R_5$ is hydrogen, $C_1$–$C_{10}$alkyl, $C_1$–$C_4$alkoxy-$C_1$–$C_4$alkyl, $C_2$–$C_8$halogenoalkyl, $C_1$–$C_8$-alkylthio-$C_1$–$C_4$alkyl, di-$C_1$–$C_4$alkylamino-$C_1$–$C_4$alkyl, cyano-$C_1$–$C_8$alkyl, $C_3$–$C_8$alkenyl, $C_3$–$C_8$halogenoalkenyl, $C_3$–$C_8$alkynyl, $C_3$–$C_7$cycloalkyl, oxetan-3-yl, $C_3$–$C_7$-cycloalkyl-$C_1$–$C_4$alkyl, halogeno-$C_3$–$C_7$cycloalkyl or benzyl, which is unsubstituted or substituted on the phenyl ring up to three times in an identical or different manner by halogen, $C_1$–$C_4$alkyl, $C_1$–$C_4$halogenoalkyl, $C_1$–$C_4$halogenoalkoxy or $C_1$–$C_4$alkoxy; alkali metal, alkaline earth metal or ammonium ions; or $C_1$–$C_6$alkyl-$COOR_7$, in which $R_7$ is hydrogen, $C_1$–$C_6$alkyl, $C_3$–$C_8$alkenyl, $C_3$–$C_8$alkynyl, $C_1$–$C_8$alkoxy-$C_2$–$C_8$alkyl, $C_1$–$C_8$alkylthio-$C_1$–$C_8$alkyl or $C_3$–$C_7$cycloalkyl;

$R_{04}$ is hydrogen, $C_1$–$C_6$alkyl, $C_1$–$C_6$cyanoalkyl, $C_2$–$C_7$alkoxycarbonyl or oxetan-3-yl;

$X_3$ is oxygen or sulfur, $R_8$ is hydrogen or $C_1$–$C_4$alkyl;

$R_{101}$ is cyano,

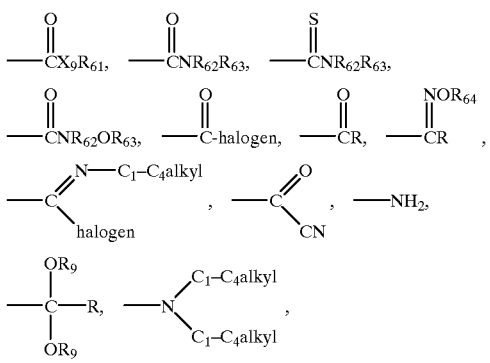

-nitro, —NH—CHO or —NC, in which $X_9$ is oxygen or sulfur;

$R_{61}$ is defined as $R_5$;

$R_{62}$ and $R_{63}$ independently of one another are defined as $R_{56}$;

halogen is fluorine, chlorine or bromine;

R is hydrogen, $C_1$–$C_4$alkyl or trifluoromethyl;

$R_{64}$ is hydrogen, $C_1$–$C_{10}$alkyl, $C_1$–$C_4$alkoxy-$C_1$–$C_4$alkyl, $C_1$–$C_4$alkylthio-$C_1$–$C_4$alkyl, di-$C_1$–$C_4$alkylamino-$C_1$–$C_4$alkyl, $C_1$–$C_8$halogenoalkyl, $C_2$–$C_8$alkenyl, $C_2$–$C_8$halogenoalkenyl, $C_3$–$C_8$alkynyl, $C_3$–$C_7$cycloalkyl, oxetan-3-yl, halogeno-$C_3$–$C_7$-cycloalkyl, $C_1$–$C_8$alkylcarbonyl, allylcarbonyl, $C_3$–$C_7$cycloalkylcarbonyl, benzoyl, which is unsubstituted or substituted on the phenyl ring up to three times in an identical or different manner by halogen, $C_1$–$C_4$alkyl, $C_1$–$C_4$halogenoalkyl, $C_1$–$C_4$halogenoalkoxy or $C_1$–$C_4$-alkoxy; $C_1$–$C_4$alkyl substituted by cyano, nitro, carboxyl, $C_1$–$C_8$alkyl-thio-$C_1$–$C_8$alkoxycarbonyl, phenyl, halogenophenyl, $C_1$–$C_4$alkylphenyl, $C_1$–$C_4$alkoxy-phenyl, $C_1$–$C_4$halogenoalkylphenyl, $C_1$–$C_4$halogenoalkoxyphenyl, $C_1$–$C_6$alkoxycarbonyl, $C_1$–$C_4$alkoxy-$C_1$–$C_8$alkoxycarbonyl, $C_3$–$C_8$alkenyloxycarbonyl, $C_3$–$C_8$alkynyloxycarbonyl, $C_1$–$C_8$alkylthiocarbonyl, $C_3$–$C_8$alkenylthiocarbonyl, $C_3$–$C_8$alkynylthiocarbonyl, carbamoyl, $C_1$–$C_4$alkylaminocarbonyl, di-$C_1$–$C_4$alkylaminocarbonyl; phenylaminocarbonyl, which is unsubstituted or substituted on the phenyl up to three times in an identical or different manner by halogen, $C_1$–$C_4$alkyl, $C_1$–$C_4$halogenoalkyl, $C_1$–$C_4$halogenoalkoxy or $C_1$–$C_4$-alkoxy or once by cyano or nitro; dioxolan-2-yl, which is unsubstituted or substituted by one or two $C_1$–$C_4$alkyl radicals; or dioxanyl, which is unsubstituted or substituted by one or two $C_1$–$C_4$alkyl radicals; and $R_9$ and $R_{10}$ independently of one another are each $C_1$–$C_4$alkyl, $C_2$–$C_4$halogenoalkyl or $C_2$–$C_8$alkoxyalkyl; or $R_9$ and $R_{10}$ together are an ethylene-, propylene- or a cyclohexane-1,2-diyl bridge, where these groups can be either unsubstituted or substituted by one or two radicals from the group consisting of $C_1$–$C_4$alkyl, $C_1$–$C_4$halogenoalkyl or $C_1$–$C_4$hydroxyalkyl; $R_{102}$ is hydrogen, halogen, $C_1$–$C_4$alkyl, $C_3$–$C_6$cycloalkyl, $C_1$–$C_4$halogenoalkyl, cyano, $C_2$–$C_4$-alkenyl, $C_2$–$C_4$halogenoalkenyl, $C_2$–$C_4$alkynyl, $C_2$–$C_4$halogenoalkynyl, nitro, amino,

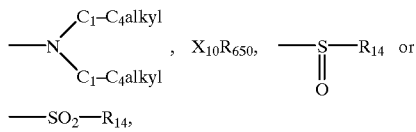

—$SO_2$—$R_{14}$, in which $X_{10}$ is oxygen or sulfur;

$R_{650}$ is hydrogen, $C_1$–$C_6$alkyl or $C_1$–$C_6$halogenoalkyl; and $R_{14}$ is $C_1$–$C_6$alkyl; $C_1$–$C_6$halogenoalkyl, $C_1$–$C_6$alkylamino or di-$C_1$–$C_4$-alkylamino; and W is an aromatic system, where phenyl and 2,4-dichlorophenyl are excluded, and the pyrazole N-oxides, salts, complexes and stereoisomers of the compounds of the formula I.

In the above definitions, halogen or halogeno—unless stated otherwise—is to be understood as meaning fluorine, chlorine, bromine and iodine, preferably fluorine, chlorine and bromine.

The alkyl, alkenyl and alkynyl groups can be straight-chain or branched, this also applying to the alkyl, alkenyl and alkynyl moiety of the halogenoalkyl, halogenoalkenyl, halogenoalkynyl, halogenoalkylphenyl, halogenoalkoxyphenyl, alkoxyalkyl, alkylsulfonyl, cycloalkyl-alkyl, cycloalkenyl-alkyl, phenyl-alky, alkylphenyl, phenylalkenyl, phenylalkynyl, alkylamino, dialkylamino, dialkylamino-alkyl, alkylaminocarbonyl-alkyl, halogenoalkylamino, dihalogenoalkylamino, alkoxyalkylamino, cyanoalkyl, hydroxyalkyl, carboxyalkyl, alkylthio-alkyl, alkylthio-alkoxycarbonyl, alkylthiocarbonyl-alkyl, alkenylthiocarbonyl, alkynylthiocarbonyl, halogenoalkoxycarbonyl-alkyl, alkenyloxy-alkyl, alkylcarbonyl, alkenyloxycarbonyl, alkynyloxycarbonyl, alkoxycarbonyl-alkyl and heterocyclyl-alkyl groups.

Examples of alkyl groups are methyl, ethyl, n-propyl, iso-propyl, n-butyl, iso-butyl, sec-butyl, tert-butyl and the various isomeric pentyl, hexyl, heptyl, octyl, nonyl and decyl radicals, preferably alkyl groups having 1 to 4 carbon atoms.

Examples of alkenyl are vinyl, allyl, methallyl, 1-methylvinyl, but-2-en-1-yl, pentenyl, 2-hexenyl, 3-heptenyl and 4-octenyl, preferably alkenyl radicals having a chain length of 3 to 5 carbon atoms.

Examples of alkynyls are ethynyl, propargyl, 1-methylpropargyl, 3-butynyl, but-2-yn-1-yl, 2-methylbutyn-2-yl, but-3-yn-2-yl, 1-pentynyl, pent-4-yn-1-yl or 2-hexynyl, preferably alkynyl radicals having a chain length of 2 to 4 carbon atoms.

Halogenoalkyl groups are alkyl groups which are mono- or polysubstituted, in particular mono- to trisubstituted, by halogen, halogen being specifically iodine, and in particular fluorine, chlorine and bromine, for example fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl.

Cyanoalkyl is, for example, cyanomethyl, cyanoethyl, cyanoeth-1-yl and cyanopropyl.

Hydroxyalkyl is, for example, hydroxymethyl, 2-hydroxyethyl and 3-hydroxypropyl.

Carboxyalkyl is, for example, carboxymethyl, carboxyethyl, carboxyeth-1-yl and carboxypropyl.

Alkoxyalkyl is, for example, methoxymethyl, ethoxymethyl, propoxymethyl, methoxyethyl, ethoxyethyl, propoxyethyl, butoxyethyl, methoxypropyl, ethoxypropyl or propoxypropyl.

Halogenoalkenyl groups are alkenyl groups which are mono- or polysubstituted by halogen, halogen being bromine, iodine and, in particular, fluorine and chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluoro-but-2-en-1-yl. Preferred $C_2$–$C_{10}$alkenyl radicals which are mono-, di- or trisubstituted by halogen are those which have a chain length of 3 to 5 carbon atoms.

Halogenoalkynyl groups are, for example, alkynyl groups which are mono- or polysubstituted by halogen, halogen being bromine, iodine and, in particular, fluorine and chlorine, for example 3-fluoropropynyl, 3-chloropropynyl, 3-bromopropynyl, 3,3,3-trifluoropropynyl and 4,4,4-trifluoro-but-2-yn-1-yl. Preferred alkynyl radicals which are mono- or polysubstituted by halogen are those which have a chain length of 3 and 4 carbon atoms.

Alkoxy is, for example, methoxy, ethoxy, n-propoxy, iso-propoxy, n-butoxy, iso-butoxy, sec-butoxy and tert-butoxy.

Alkoxycarbonyl is, for example, methoxycarbonyl, ethoxycarbonyl, n-propoxycarbonyl, iso-propoxycarbonyl and n-butoxycarbonyl, preferably methoxycarbonyl and ethoxycarbonyl.

Alkenyloxycarbonyl is, for example, allyloxycarbonyl, methallyloxycarbonyl, but-2-en-1-yl-oxycarbonyl, pentenyloxycarbonyl, 2-hexenyloxycarbonyl and 3-heptenyloxycarbonyl.

Alkynyloxycarbonyl is, for example, propargyloxycarbonyl, 3-butynyloxycarbonyl, but-2-yn-1-yl-oxycarbonyl and 2-methylbutyn-2-yl-oxycarbonyl.

Alkylamino is, for example, methylamino, ethylamino and the isomeric propyl- and butylamino.

Dialkylamino is, for example, dimethylamino, diethylamino and the isomeric dipropyl- and dibutylamino.

Alkenylamino is, for example, allylamino, methallylamino and but-2-en-1-yl-amino.

Cycloalkyl radicals which are substituents are, for example, cyclopropyl, cyclobutyl, cyclopentyl, cyclohexyl, cycloheptyl or cyclooctyl.

Cycloalkenyl is, for example, cyclobutenyl, cyclopentenyl, cyclohexenyl, cycloheptenyl and cyclooctenyl.

Halogenocycloalkyl radicals which are substituents are, for example, mono-, di- or up to perhalogenated cycloalkyl radicals, for example fluorocyclopropyl, 2,2-dichlorocyclopropyl, pentachlorocyclohexyl or perfluorocyclopentyl.

Alkoxyalkoxyalkyl is, for example, methoxymethoxymethyl, ethoxymethoxyethyl, ethoxyethoxymethyl, propoxymethoxymethyl, propoxyethoxyethyl, propoxypropoxymethyl, butoxyethoxyethyl and butoxybutoxyethyl.

Halogenoalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy.

Halogenoalkylamino is, for example, chloroethylamino, trifluoroethylamino and 3-chloropropylamino.

Dihalogenoalkylamino is, for example, di(chloroethyl) amino.

Alkylthioalkyl is, for example, methylthioethyl, ethylthioethyl, methylthiopropyl and ethylthiopropyl.

Alkenylthiocarbonyl is, for example, allylthiocarbonyl, methallylthiocarbonyl, but-2-en-1-yl-thiocarbonyl, pentenylthiocarbonyl and 2-hexenylthiocarbonyl.

Alkynylthiocarbonyl is, for example, propargylthiocarbonyl, 1-methylpropargylthiocarbonyl and but-2-yn-1-yl-thiocarbonyl.

Phenyl as part of a substituent such as phenylalkyl, phenylalkenyl or phenylalkynyl is unsubstituted or substituted. The substituents can be in the ortho-, meta- or para-position. Preferred substituent positions are the ortho- and para-position relative to the ring linkage site. Substituents are, for example, $C_1$–$C_4$alkyl, halogen, $C_1$–$C_4$halogenoalkyl, cyano, nitro, hydroxyl, $C_1$–$C_4$alkoxy, $C_1$–$C_4$halogenoalkoxy, amino, $C_1$–$C_4$alkylamino, di-$C_1$–$C_4$alkylamino, carboxyl, $C_1$–$C_4$alkoxycarbonyl, carbamoyl, $C_1$–$C_4$alkylaminocarbonyl or di-$C_1$–$C_4$alkylaminocarbonyl.

5- or 6 membered heterocyclyl groups are either unsaturated or completely or partly saturated heterocyclic groups, for example pyrrolidino, piperidino, tetrahydrofurano, tetrahydropyrano, morpholino, thiomorpholino and piperazino, and in particular aromatic heterocyclic rings, for example 2-, 3- or 4-pyridyl, pyrimidyl, pyrazinyl, pyridazinyl, pyrazolyl, imidazolyl, triazolyl, pyrrolyl, thienyl, furyl, oxazolyl, thiazolyl and isoxazolyl. These heterocyclic groups can in turn be substituted; substituents are, for example, $C_1$–$C_4$alkyl, halogen, $C_1$–$C_4$halogenoalkyl, cyano, nitro, hydroxyl, $C_1$–$C_4$alkoxy, $C_1$–$C_4$halogenoalkoxy, amino, $C_1$–$C_4$alkylamino, di-$C_1$–$C_4$-alkylamino, carboxyl, $C_1$–$C_4$alkoxycarbonyl, carbamoyl, $C_1$–$C_4$alkylaminocarbonyl or di-$C_1$–$C_4$alkylaminocarbonyl.

Examples of the 3- to 6-membered carbocyclic and heterocyclic rings are cyclopropano, cyclobutano, cyclopentano, cyclohexano, oxetano, N-methylpyrrolidino, N-methylpiperidino, thietano, tetrahydrofurano and tetrahydropyrano.

Corresponding meanings can also be assigned to the substituents in composite definitions, for example cycloalkyl-alkyl, cycloalkylcarbonyl, cycloalkyl-alkoxycarbonyl-alkyl, cycloalkenyl-alkyl, phenylalkyl, phenylalkenyl, alkoxycarbonyl-alkyl, dialkylamino-alkyl, halogenoalkoxyphenyl, alkylaminocarbonyl-alkyl, dialkylaminocarbonyl-alkyl, alkoxyalkylamino, dialkoxyalkylamino, alkoxyalkoxycarbonyl, alkoxyalkoxycarbonyl-alkyl, alkoxycarbonyl-alkoxycarbonyl-alkyl, alkylaminocarbonyl, alkylaminocarbonyl-alkyl, dialkylaminocarbonyl-alkyl, alkylthio-alkoxycarbonyl, alkylthiocarbonyl, alkylthiocarbonyl-alkyl, halogenoalkoxycarbonyl-alkyl and alkenyloxy-alkyl.

The salts of the compounds of the formula I with an acid hydrogen, in particular of the derivatives with carboxylic acid groups (for example carboxyl-substituted alkyl, phenyl and pyrazolyl groups), are, for example, alkali metal salts, for example sodium and potassium salts; alkaline earth metal salts, for example calcium and magnesium salts; ammonium salts, i.e. unsubstituted ammonium salts and mono- or polysubstituted ammonium salts, for example triethylammonium and methylammonium salts; or salts with other organic bases.

The alkali metal and alkaline earth metal hydroxides as salt-forming agents are preferably, for example, the hydroxides of lithium, sodium, potassium, magnesium or calcium, and in particular those of sodium or potassium.

Examples of amines which are suitable for ammonium salt formation are ammonia and also primary, secondary and tertiary $C_1$–$C_{18}$alkylamines, $C_1$–$C_4$hydroxyalkylamines and $C_2$–$C_4$alkoxyalkylamines, for example methylamine, ethylamine, n-propylamine, iso-propylamine, the four isomeric butylamines, n-amylamine, iso-amylamine, hexylamine, heptylamine, octylamine, nonylamine, decylamine, pentadecylamine, hexadecylamine, heptadecylamine, octadecylamine, methyl-ethylamnine, methyl-iso-propylamine, methyl-hexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, di-iso-propylamine, di-n-butylamine, di-n-amylamine, di-iso-amylamine, dihexylamine, diheptylamine, dioctylamine, ethanolamine, n-propanolamine, iso-propanolamine, N,N-diethanolamine, N-ethylpropanolamine, N-butylethanolamine, allylamine, n-butenyl-2-amine, n-pentenyl-2-amine, 2,3-dimethylbutenyl-2-amine, di-butenyl-2-amine, n-hexenyl-2-amine, propylenediamine, trimethylamine, triethylamine, tri-n-propylamine, tri-iso-propylamine, tri-n-butylamine, tri-iso-butylamine, tri-sec-butylamine, tri-n-amylamine, methoxyethylamine and ethoxyethylamine; heterocyclic amines, for example pyridine, quinoline, iso-quinoline, morpholine, thiomorpholine, N-methylmorpholine, N-methyl-thiomorpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but in particular triethylamine, iso-propylamine and di-iso-propylamine.

The salts of the compounds of the formula I with basic groups, in particular of the derivatives with amino groups, for example alkylamino, dialkylamino, alkoxyalkylamino or alkenylamino, or of the derivatives with basic heterocyclic rings, for example pyridyl or pyrazolyl rings, are, for example, salts with inorganic and organic acids, for example hydrogen halide acid, such as hydrofluoric acid, hydrochloric acid, hydrobromic acid or hydriodic acid, as well as sulfuric acid, phosphoric acid, nitric acid and organic acids such as acetic acid, trifluoroacetic acid, trichloroacetic acid, propionic acid, glycolic acid, thiocyanic acid, citric acid, benzoic acid, oxalic acid, formic acid, benzenesulfonic acid, p-toluenesulfonic acid, methanesulfonic acid and salicylic acid.

Metal complexes can also be prepared with the compounds of the formula I.

The possible presence of at least one asymmetric carbon atom in the compounds of the formula I, for example in the group $W_1$, in which A is -$X_3R_4$, where $R_4$ is alkyl or alkyl substituted by alkoxycarbonyl, results in the compounds being able to occur both in optically active individual isomers and in the form of racemic mixtures. In the present invention, active ingredients of the formula I are to be understood as meaning both the pure optical antipodes and the racemates or diastereomers.

If an aliphatic C═C— or C═N—O— double bond (syn/anti) is present, geometric isomerisms can occur. The present invention also relates to these isomers.

Preferred compounds of the formula I are those in which
W is a group $W_1$ to $W_{11}$

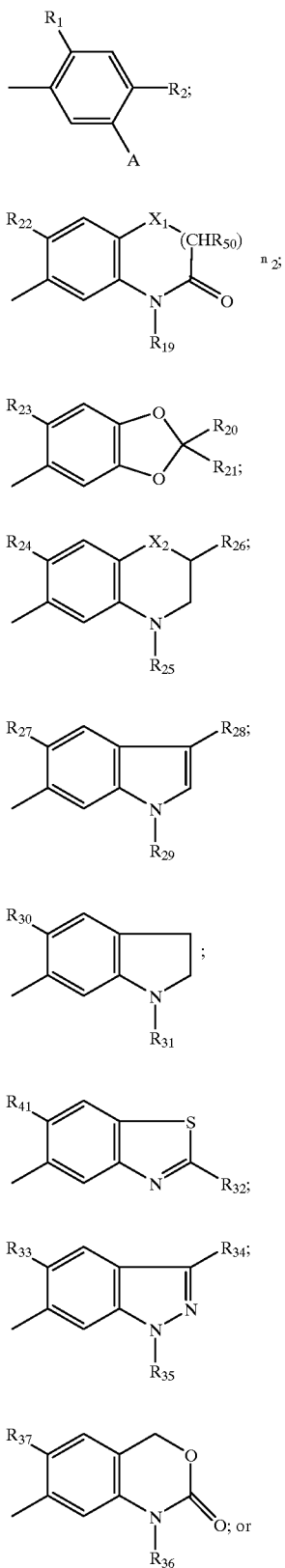

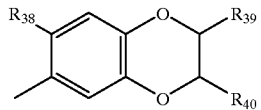

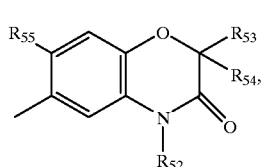

in which $R_1$, $R_{22}$, $R_{23}$, $R_{24}$, $R_{27}$, $R_{30}$, $R_{33}$, $R_{37}$, $R_{38}$, $R_{41}$ and $R_{55}$ independently of one another are hydrogen or halogen;

$R_2$ is cyano, amino, nitro, halogen, hydroxyl, $C_1$–$C_4$alkyl, $C_1$–$C_4$alkoxy, $C_1$–$C_4$halogenoalkoxy or $C_1$–$C_4$halogenoalkyl;

A is hydrogen, $C_1$–$C_6$alkyl, $C_3$–$C_8$cycloalkyl, $C_4$–$C_8$cycloalkenyl, $C_3$–$C_8$cyclo-alkyl-$C_1$–$C_6$alkyl, $C_4$–$C_8$cycloalkenyl-$C_1$–$C_6$alkyl, $C_2$–$C_6$alkenyl, $C_2$–$C_6$alkinyl, phenyl, phenyl-$C_1$–$C_6$alkyl, phenyl–$C_2$–$C_6$alkenyl, phenyl–$C_2$–$C_6$alkinyl, 5- or 6-membered heterocyclyl or 5- or 6-membered heterocyclyl-$C_1$–$C_6$alkyl, where the radicals listed for A can be substituted by $C_1$–$C_6$-alkyl, $C_1$–$C_6$-haloalkyl, $C_2$–$C_6$-alkenyl, $C_2$–$C_6$-alkynyl, halogen, cyano, nitro, —$COR_3$, —$X_3R_4$,

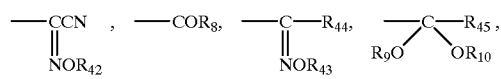

—$NR_{56}R_{57}$ or $NR_{56}OR_{57}$, or A is halogen, cyano, nitro, —$COR_3$, —$X_4R_4$,

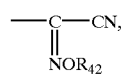

—$COR_{44}$,

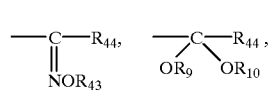

—$NR_{56}R_{57}$, —$NR_{56}OR_{57}$,

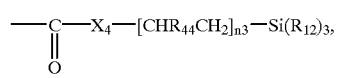

—$N(R_{13})$—$SO_2$—$R_{14}$,

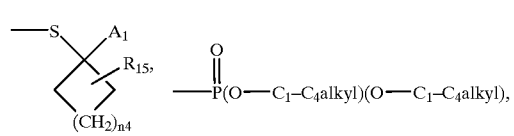

-continued

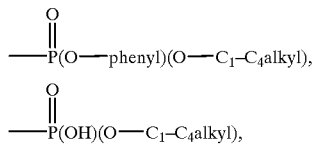

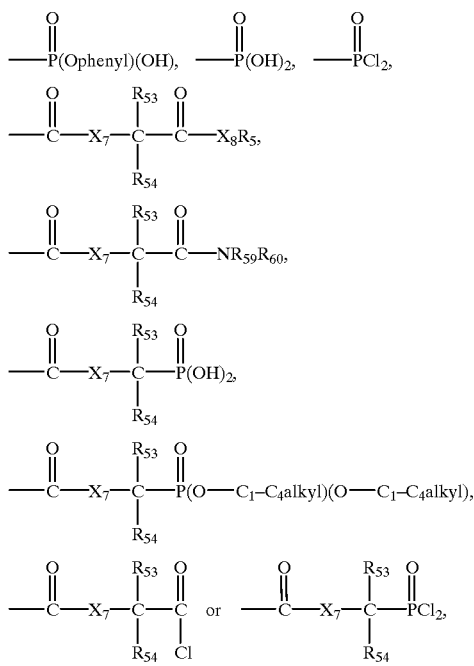

in which

R$_3$, X$_3$, R$_8$, R$_9$, R$_{10}$, R$_{56}$, R$_{57}$ and R$_{14}$ are as defined in claim 1;

R$_4$ is hydrogen, C$_1$–C$_{10}$alkyl, C$_1$–C$_4$alkoxy-C$_1$–C$_4$alkyl, C$_1$–C$_4$alkylthio-C$_1$–C$_4$alkyl, di-C$_1$–C$_4$alkylamino-C$_1$–C$_4$alkyl, C$_1$–C$_8$halogenoalkyl, C$_2$–C$_8$alkenyl, C$_2$–C$_8$halogenoalkenyl, C$_3$–C$_8$alkynyl, C$_3$–C$_7$cycloalkyl, oxetan-3-yl, halogeno-C$_3$–C$_7$-cycloalkyl, C$_1$–C$_8$alkylcarbonyl, C$_1$–C$_8$alkoxycarbonyl, allylcarbonyl, —SO$_2$CF$_3$, —SO$_2$C$_6$H$_5$, C$_3$–C$_7$cycloalkylcarbonyl, benzoyl, which is unsubstituted or substitued on the phenylring up to three times in an identical or different manner by halogen, C$_1$–C$_4$alkyl, C$_1$–C$_4$halogenoalkyl, C$_1$–C$_4$halogenoalkoxy or C$_1$–C$_4$alkoxy; C$_1$–C$_8$alkyl substituted by cyano, nitro, carboxyl, C$_1$–C$_8$alkylthio-C$_1$–C$_8$alkoxycarbonyl, phenyl, halogenophenyl, C$_1$–C$_4$alkylphenyl, C$_1$–C$_4$alkoxyphenyl, C$_1$–C$_4$halogenoalkylphenyl, C$_1$–C$_4$halogenoalkoxyphenyl, C$_1$–C$_6$alkoxycarbonyl, C$_1$–C$_4$alkoxy-C$_1$–C$_4$alkoxyl, C$_1$–C$_4$alkoxy-C$_1$–C$_8$alkoxycarbonyl, C$_3$–C$_8$alkenyloxycarbonyl, C$_3$–C$_8$alkynyloxycarbonyl, C$_1$–C$_8$alkylthiocarbonyl, C$_3$–C$_8$alkenylthiocarbonyl, C$_3$–C$_8$alkinylthiocarbonyl, carbamoyl, C$_1$–C$_4$alkylaminocarbonyl, di-C$_1$–C$_4$alkylaminocarbonyl, C$_3$–C$_8$alkenylaminocarbonyl, di-C$_3$–C$_8$alkenylaminocarbonyl, C$_1$–C$_4$alkyl—C$_3$–C$_8$alkenylaminocarbonyl, phenyloxycarbonyl or phenyl–C$_1$–C$_8$alkyloxycarbonyl, which is unsubstituted or substituted on the phenyl up to three times in an identical or different manner by halogen, C$_1$–C$_4$alkyl, cyano, nitro or amino; phenylaminocarbonyl, which is unsubstituted or substituted on the phenyl up to three times in an identical or different manner by halogen, C$_1$–C$_4$alkyl, C$_1$–C$_4$halogenoalkyl, C$_1$–C$_4$halogenoalkoxy or C$_1$–C$_4$alkoxy or once by cyano or nitro; dioxolan-2-yl, which is unsubstituted or substituted by one or two C$_1$–C$_4$alkyl radicals; or dioxanyl, which is unsubstituted or substituted by one or two C$_1$–C$_4$alkyl radicals;

R$_{43}$ is defined as R$_4$;

R$_{44}$ is hydrogen, C$_1$–C$_4$alkyl, C$_1$–C$_4$halogenoalkyl or C$_1$–C$_4$alkoxy-C$_1$–C$_4$alkyl;

R$_{45}$ is hydrogen, C$_1$–C$_4$alkyl, C$_1$–C$_4$halogenoalkyl or C$_1$–C$_4$alkoxy-C$_1$–C$_4$alkyl;

R$_{42}$ is defined as R$_{43}$;

X$_4$ is oxygen,

or sulfur, n$_3$ is 0, 1, 2, 3 or 4;

R$_{12}$ is C$_1$–C$_8$alkyl;

R$_{13}$ is hydrogen, C$_1$–C$_5$alkyl, benzyl, C$_1$–C$_4$halogenoalkyl, C$_3$–C$_8$alkenyl, C$_3$–C$_8$alkinyl, —SO$_2$R$_{14}$,—SO$_2$C$_6$H$_5$ or

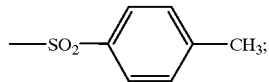

A$_1$ is cyano or —COR$_{16}$, in which

R$_{16}$ is chlorine, —X$_5$—R$_{17}$, amino, C$_1$–C$_4$alkylamino, di-C$_1$–C$_4$alkylamino, C$_2$–C$_4$-halogenoalkylamino, di-C$_2$–C$_4$halogenalkylamino, C$_1$–C$_4$alkoxyalkylamino, di-C$_1$–C$_4$-alkoxyalkylamino, C$_3$–C$_4$alkenylamino, diallylamino, -N-pyrrolidino, -N-piperidino, -N-morpholino, -N-thiomorpholino, -N-piperazino, or the group —O—N=C(CH$_3$)—CH$_3$, or —N(OR$_{46}$)—R$_6$, in which X$_5$ is oxygen or sulfur;

R$_{17}$ is hydrogen, C$_1$–C$_{10}$alkyl, C$_1$–C$_4$alkoxy-C$_1$–C$_4$alkyl, C$_2$–C$_8$halogenoalkyl, C$_1$–C$_{10}$-alkylthio-C$_1$–C$_4$alkyl, di-C$_1$–C$_4$alkylamino-C$_1$–C$_4$alkyl, cyano-C$_1$–C$_8$alkyl, C$_3$–C$_8$alkenyl, C$_3$–C$_8$halogenoalkenyl, C$_3$–C$_8$alkynyl, C$_3$–C$_7$cycloalkyl, C$_3$–C$_7$cycloalkyl-C$_1$–C$_4$alkyl, halogeno-C$_3$–C$_7$cycloalkyl or benzyl, which is unsubstituted or substituted on the phenyl ring up to three times in an identical or different manner by halogen, C$_1$–C$_4$alkyl, C$_1$–C$_4$halogenoalkyl, C$_1$–C$_4$halogenoalkoxy or C$_1$–C$_4$alkoxy; alkali metal, alkaline earth metal or ammonium ions, or the group—[CHR$_{47}$—(CH$_2$)$_m$]—COOR$_{48}$ or —[CHR$_{49}$—(CH$_2$)$_t$—Si(R$_{18}$)$_3$];

m is 0, 1, 2, 3 or 4;

t is 0, 1, 2, 3 or 4;

R$_{18}$ is C$_1$–C$_4$alkyl;

R$_{47}$ and R$_{49}$ independently of one another are hydrogen or C$_1$–C$_4$alkyl; and R$_{48}$ is defined as R$_7$ in claim 1;

R$_6$ and R$_{46}$ independently of one another are hydrogen or C$_1$–C$_4$alkyl;

$n_4$ is 0, 1, 2, 3 or 4;

$R_{15}$ is hydrogen, fluorine, chlorine, bromine, $C_1$–$C_4$alkyl or trifluoromethyl;

$X_7$ is oxygen, sulfur or —$NR_8$—, in which $R_8$ is as defined above;

$R_{53}$ and $R_{54}$ independently of one another are hydrogen, $C_1$–$C_4$alkyl, $C_1$–$C_4$halogenoalkyl, $C_2$–$C_6$alkenyl or $C_2$–$C_6$alkynyl, or $R_{53}$ and $R_{54}$, together with the carbon atom to which they are bonded, form a 3- to 6-membered carbocyclic ring;

$X_8$ is oxygen or sulfur;

$R_5$ is as defined in claim 1; and $R_{59}$ and $R_{60}$ independently of one another are defined as $R_{56}$ in claim 1;

$X_1$ is oxygen or sulfur, $n_2$ is 0, 1, 2, 3 or 4;

$R_{19}$ is hydrogen, $C_1$–$C_6$alkyl, $C_2$–$C_4$alkenyl or $C_2$–$C_6$alkynyl; halogen-substituted $C_1$–$C_6$alkyl, $C_2$–$C_4$alkenyl or $C_3$–$C_6$alkynyl; $C_1$–$C_4$alkoxy-$C_1$–$C_4$alkyl, $C_1$–$C_4$alkoxy-$C_1$–$C_2$alkoxy-$C_1$–$C_2$alkyl, 1-phenylpropen-3-yl, cyano or $C_3$–$C_6$cycloalkyl-substituted $C_1$–$C_6$alkyl; carboxy-$C_1$–$C_4$alkyl, $C_1$–$C_6$alkoxycarbonyl-$C_1$–$C_4$alkyl, $C_2$–$C_6$halogenoalkoxycarbonyl-$C_1$–$C_4$alkyl, $C_1$–$C_4$alkoxy-$C_1$–$C_2$alkoxycarbonyl-$C_1$–$C_4$alkyl, $C_1$–$C_6$alkoxycarbonyl-$C_1$–$C_2$alkoxycarbonyl-$C_1$–$C_4$alkyl, $C_3$–$C_6$cycloalkyl-$C_1$–$C_2$alkoxycarbonyl-$C_1$–$C_4$alkyl, $C_1$–$C_5$alkylaminocarbonyl-$C_1$–$C_4$alkyl, di-$C_1$–$C_4$alkylamino-$C_1$–$C_4$alkyl, di-$C_1$–$C_5$alkylaminocarbonyl-$C_1$–$C_4$alkyl, $C_3$–$C_6$cycloalkyl, $C_1$–$C_4$alkylthio-$C_1$–$C_4$alkyl, benzyl or halogen-substituted benzyl, $C_1$–$C_4$alkylsulfonyl, $C_3$–$C_6$alkenyloxy-$C_1$–$C_4$alkyl, $C_1$–$C_4$alkoxycarbonyl, $C_1$–$C_8$alylcarbonyl,

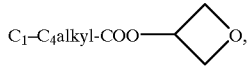

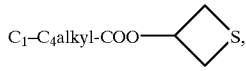

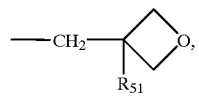

$C_1$–$C_4$alkylthiocarbonyl-$C_1$–$C_4$alkyl, or the group —[CHR$_{47}$—(CH$_2$)$_m$]COX$_6$—CHR$_{47}$—(CH$_2$)$_m$—COOR$_{48}$; in which $R_{47}$, $R_{48}$ and m are as defined above;

$X_6$ is oxygen or sulfur;

$R_{51}$, $R_{50}$, $R_{26}$, $R_{28}$, $R_{32}$, $R_{34}$, $R_{39}$ and $R_{40}$ independently of one another are hydrogen or $C_1$–$C_4$alkyl;

$R_{20}$ and $R_{21}$ independently of one another are hydrogen, $C_1$–$C_4$alkyl or fluorine;

$X_2$ is oxygen or sulfur;

$R_{25}$, $R_{29}$, $R_{31}$, $R_{35}$, $R_{36}$ and $R_{52}$ are defined as $R_{56}$; and $R_{53}$ and $R_{54}$ are as defined above.

Compounds of the formula I which are likewise preferred are those in which $R_{100}$ is hydrogen, $C_1$–$C_6$alkyl, $C_1$–$C_6$alkyl substituted by —COR$_3$, or $C_3$–$C_8$cycloalkyl, in which $R_3$ is —$X_4$—$R_5$, in which $X_4$ is oxygen or sulfur, and $R_5$ is $C_1$–$C_{10}$alkyl.

Compounds of the formula I which are also preferred are those in which $R_{101}$ is cyano,

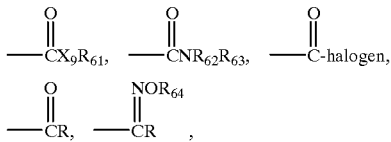

—NH$_2$, -nitro or

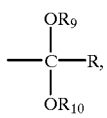

in which $X_9$, $R_{61}$, $R_{62}$, $R_{63}$, $R_{64}$, $R_9$ and $R_{10}$ are as defined in claim 1.

Preferred compounds are also those in which $R_{101}$ is cyano.

Compounds of the formula I which are furthermore preferred are those in which $R_{102}$ is hydrogen, halogen, $C_1$–$C_4$alkyl, $C_1$–$C_4$halogenoalkyl, cyano or $C_2$–$C_4$alkynyl.

Particularly preferred compounds of the formula I are those in which

W is a group $W_1$ or $W_2$. Of these compounds of the formula I, those which are most especially preferred are those in which, in the group $W_1$, $R_1$ is hydrogen or halogen;

$R_2$ is cyano, nitro or halogen; and

A is $C_1$–$C_6$alkyl or $C_2$–$C_6$alkynyl, where these radicals can be substituted by —COR$_3$, —$X_3R_4$,

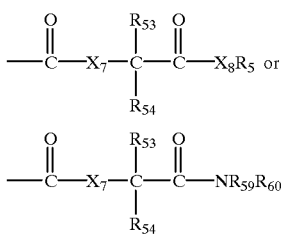

in which $R_3$ is —$X_4$—$R_5$, in which $X_4$ is oxygen or sulfur; and $R_5$ is $C_1$–$C_{10}$alkyl;

$X_3$ is oxygen or sulfur, $R_4$ is hydrogen, $C_1$–$C_4$alkyl, $C_1$–$C_4$alkyl substituted by cyano, carboxyl or $C_1$–$C_6$alkoxycarbonyl;

$X_7$ is oxygen or sulfur, $R_{53}$ and $R_{54}$ independendy of one another are hydrogen or $C_1$–$C_4$alkyl;

$X_8$ is oxygen or sulfur;

$R_5$ is $C_1$–$C_{14}$alkyl; and $R_{59}$ and $R_{60}$ independently of one another are hydrogen, $C_1$–$C_8$alkyl or $C_1$–$C_8$halogenoalkyl.

Preferred compounds of the formula I are those of the formula $I_0$

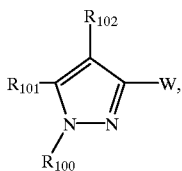

(I₀)

in which W, $R_{100}$, $R_{101}$ and $R_{102}$ are as defined under formula I.

A group of compounds of formula I to which very special importance is given, are those in which W is the group $W_1$; and $R_1$ is fluorine.

Very special importance is attached to the group of compounds of formula I, wherein W is the group $W_1$; and $R_1$ is hydrogen.

Another group of compounds of formula I to which very special preference is given, are those wherein W is the group $W_1$; $R_1$ is chlorine; A is $-X_4R_4$, $-NR_{56}R_{57}$, $-NR_{56}OR_{57}$ or $-N(R_{13})-SO_2-R_{14}$, in which $X_4$ is oxygen or sulfur, and $R_4$, $R_{13}$, $R_{14}$, $R_{56}$ and $R_{57}$ are as defined under formula I, with the proviso that $R_{57}$ may not be $C_1-C_8$alkoxycarbonyl-$C_1-C_4$alkyl if $R_{56}$ is hydrogen.

Another group of very important compounds of formula I are those wherein W is the group $W_1$; $R_1$ is chlorine; A is $C_1-C_6$alkyl, $C_3-C_8$cycloalkyl, $C_4-C_8$cycloalkenyl, $C_3-C_8$cycloalkyl-$C_1-C_6$alkyl, $C_4-C_8$cycloalkenyl-$C_1-C_6$alkyl, $C_2-C_6$alkenyl, $C_2-C_6$alkynyl, phenyl, phenyl-$C_1-C_6$alkyl, phenyl-$C_2-C_6$alkenyl, phenyl-$C_2-C_6$alkynyl, 5- or 6-membered heterocyclyl or 5- or 6-membered heterocyclyl-$C_1-C_6$alkyl, where the radicals listed for A can be substituted by $C_1-C_6$alkyl, $C_1-C_6$haloalkyl, $C_2-C_6$alkenyl, $C_2-C_6$alkynyl, halogen, cyano, nitro, $-COR_3$, $-X_3R_4$, $-COR_8$, $-NR_{56}R_{57}$ or $NR_{56}OR_{57}$, or A is halogen, cyano, $-COR_3$, $-COR_{44}$,

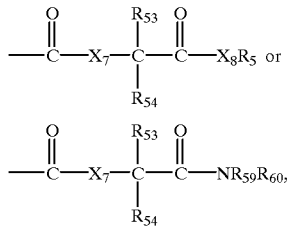

in which $R_3$ to $R_5$, $R_8$, $R_{44}$, $R_{53}$, $R_{54}$, $R_{56}$, $R_{57}$, $R_{59}$, $R_{60}$, $X_3$, $X_7$ and $X_8$ are as defined under formula I.

A further group of compounds of formula I to which very special preference is given, are those wherein $R_{100}$ is methyl; $R_{101}$ is cyano; $R_{102}$ is bromine, and W is as defined under formula I.

Another group of compounds of formula I with very special importance are those wherein
$R_{101}$ is

wherein $R_{62}$ and $R_{63}$ are as defined under formula I.

Very special importance is accorded to the group of compounds of formula I wherein W is a group selected from $W_2$ to $W_{11}$.

A further group with very special importance is encompassing compounds of formula I wherein $R_{100}$ is hydrogen, $C_2-C_6$alkyl, $C_3-C_8$cycloalkyl, $C_3-C_8$cycloalkyl-$C_1-C_6$alkyl, $C_3-C_6$alkenyl, $C_4-C_8$cycloalkenyl, $C_4-C_8$cycloalkenyl-$C_1-C_6$alkyl, $C_3-C_6$alkynyl, phenyl-$C_1-C_6$alkyl or cyano, where the groups listed for $R_{100}$, with the exception of hydrogen and cyano, can be substituted by halogen, $C_1-C_6$alkyl, $C_1-C_6$halogenoalkyl, cyano, nitro, $-COR_3$, $-X_3R_{04}$, $-COR_8$, $-NR_{56}R_{57}$ or $-NR_{56}OR_{57}$, in which $R_3$, $R_{04}$, $R_8$, $R_{56}$, $R_{57}$ and $X_3$ are as defined under formula I.

Furthermore there is a group of those compounds of formula I to which very special preference is given wherein $R_{100}$ is $C_2-C_6$alkyl, $C_3-C_8$cycloalkyl, $C_3-C_8$cycloalkyl-$C_1-C_6$alkyl, $C_3-C_6$alkenyl, $C_4-C_8$cycloalkenyl, $C_4-C_8$cycloalkenyl-$C_1-C_6$alkyl, $C_3-C_6$alkynyl, phenyl, phenyl-$C_1-C_6$alkyl or cyano, where the groups listed for $R_{100}$, with the exception of cyano, can be substituted by halogen, $C_1-C_6$alkyl, $C_1-C_6$halogenoalkyl, cyano, nitro, $-COR_3$, $-X_3R_{04}$, $-COR_8$, $-NR_{56}R_{57}$ or $-NR_{56}OR_{57}$, in which $R_3$, $R_{04}$, $R_8$, $R_{56}$, $R_{57}$ and $X_3$ are as defined under formula I.

The compounds of the formula I in which

W, $R_{100}$ and $R_{102}$ are as defined under formula I and $R_{101}$ is the radical $-CN$, can be prepared by processes which are known per se, for example by a) dehydrating a compound of the formula XXIIa or XXIIb

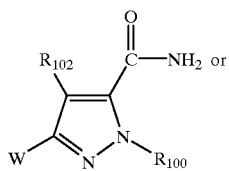

(XXIIa)

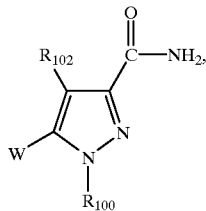

(XXIIb)

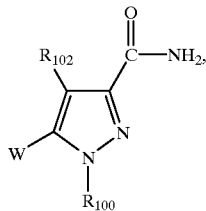

in which W, $R_{100}$ and $R_{102}$ are as defined; or b) first diazotizing a compound of the formula XXIIIa or XXIIIb

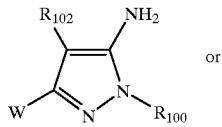

(XXIIIa)

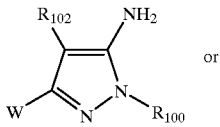

-continued

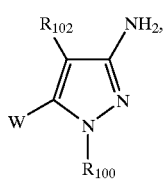
(XXIIIb)

in which W, $R_{100}$ and $R_{102}$ are as defined, and then reacting the diazonium salt formed with a salt of the formula XXXI

M⊕CN⊖   (XXXI), in which M⊕ is an alkali metal, alkaline earth metal or transition metal ion; or c) reacting a compound of the formula XXIVa or XXIVb

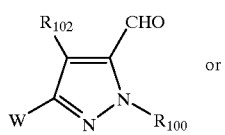
(XXIVa)

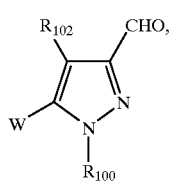
(XXIVb)

in which W, $R_{100}$ and $R_{102}$ are as defined, with hydroxylamine and dehydrating the oxime intermediately formed; or d) reacting a compound of the formula XXVa or XXVb

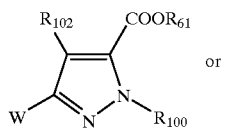
(XXVa)

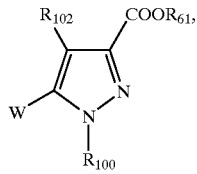
(XXVb)

in which W, $R_{61}$, $R_{100}$ and $R_{102}$ are as defined under formula I, with dimethylaluminium amide in the presence of an inert organic solvent.

The compounds of the formula I in which W, $R_{100}$ and $R_{102}$ are as defined under formula I and $R_{101}$ is the radical

can be obtained by a) reacting a compound of the formula XXIa or XXIb

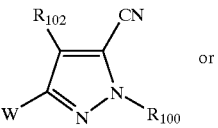
(XXIa)

or

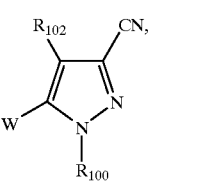
(XXIb)

in which W, $R_{100}$ and $R_{102}$ are as defined, with hydrogen sulfide in an organic solvent under base catalysis or with a source of hydrogen sulfide under acid catalysis; or b) reacting a compound of the formula XXIIa or XXIIb

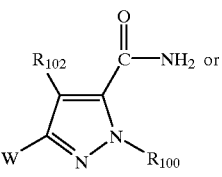
(XXIIa)

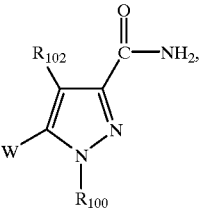
(XXIIb)

in which W, $R_{100}$ and $R_{102}$ are as defined, with a suitable sulfur reagent in a solvent.

The compounds of the formula I in which
W is as defined under formula I;
$R_{100}$ is $C_1$–$C_6$alkyl, $C_3$–$C_6$alkenyl or $C_3$–$C_6$alkynyl;
$R_{102}$ is halogen, in particular chlorine, bromine or iodine; and
$R_{101}$ is the radical —COOR$_{61}$, where
$R_{61}$ is $C_1$–$C_6$alkyl, $C_3$–$C_6$alkenyl or $C_3$–$C_6$alkynyl, can be obtained starting from a compound of the formula II

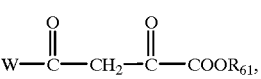
(II)

in which W and $R_{61}$, are as defined, either a) by converting the compound into the compound of the formula VIII

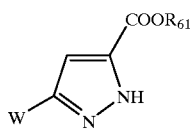
(VIII)

with hydrazine and subsequently alkylating this in the presence of a compound containing a corresponding $C_1$–$C_6$alkyl, $C_3$–$C_6$alkenyl or $C_3$–$C_6$alkynyl group, of the formula XXIXa

 (XXIXa)

or of the formula XXIXb

 (XXIXb), in which, in the compounds of the formulae XXIXa and XXIXb, the radical $R_{100}$ is as defined and $L_1$ is a leaving group, preferably chlorine, bromine, iodine, $CH_3SO_2O$— or

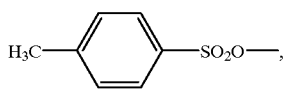

to give the compounds of the formulae IXa and IXb

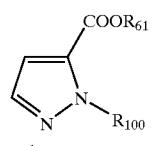
(IXa)

and

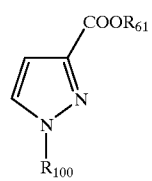
(IXb)

and then chlorinating, brominating or iodinating these; or
b) cyclizing this compound with the compound of the formula XXX

 (XXX), in which $R_{100}$ is as defined, to give the compounds of the formulae IXa and IXb

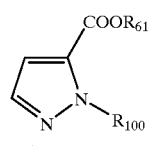
(IXa)

and

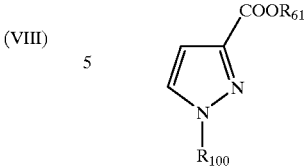
(IXb)

and then chlorinating, brominating or iodinating these.

The compounds of the formula I in which

W is as defined under formula I;

$R_{100}$ is $C_1$–$C_6$alkyl, $C_3$–$C_6$alkenyl or $C_3$–$C_6$alkynyl;

$R_{102}$ is hydrogen; and $R_{101}$ is the radical —$CH(OR_9)_2$, where $R_9$ is $C_1$–$C_4$alkyl, $C_2$–$C_4$halogenoalkyl or $C_2$–$C_8$alkoxyalkyl, can be obtained by cyclizing a compound of the formula V

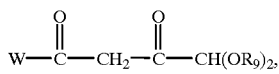
(V)

in which W and $R_9$ are as defined,
a) with hydrazine to give the compound of the formula XII

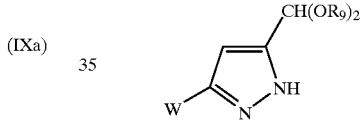
(XII)

and then alkylating this in the presence of a compound containing a corresponding $C_1$–$C_6$alkyl, $C_3$–$C_6$alkenyl or $C_3$–$C_6$alkynyl group, of the formula XXIXa

 (XXIXa)

or of the formula XXIXb

 (XXIXb), in which, in the compounds of the formulae XXIXa and XXIXb, the radical $R_{100}$ is as defined and $L_1$ is a leaving group, preferably chlorine, bromine, iodine, $CH_3SO_2O$— or

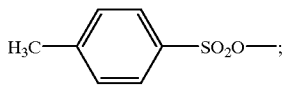

or
b) with a compound of the formula XXX

 (XXX)

in which $R_{100}$ is as defined.

The preparation of the compounds of the formula I is explained in more detail in the following reaction schemes 01, 3, 5 to 7 and 9 to 11.

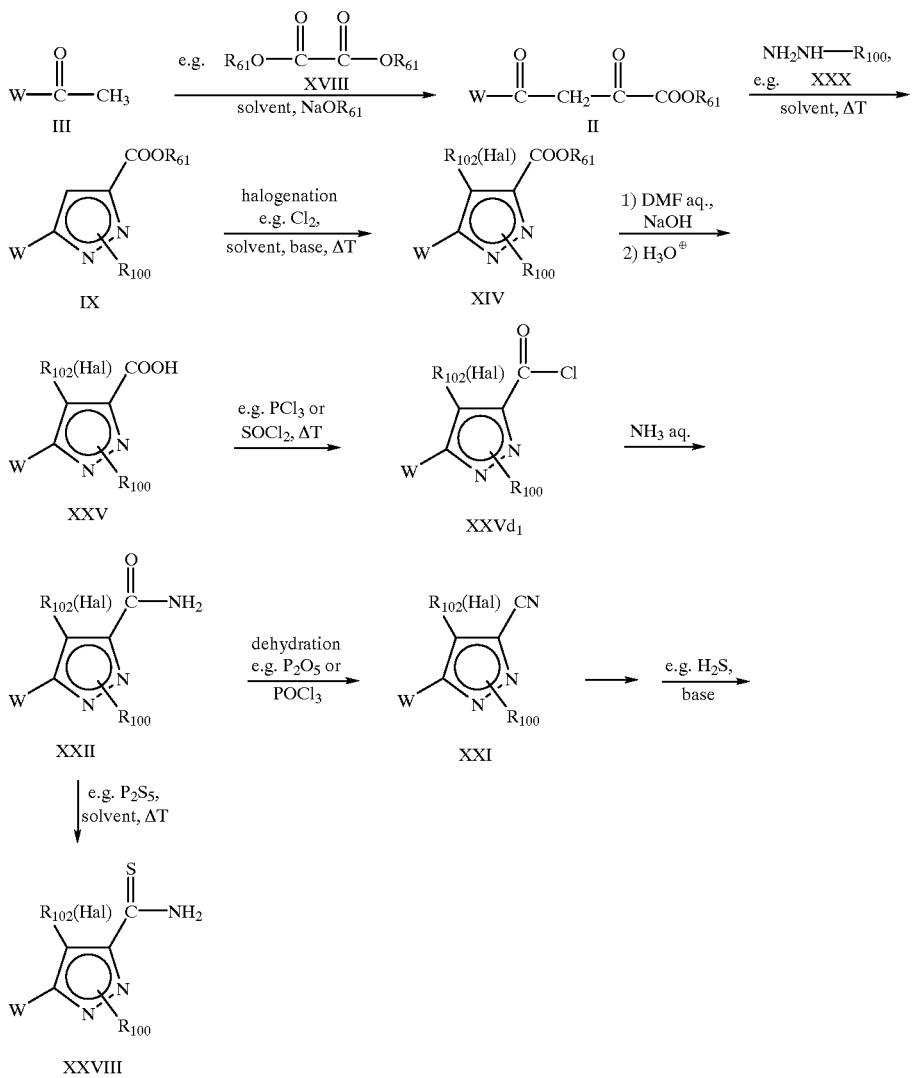

In reaction equation 01, the radicals W, $R_{61}$ and $R_{100}$ are as defined under formula I and $R_{102}$(Hal) is the halogen radical $R_{102}$, in particular chlorine, bromine or iodine.

The starting compounds of the formula III in reaction equation 01 can be prepared analogously to known processes, for example in accordance with methods a), b), c), d) and e) listed in the following reaction equation 1.

Reaction scheme 1

Method a):

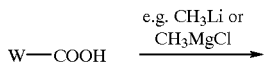

Method b):

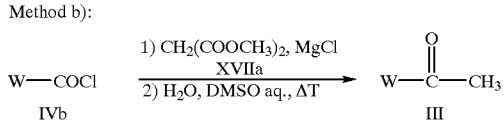

-continued

Method c):

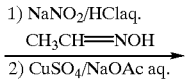

Method d):

Method e):

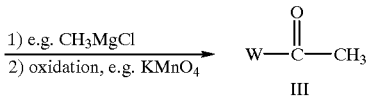

In reaction scheme 1, the radical W is an aromatic system $W_1$ to $W_{11}$, as defined under formula I, where it should be remembered that not every substituent definition is compatible with all the processes described. The choice of the suitable preparation method depends on the properties (reactivities) of the substituents in the particular intermediates.

The reaction according to method a) in reaction scheme 1 is carried out, for example, starting from the carboxylic acid of the formula IVa with methyllithium or a Grignard compound (methylmagnesium chloride or bromide) in an inert solvent, preferably diethyl ether, at temperatures of −100° C. to 50° C., analogously to Organic Reactions 18, 1 (1970), Organic Synthesis 49, 81 (1969) and 'Comprehensive Organic Transformations', Editor R. C. Larock, VCH 1989, page 685.

The reaction according to method b) in reaction scheme 1 is carried out analogously to Tetrahedron 48, 9233 (1992), by reacting the acid chloride of the formula IVb with a malonic acid diester (XVII), preferably dimethyl malonate of the formula XVIIa, in the presence of dry magnesium chloride and a base, for example triethylamine, in an inert solvent, for example toluene or diethyl ether, at temperatures of −20° C. to 50° C. The resulting crude product is then introduced into aqueous dimethyl sulfoxide (DMSO) at temperatures of 20° C. to 150° C. and worked up by customary methods.

The reaction according to method c) in reaction scheme 1 is carried out analogously to J. Chem. Soc. 1954, 1297. The amines of the formula IVc are first diazotized to give the corresponding diazonium salts and these are reacted with acetaldehyde oxime ($CH_3CH$=NOH). Subsequent hydrolysis, for example with aqueous sodium acetate and copper sulfate, gives the corresponding methyl ketone of the formula III.

The reaction according to method d) in reaction scheme 1 is carried out analogously to 'Vogel's Textbook of Practical Organic Chemistry', Longman 1989, pages 1006 et seq. In this reaction, the aromatic compound of the formula IV is reacted in the presence of an acetic acid derivative, for example acetyl chloride, and an acid, for example Lewis acids, such as aluminium chloride, with or without a solvent at temperatures of 0° C. to 150° C.

The reaction according to method e) in reaction scheme 1 is carried out analogously to 'Advanced Organic Chemistry', Editor J. March, McGraw-Hill Book Company, New York, 1985, pages 816 et seq. and 1057 et seq., starting from an aldehyde of the formula IVd by means of a Grignard reagent, for example methylmagnesium chloride or bromide, or by means of methyllithium in an inert solvent, preferably diethyl ether, at temperatures of −80° C. to 25° C., with subsequent oxidation of the alcohol to the ketone. Examples of oxidizing agents are potassium permanganate, pyridinium dichromate and sodium dichromate.

The starting compounds of the formulae IV, IVa, IVb, IVc and IVd are known and can be prepared by disclosed processes.

The intermediates of the formulae II, V, VI and VII can be prepared analogously to known processes from the methyl ketones of the formula III described above, for example in accordance with methods a), b), c) and d) listed in the following reaction scheme 2.

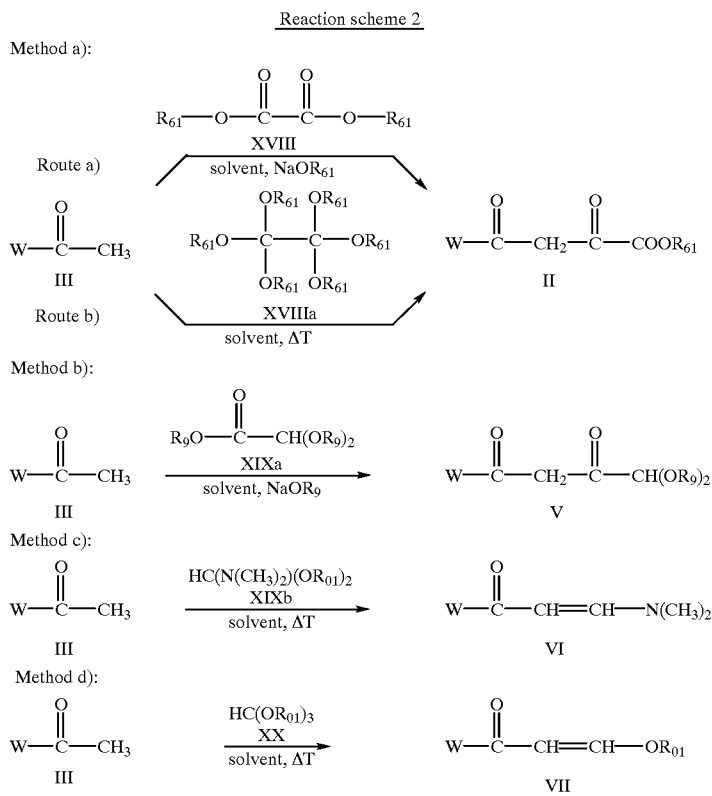

In reaction scheme 2, the radicals W, $R_9$ and $R_{61}$ are as defined under formula I and $R_{01}$ is $C_2$–$C_5$alkyl, in particular methyl or ethyl.

The reaction according to method a) in reaction scheme 2 gives the diketo esters of the formula II either according to route a): the methyl ketone of the formula III is reacted with an oxalic acid dialkyl ester of the formula XVIII, preferably dimethyl malonate, in the presence of a base, in particular the corresponding sodium alcoholate, in a solvent, for example the corresponding alcohol $R_{61}OH$, together with a second solvent, for example an ether or hydrocarbon, at temperatures of 0° C. up to the boiling point of the particular solvent, or according to route b): the methyl ketone of the formula III is reacted with a hexaalkoxyethane of the formula XVIIUa, preferably hexamethoxy- or hexaethoxyethane, with or without a solvent at temperatures from 20° C. up to the boiling point of the particular reaction medium. If the reaction is carried out in a solvent, toluene is preferred. The reaction can be catalysed by acids, for example hydrochloric acid, sulfuric acid, methanesulfonic acid, p-toluenesulfonic acid or trifluoroacetic acid.

The reactions according to methods c) and d) in reaction scheme 2 proceed analogously to those described under a) and give the intermediates of the formulae VI and VII. If the methyl ketone of the formula III is reacted on the one hand with acetals of N,N-dimethylformamide of the formula XIXb, preferably N,N-dimethylformamide dimethyl or diethyl acetal, intermediates of the formula VI are formed, or on the other hand with formic acid ortho esters of the formula XX, preferably methyl or ethyl orthoformate, the intermediates of the formula VII are formed.

The reaction of the methyl ketones of the formula III according to method b) in reaction scheme 2 with acetal esters of the formula XIXa, preferably methyl dimethoxyacetate or ethyl diethoxyacetate, in the presence of a base, preferably sodium methoxide or sodium ethoxide, and a solvent, in particular methanol or ethanol, at temperatures of 0° C. up to the boiling point of the reaction mixture gives the diketo acetals of the formula V. In certain cases, a further solvent, for example ether, can also be added.

The preparation processes for the pyrazole rings are explained in more detail in the following reaction schemes 3, 4 and 5.

Reaction scheme 3

Method a):

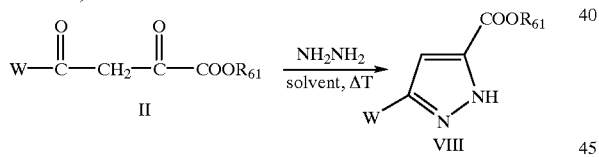

Method b):

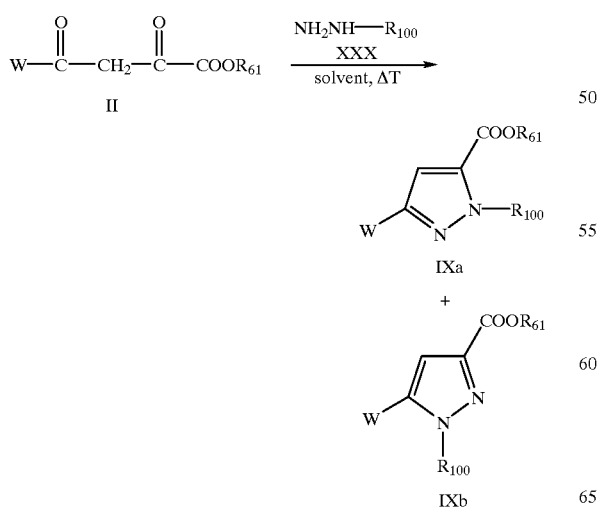

Reaction scheme 4

Method a):

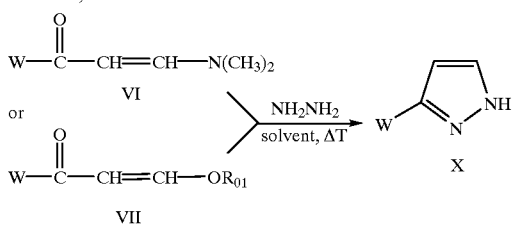

Method b):

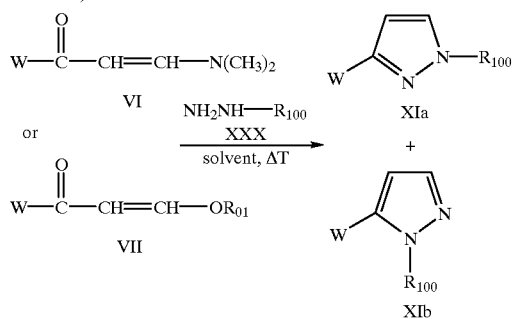

Reaction scheme 5

Method a):

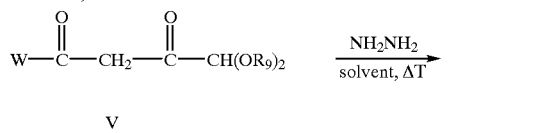

Method b):

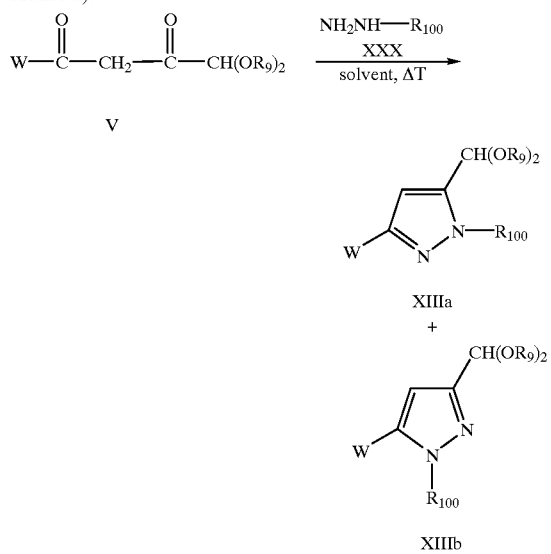

The preparation of the pyrazole rings of the formulae VIII (reaction scheme 3, method a)) and X (reaction scheme 4, method a)) which are unsubstituted on the nitrogen atoms is carried out by reaction of the compounds of the formulae II, VI or VII with hydrazine or hydrazine hydrate at elevated temperature.

For preparation of the compound of the formula VIII, glacial acetic acid or an alcohol is preferably used as the solvent under gentle reflux, and for preparation of the compound of the formula X, toluene is preferably used at elevated temperature. If appropriate, an acid, for example sulfuric acid or p-toluenesulfonic acid, can be added as a catalyst.

The preparation of the pyrazole ring of the formula XII (reaction scheme 5, method a)) which is unsubstituted on the nitrogen atom is preferably carried out starting from the compounds of the formula V in alcoholic solution with hydrazine hydrate at elevated temperature. For preparation of the pyrazole rings substituted on the nitrogen atom (reaction scheme 3, 4 and 5, method b)), the procedure is analogous to that described under method a), the compound of the formula XXX, for example N-alkylhydrazine, preferably N-methylhydrazine, being employed as a reagent.

The processes according to method b) lead to isomer mixtures IXa and IXb, XIa and XIb or XIIa and XIIIb, the ratio of the two isomers depending on the reaction conditions on the one hand and on the corresponding intermediates of the formulae II, VI, VII and V on the other hand.

The mixtures of the isomeric pyrazole esters of the formulae IXa and IXb can easily be separated into the pure isomers by means of silica gel chromatography and/or recrystallization. The same also applies in general to the isomer mixtures of the formulae XIa and XIb, and XIIIa and XIIIb.

In certain cases it is advantageous to prepare the N-alkyl-substituted pyrazole derivatives, in particular the N-methyl-substituted pyrazole derivatives, via N-alkylation of the corresponding unsubstituted pyrazoles of the formulae VIII, X or XII. Reaction scheme 6 explains this.

Reaction scheme 6

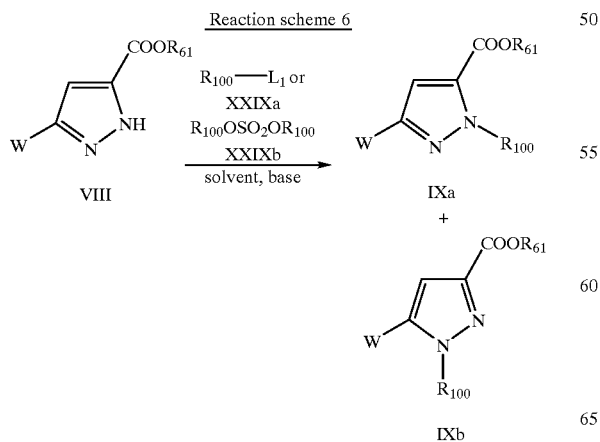

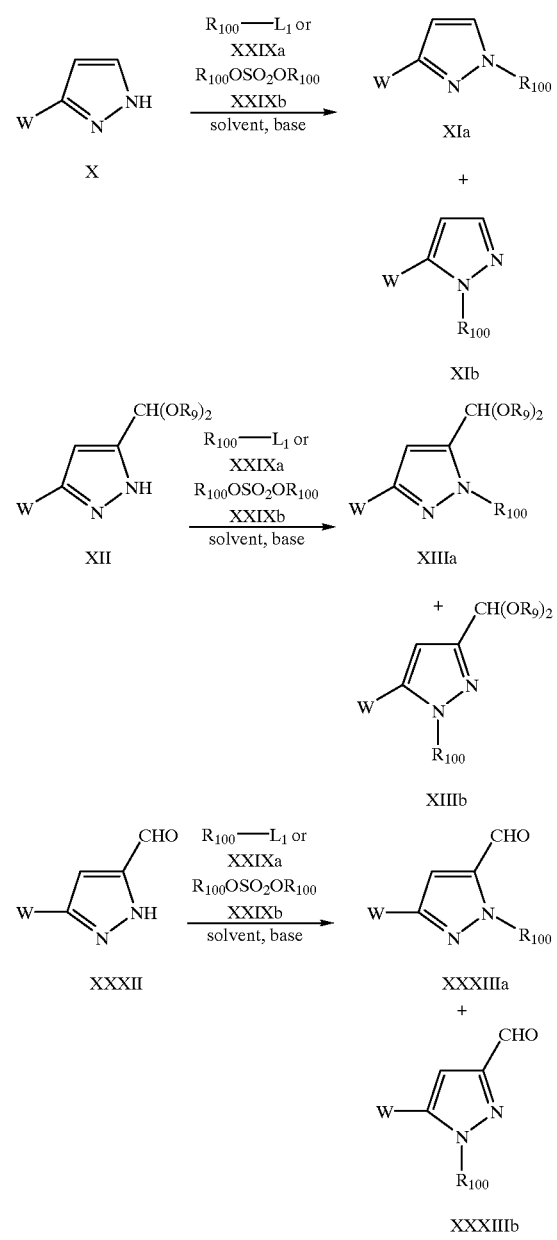

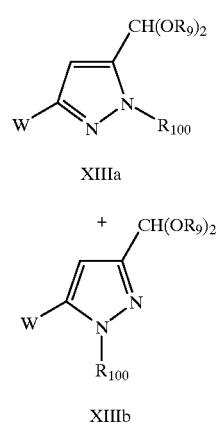

-continued

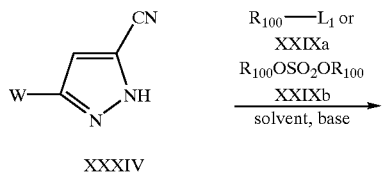

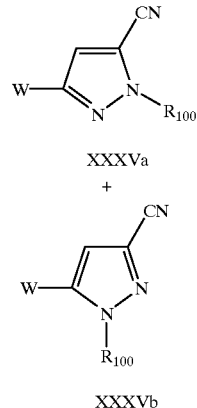

In reaction schemes 3 to 6, the radical W is an aromatic system $W_1$ to $W_{11}$ as defined under formula I, $R_9$ is as defined under formula I, $R_{61}$, $R_{100}$ and $R_{01}$ are $C_1$–$C_6$alkyl, $C_3$–$C_6$alkenyl or $C_3$–$C_6$alkynyl, and $L_1$ is a leaving group, for example chlorine, bromine, iodine, $CH_3SO_2O$— or

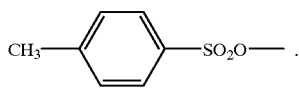

The N-alkylanton of the pyrazole rings in the compounds of the formulae VIII, X, XII, XXXII and XXXIV in reaction scheme 6 is carried out at room temperature or slightly elevated temperatures in the presence of a solvent, for example acetone, methyl ethyl ketone, N,N-dimethylformamide, N-methylpyrrolidone or dimethyl sulfoxide, a base, for example potassium carbonate, sodium carbonate, sodium hydroxide or potassium hydroxide, and an alkylating agent of the formula XXIXa or XXIXb, preferably methyl iodide or dimethyl sulfate.

The N-alkylation of the pyrazole rings leads to isomer mixtures of the formulae IXa and IXb, XIa and XIb, XIIIa and XIIIb, XXXIIIa and XXXIIIb, and XXXVa and XXXVb, which can in general be separated into the pure isomers by customary processes.

The halogenation of the 4-position of the pyrazole ring is explained in more detail in reaction schemes 7, 8 and 9.

Reaction scheme 7

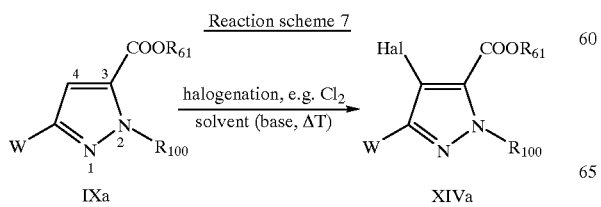

-continued

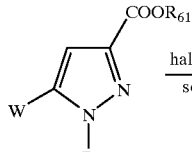

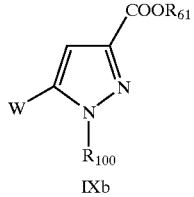

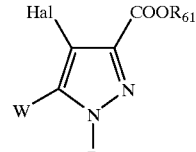

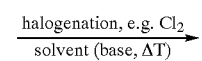

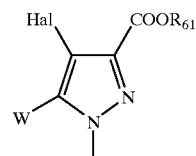

Reaction scheme 8

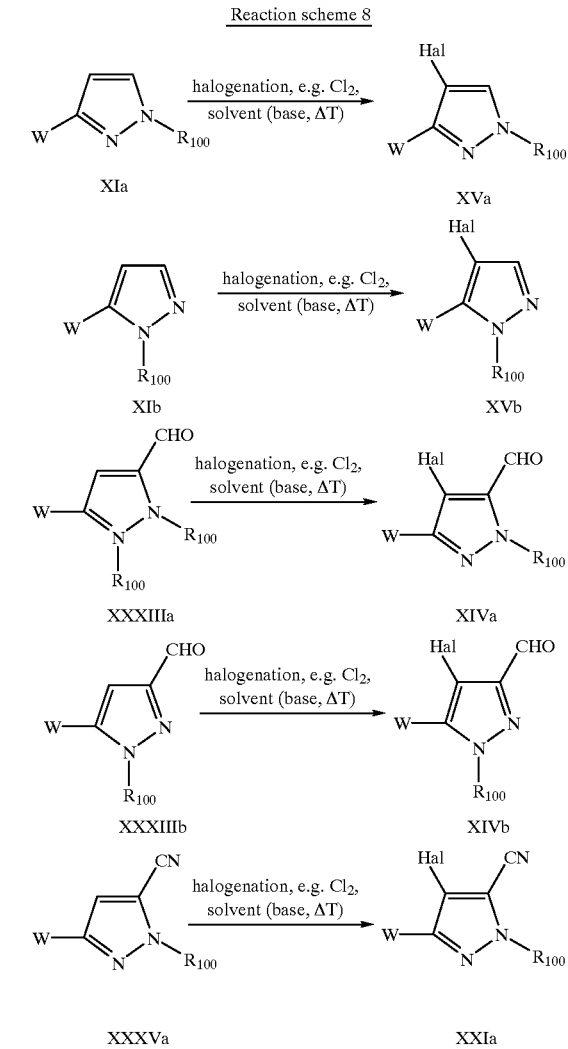

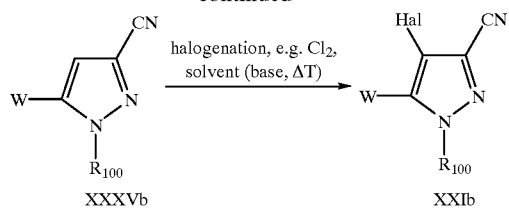

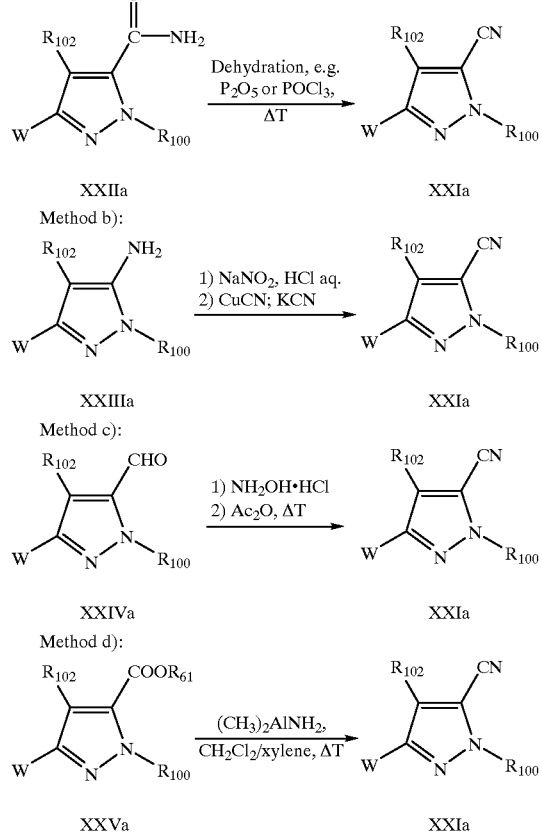

In reaction schemes 7 to 9, the radical W is an aromatic system $W_1$ to $W_{11}$ as defined above, Hal is halogen, in particular chlorine and bromine, $R_9$ is $C_1$–$C_6$alkyl, $C_3$–$C_6$alkenyl or $C_3$–$C_6$alkynyl, and $R_{61}$ and $R_{100}$ are hydrogen, $C_1$–$C_6$alkyl, $C_3$–$C_6$alkenyl or $C_3$–$C_6$alkynyl.

The halogenation of the isomeric pyrazolecarboxylic acid derivatives of the formulae IXa and IXb in reaction scheme 7 is carried out by means of a dihalogen molecule, preferably $Cl_2$, $Br_2$, $I_2$, F-I or Cl-I, the iodine derivative mainly being formed with the last two reagents, in a suitable solvent, preferably glacial acetic acid or carbon tetrachloride, at temperatures of 10° C. to the reflux temperature of the particular reaction mixture. In certain cases it is advantageous to carry out the halogenation in the presence of a base, for example sodium acetate, it being possible for the base to be added either before or during the course of the halogenation. If appropriate, a catalyst, for example aluminium chloride, iron(II) chloride or iron powder, can be added to the reaction mixture to accelerate the halogenation.

The halogenation of the isomeric pyrazole derivatives of the formulae XIa and XIb, XXXIIIa and XXXIIIb and XXXVa and XXXVb in reaction scheme 8 is carried out analogously to that described under reaction scheme 7 in the 4-position of the pyrazole ring and gives the isomeric halogenopyrazoles of the formulae XVa and XVb. The end products can be prepared in a pure form by customary methods, for example by means of silica gel chromatography and/or recrystallization.

The halogenation of the isomeric acetal-pyrazoles of the formulae XIIIa and XIIb in reaction scheme 9 is preferably carried out, for example, in glacial acetic acid, if appropriate with the addition of sodium acetate, at temperatures of 15° C. to the reflux temperature of the reaction mixture. The isomeric pyrazole-aldehydes halogenated in the 4-position, of the formulae XVIa and XVIb, are obtained as products.

The preparation of the pyrazole derivatives of the formula XXIa substituted by nitrile in the 3-position starting from the various intermediates of the formulae XXIIa, XXIIIa, XXIVa and XXVa is explained in reaction scheme 10. The choice of the suitable preparation method and the corresponding reaction conditions depends here on the properties (reactivities) of the substituents in the particular intermediates.

In reaction scheme 10, the radicals W and $R_{61}$ are as defined under formula I, $R_{100}$ is $C_1$–$C_6$alkyl, $C_3$–$C_6$alkenyl or $C_3$–$C_6$alkynyl, and $R_{102}$ is fluorine, chlorine, bromine, iodine, $CH_3$, $CF_3$, CN or —C≡CH.

The reaction according to method a) in reaction scheme 10 is carried out analogously to 'Advanced Organic Chemistry', Editor J. March, McGraw-Hill Book Company, N.Y., 1985, page 932 et seq. and converts primary amides of the formula XXIIa into the nitrilopyrazoles of the formula XXIa by dehydration, for example with phosphorus pentoxide ($P_2O_5$), phosphorus oxychloride ($POCl_3$) or carbon tetrachloride/triphenylphosphine ($CCl_4/P(C_6H_5)_3$), if appropriate in the presence of an inert solvent, at elevated temperature.

The reaction according to method b) in reaction scheme 10 is carried out analogously to 'Vogel's Textbook of Practical Organic Chemistry', 1989, page 938; aminopyrazoles of the formula XXIIIa are accordingly first diazotized in aqueous hydrochloric acid with sodium nitrite at low temperatures, for example −10° C. to 15° C., and the diazonium salts formed are converted into the nitrile derivatives of the formula XXIa with an aqueous solution of a salt of the formula XXXI

    (XXXI), in which M⊕ is an alkali metal, alkaline earth metal or transition metal ion, for example copper(I) cyanide or potassium cyanide (Sandmeyer reaction).

The reaction according to method c) in reaction scheme 10 is carried out analogously to 'Vogel's Textbook of Practical Organic Chemistry', Longman 1989, page 1084, and reacts pyrazole-aldehydes of the formula XXIVa with hydroxylamine hydrochloride in protic solvents to give oximes, which are dehydrated in acetic anhydride at elevated temperature to give the nitrilopyrazoles of the formula XXIa.

The reaction according to method d) in reaction scheme 10 uses ester-pyrazoles of the formula XXVa, which can be converted directly into the nitrites of the formula XXIa with the aid of dimethyl-aluminium amide $((CH_3)_2AlNH_2)$, freshly prepared from commercially obtainable trimethyla-luminium by known processes, in a mixture of inert solvents, preferably hexane, heptane, methylene chloride or xylene, by heating at the reflux temperature.

The reagents of the formulae XXIXa, XXIXb, XXX and XXXI used are known.

The pyrazolecarboxylic acids of the formula XXVc

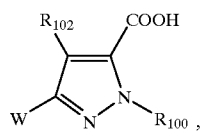

(XXVc)

can be obtained analogously to known processes a) by hydrolysis, preferably with aqueous alcohols, aqueous tetrahydrofuran or aqueous N,N-dimethylformamide, in the presence of sodium hydroxide or potassium hydroxide at moderate temperatures, for example 0° C. to the reflux temperature of the reaction mixture, and subsequent acid working up from the corresponding ester derivatives of the formula XXVa

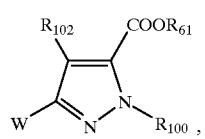

(XXVa)

in which, in the compounds of the formulae XXVa and XXVc, the radicals W, $R_{61}$, $R_{100}$ and $R_{102}$ are as defined under formula I, or b) by oxidation of an aldehyde of the formula XXIVa

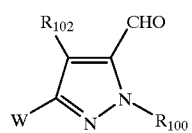

(XXIVa)

for example with potassium permanganate.

The pyrazolecarboxylic acid chlorides of the formula XXVd

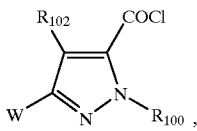

(XXVd)

can be prepared analogously to known processes, for example 'Organikum', Ed. J. A. Barth, Leipzig, 1993, page 439 et seq., from the corresponding pyrazolecarboxylic acids of the formula XXVc

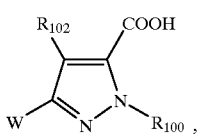

(XXVc)

in which, in the compounds of the formulae XXVc and XXVd, the radicals W, $R_{100}$ and $R_{102}$ are as defined, with inorganic acid chlorides, for example phosphorus trichloride or thionyl chloride, at elevated temperature, if appropriate in the presence of an inert solvent.

The pyrazolecarboxylic acid amides of the formula XXVIa

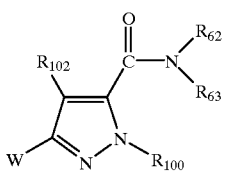

(XXVIa)

can be prepared analogously to known processes, for example as described in 'Organikum', Ed. J. A. Barth, Leipzig, 1993, page 425 et seq., a) from the corresponding carboxylic acid chlorides of the formula XXVd

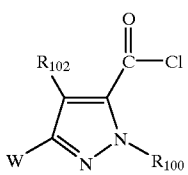

(XXVd)

and an amine of the formula XXVII

    (XXVII)

in the presence of a solvent, if appropriate with the addition of a base, for example triethylamine, alkali metal hydroxides or pyridine, at moderate temperatures, or b) from certain ester derivatives of the formula XXVa

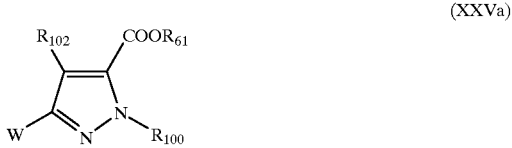
(XXVa)

by heating in the presence of an amine of the formula XXVII $HNR_{62}R_{63}$ (XXVII), in which, in the formulae XXVIa, XXVd, XXVII and XXVa, the radicals W, $R_{61}$, $R_{62}$, $R_{63}$, $R_{100}$ and $R_{102}$ are as defined under formula I, where $R_{61}$ is methyl in particular.

For preparation of primary pyrazole-amides of the formula XXIIa

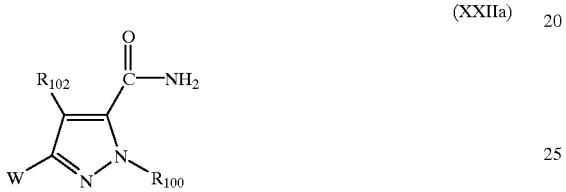
(XXIIa)

the corresponding acid chloride of the formula XXVd is reacted with aqueous ammonia solution.

The pyrazole-aldehydes of the formula XXIVa

(XXIVa)

can be prepared by known processes, for example as described in Arch. Pharm. 264, 337 (1926) and Liebigs Annalen 437, 297 (1924), a) from the corresponding acid chlorides of the formula XXVd

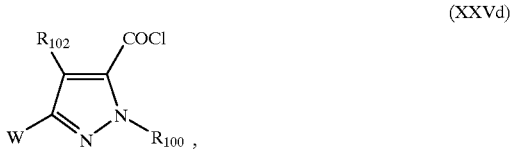
(XXVd)

or b) from the corresponding acetals of the formula XIIIc

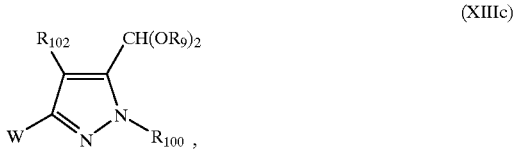
(XIIIc)

in which, in the compounds of the formulae XXIVa, XXVd and XIIc, the radicals W, $R_9$, $R_{100}$ and $R_{102}$ are as defined under formula I, by acid hydrolysis, for example with hydrochloric acid, sulfuric acid or p-toluenesulfonic acid.

The preparation of the pytazolethioamides of the formula XXVIIIa starting from the corresponding pyrazolenitriles of the formula XXIa or pyrazole-amides of the formula XXIIa is carried out analogously to known processes, for example as described in 'Methodicum Chimicum', Volume 6, Georg Thieme Verlag, Stuttgart, 1974, page 768 et seq. and 'Methoden der Organischen Chemie' (Methods of Organic Chemistry) (Houben-Weyl), Volume E5, Georg Thieme Verlag, Stuttgart, 1985, page 1242 et seq., and is explained in reaction scheme 11.

Reaction scheme 11

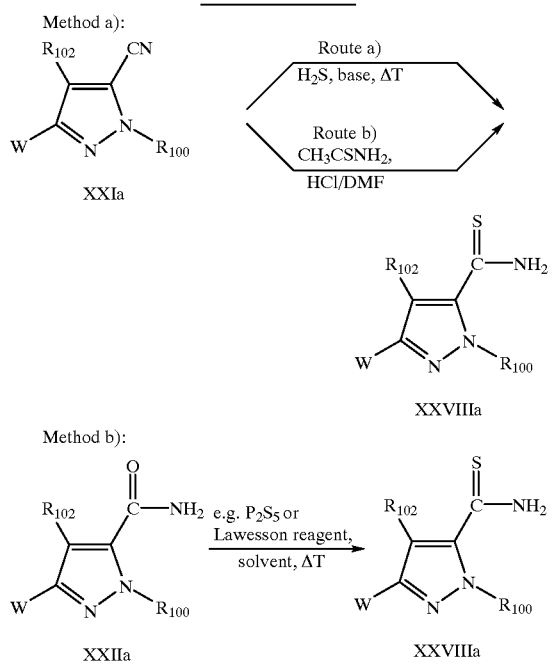

In reaction scheme 11, the radicals W, $R_{100}$ and $R_{102}$ in the compounds of the formula XXIa, XXVa and XXVIIIa are as defined under formula I, taking into account the reactivities and stabilities of the substituents under the reaction conditions chosen.

The reaction according to method a), route a) in reaction equation 11 uses pyrazolenitriles of the formula XXIa, which can be converted into the pyrazolethioamides of the formula XXVIIIa with hydrogen sulfide under base catalysis, for example with metal hydroxides, basic ion exchangers, alkanolates, ammonia or organic bases, for example pyridine and triethylamine, in an organic solvent, for example pyridine or an alcohol. The use of a stronger base, for example tetramethylguanidine, as the catalyst in solvents such as sulfolane may be indicated. The reaction temperatures may vary greatly according to the reactivity of the reactants; if appropriate, the reaction can also be carried out in a pressure reactor.

The reaction according to method a), route b), in reaction scheme 11 also uses pyrazolenitriles of the formula XXIa, which can be converted into the corresponding pyrazolethioamides of the formula XXVIIIa with a source of hydrogen sulfide, for example thioacetamide, in dry N,N-dimethylformamide under acid catalysis, for example with dry hydrogen chloride, at temperatures of 20° C. to 150° C.

The reaction according to method b) in reaction scheme 11 starts from primary amides of the formula XXIIa, which give the pyrazolethioamides of the formula XXVIIIa in the presence of the sulfur reagents mentioned under method a)

or other sulfur reagents, for example Lawesson reagent, phoshorus pentasulfide or iron sulfide, in various polar and non-polar solvents, for example toluene, xylenes, tetrahydrofuran, chloroform, dioxane or N,N-dimethylformamide, at temperatures of 20° C. to 150° C.

All the other compounds originating from the scope of formula I can easily be prepared in a manner analogous to those described above or by methods such as are described, for example, in "Methoden der Organischen Chemie (Methods of Organic Chemistry)" (Houben-Weyl), Volume E 8b, Georg Thieme Verlag Stuttgart, 1994, page 399 et seq. or in "Pyrazoles, Pyrazolines, Pyrazolidines, Indazoles and Condensed Rings", Editor R. H. Wiley, Interscience Publishers, New York, 1967, page 1 et seq., or from the compounds of the formula I described by derivatization by known standard methods.

The end products of the formula I can be isolated in the customary manner by concentration and/or evaporation of the solvent and can be purified by recrystallization or trituration of the solid residue in solvents in which the end products do not dissolve readily, such as ethers, aromatic hydrocarbons or chlorinated hydrocarbons, by distillation or by means of column chromatography or flash column chromatography and a suitable eluent.

The compounds of the formula IIa

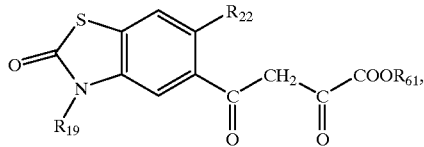

(IIa)

in which $R_{19}$ is hydrogen, $C_1$–$C_6$alkyl or $C_2$–$C_4$alkenyl;

$R_{22}$ is hydrogen or halogen; and $R_{61}$ is hydrogen or $C_1$–$C_{10}$alkyl, are novel and have been developed specifically for synthesis of the compounds of the formula I. The present invention therefore also relates to them.

The compounds of the formula IIb

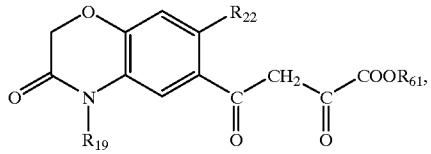

(IIb)

in which $R_{19}$ is hydrogen, carboxy-$C_1$–$C_4$alkyl, $C_2$–$C_4$alkenyl or $C_2$–$C_6$alkynyl;

$R_{22}$ is hydrogen or halogen; and $R_{61}$ is hydrogen or $C_1$–$C_{10}$alkyl, are novel and have been developed specifically for synthesis of the compounds of the formula I. The present invention therefore also relates to them.

The compounds of the formula IIIa

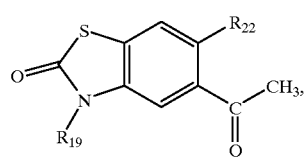

(IIIa)

in which $R_{19}$ is hydrogen, $C_1$–$C_6$alkyl, carboxy-$C_1$–$C_4$alkyl, $C_1$–$C_6$alkoxycarbonyl-$C_1$–$C_4$alkyl, $C_2$–$C_4$alkenyl or $C_2$–$C_6$alkynyl; and $R_{22}$ is hydrogen or halogen, are novel and have been developed specifically for synthesis of the compounds of the formula I. The present invention therefore also relates to them.

The compounds of the formula IIIb

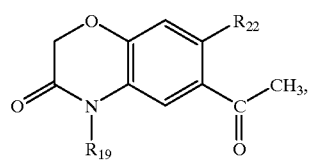

(IIIb)

in which $R_{19}$ is hydrogen, carboxy-$C_1$–$C_4$alkyl, $C_1$–$C_6$alkoxycarbonyl-$C_1$–$C_4$alkyl, $C_2$–$C_4$alkenyl or $C_2$–$C_6$alkynyl; and $R_{22}$ is hydrogen or halogen, are novel and have been developed specifically for synthesis of the compounds of the formula I. The present invention therefore also relates to them.

All the application methods customary in agriculture, for example preemergence application, postemergence application and seed dressing, as well as various methods and techniques, for example controlled release of the active ingredient, are suitable for the use according to the invention of the compounds of the formula I or compositions containing these. For this use, the active ingredient is absorbed in solution onto mineral carrier granules or polymerized granules (urea/formaldehyde) and dried. If appropriate, a coating which allows the active ingredient to be released in metered form over a certain period of time can additionally be applied (coated granules).

The compounds of the formula I can be employed in unchanged form, i.e. as they are obtained in the synthesis, but they are preferably processed in the customary manner with the auxiliaries conventionally used in the art of formulation, for example to emulsifiable concentrates, directly sprayable or dilutable solutions, dilute emulsions, wettable powders, soluble powders, dusts, granules or microcapsules. The methods of use, such as spraying, atomizing, dusting, wetting, scattering or pouring are chosen according to the required aims and the given circumstances, as is the nature of the compositions.

The formulations, i.e. the compositions, preparations or mixtures comprising the active ingredient of the formula I or at least one active ingredient of the formula I and as a rule one or more solid or liquid formulation auxiliaries are prepared in a known manner, for example by intimate mixing and/or grinding of the active ingredients with the formulation auxiliaries, for example solvents or solid carriers. Surface-active compounds (surfactants) furthermore can additionally be used during preparation of the formulations.

Solvents can be: aromatic hydrocarbons, in particular the $C_8$ to $C_{12}$ fractions, such as mixtures of alkylbenzenes, for example xylene mixtures, or alkylated naphthalenes; aliphatic and cycloaliphatic hydrocarbons, such as paraffins, cyclohexane or tetrahydronaphthalene; alcohols, such as ethanol, propanol or butanol; glycols and ethers and esters thereof, such as propylene glycol ethers or dipropylene glycol ethers, ketones, such as cyclohexanone, isophorone or diacetone alcohol, and strongly polar solvents, such as N-methyl-2-pyrrolidone, dimethyl sulfoxide or water; vegetable oils and esters thereof, such as rapeseed oil, castor oil or soya oil; and if appropriate also silicone oils.

Natural rock powders, such as calcite, talc, kaolin, montmorillonite or attapulgite, are as a rule used as solid carriers, for example for dusts and dispersible powders. Highly disperse silicic acid or highly disperse absorbent polymers can also be added to improve the physical properties. Granular adsorptive carrier granules are porous types, for example pumice, crushed brick, sepiolite or bentonite, and non-absorbent carrier materials are, for example, calcite or sand. A large number of pregranulated materials of inorganic or organic nature, such as, in particular, dolomite or comminuted plant residues, can also be used.

Surface-active compounds are nonionic, cationic and/or anionic surfactants having good emulsifying, dispersing and wetting properties, depending on the nature of the active ingredient of the formula I to be formulated. Surfactants are also to be understood as meaning surfactant mixtures.

Suitable anionic surfactants can be either so-called water-soluble soaps or water-soluble synthetic surface-active compounds.

Soaps are the alkali metal, alkaline earth metal or substituted or unsubstituted ammonium salts of higher fatty acids ($C_{10}$–$C_{22}$), for example the Na or K salts of oleic or stearic acid, or of naturally occurring fatty acid mixtures, which can be obtained, for example, from coconut oil or tallow oil. The fatty acid methyl-taurine salts are also suitable.

More frequently, however, so-called synthetic surfactants are used, in particular fatty alcohol sulfonates, fatty alcohol sulfates, sulfonated benzimidazole derivatives or alkylarylsulfonates.

The fatty alcohol sulfonates or sulfates are as a rule in the form of alkali metal, alkaline earth metal or substituted or unsubstituted ammonium salts and have an alkyl radical having 8 to 22 C atoms, alkyl also including the alkyl moiety of acyl radicals, for example the Na or Ca salt of ligninsulfonic acid, of sulfuric acid dodecyl ester or of a fatty alcohol sulfate mixture prepared from naturally occurring fatty acids. These also include the salts of sulfuric acid esters and sulfonic acids of fatty alcohol-ethylene oxide adducts. The sulfonated benzimidazole derivatives preferably contain 2 sulfonic acid groups and a fatty acid radical having 8–22 C atoms. Alkylarylsulfonates are, for example, the Na, Ca or triethanolamine salts of dodecylbenzenesulfonic acid, of dibutylnaphthalenesulfonic acid or of a naphthalenesulfonic acid-formaldehyde condensation product.

Corresponding phosphates, for example salts of the phosphoric acid ester of a p-nonylphenol-(4–14)-ethylene oxide adduct, or phospholipids are also suitable.

Nonionic surfactants are in particular polyglycol ether derivatives of aliphatic or cycloaliphatic alcohols, saturated or unsaturated fatty acids and alkylphenols and can contain 3 to 30 glycol ether groups and 8 to 20 carbon atoms in the (aliphatic) hydrocarbon radical and 6 to 18 carbon atoms in the alkyl radical of alkylphenols.

Other suitable nonionic surfactants are the water-soluble adducts, containing 20 to 250 ethylene glycol ether groups and 10 to 100 propylene glycol ether groups, of polyethylene oxide on polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit.

Examples of nonionic surfactants are nonylphenolpolyethoxyethanols, castor oil polyglycol ethers, polypropylene-polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, are also suitable.

The cationic surfactants are in particular quaternary ammonium salts which contain at least one alkyl radical having 8 to 22 C atoms as the substituent on N and contain lower, non-halogenated or halogenated alkyl, benzyl or lower hydroxyalkyl radicals as further substituents. The salts are preferably in the form of halides, methyl sulfates or ethyl sulfates, for example stearyltrimethylammonium chloride or benzyldi(2-chloroethyl)ethylammonium bromide.

The surfactants conventionally used in the art of formulation which can also be used in the compositions according to the invention are described, inter alia, in "McCutcheon's Detergents and Emulsifiers Annual" MC Publishing Corp., Ridgewood N.J., 1981, Stache, H., "Tensid-Taschenbuch" [Surfactant Handbook], Carl Hanser Verlag, Munich/Vienna, 1981 and M. and J. Ash, "Encyclopedia of Surfactants", Volume I–III, Chemical Publishing Co., New York, 1980–81.

The herbicidal formulations as a rule comprise 0.1 to 99%, in particular 0.1 to 95%, of active ingredient of the formula I, 1 to 99.9% of a solid or liquid formulation auxiliary and 0 to 25%, in particular 0.8 to 25%, of a surfactant.

While concentrated compositions tend to be preferred as the commercial product, the end user as a rule uses dilute compositions.

The compositions can also comprise other additives, such as stablizers, for example non-epoxidized or epoxidized vegetable oils (epoxidized coconut oil, rapeseed oil or soya oil), defoamers, for example silicone oil, preservatives, viscosity regulators, binders, tackifiers and fertilizers or other active ingredients.

In particular, preferred formulations have the following composition: (% percent by weight)
Emulsifiable Concentrates
Active ingredient: 1 to 90%, preferably 5 to 50%
Surface-active agent: 5 to 30%, preferably 10 to 20%
Solvent: 15 to 94 otepreferably 70 to 85%
Dusts
Active ingredient: 0. 1 to 50%, preferably 0.1 to 1%
Solid carrier: 99.9 to 90%, preferably 99.9 to 99%
Suspension Concentrates
Active ingredient: 5 to 75%, preferably 10 to 50%
Water: 94 to 24%, preferably 88 to 30%
Surface-active agent: 1 to 40%, preferably 2 to 30%
Wettable Powders
Active ingredient: 0.5 to 90%,preferably 1 to 80%
Surface-active agent: 0.5 to 20%,preferably 1 to 15%
Solid carrier: 5 to 95%, preferably 15 to 90%
Granules
Active ingredient: 0.1 to 30%, preferably 0.1 to 15%
Solid carrier: 99.5 to 70%, preferably 97 to 85%

The active ingredients of the formula I are as a rule employed successfully on plants or their environment with rates of application of 0.001 to 2 kg/ha, in particular 0.005 to 1 kg/ha. The dosage required for the desired action can be determined by experiments. It depends on the nature of the action, the stage of development of the crop plants and of the weeds and on the application (location, time, method), and can vary within wide limits as a result of these parameters.

The compounds of the formula I have herbicidal and growth-inhibiting properties which enable them to be used in crops of useful plants, in particular cereals, cotton, soya, sugar beet, sugar cane, plantations, oil seed rape, maize and rice.

Crops are also to be understood as meaning those which have been rendered tolerant to herbicides or classes of herbicides by conventional breeding or genetic manipulation methods.

The following examples illustrate the invention in more detail without limiting it.

Preparation Examples

EXAMPLE H1

4-Chloro-5-(4-chloro-2-fluoro-5-methoxy-phenyl)-2-methyl-2H-pyrazole-3-carbonitrle

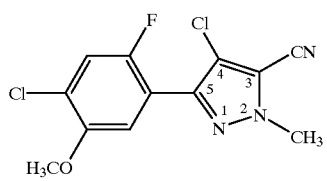

(6.009)

6.1 g of methyl 4-chloro-5-(4-chloro-2-fluoro-5-methoxy-phenyl)-2-methyl-2H-pyrazole-3-carboxylate is dissolved in 40 ml of xylene at room temperature in a dry apparatus under $N_2$ as an inert gas. 31 ml of dimethylaluminium amide solution (($CH_3$)$_2$AlNH$_2$ solution) in methylene chloride/n-hexane, prepared in accordance with J. L. Wood, N. A. Khatri and S. M. Weinreb, Tetrahedron Lett. 51, 4907 (1979), are added, while stirring (severe evolution of gas). After the reaction mixture has been subsequently stirred, it is slowly heated up to a temperature of 110° C. with the aid of an oil bath, and stirring is continued under gentle reflux overnight. The reaction mixture is then poured carefully onto ice-water and extracted with ethyl acetate. The organic phase is washed with saturated sodium chloride solution, dried over sodium sulfate and concentrated in vacuo. The crude product is applied from ethyl acetate onto silica gel 60 (Merck) and eluted on a flash chromatography column with toluene/n-hexane 4/1. The desired product is obtained in a yield of 3.3 g as a white solid of melting point 156–158° C.

EXAMPLE H2

Methyl 4chloro-5-(4-chloro-2-fluoro-phenyl)-2-methyl-2H-Pyrazole-3-carboxylate

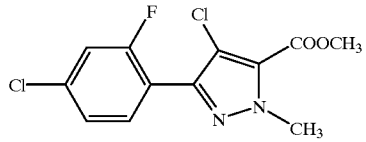

17.0 g of crude methyl 5-(4-chloro-2-fluoro-phenyl)-2-methyl-2H-pyrazole-3-carboxylate are dissolved in 85 ml of glacial acetic acid at room temperature, and chlorine gas is passed slowly over the yellow solution, while stirring (slightly exothermic reaction). A suspension gradually forms. TLC analysis on silica gel 60 $F_{254}$ (Merck) of a worked-up sample with n-hexane/ethyl acetate 4/1 as the eluent shows that starting material is still present after 1 hour. 10.0 g of anhydrous sodium acetate are added all at once and stirring is continued. Chlorine gas is passed over the suspension for a further hour. According to TLC analysis, no further starting material is present. The glacial acetic acid is removed on a rotary, evaporator, methylene chloride and 30 g of silica gel are added to the residue and the mixture is concentrated again on a rotary evaporator. The resulting mixture is applied to a flash silica gel column and chromatographed with n-hexane/ethyl acetate 7/1, 5/1 and finally 1/1. After evaporation of the relevant fractions, a solid is obtained and is digested with an n-hexane/ethyl acetate mixture. After the solid has been filtered off with suction and washed, 12.1 g of a white solid are obtained;

$^1$H-NMR (CDCl$_3$, 300 MHz): 7.50–7.40 ppm (m, 1H), 7.30–7.15 ppm (m, 2H), 4.22 ppm (s, 3H), 3.98 ppm (s, 3

EXAMPLE H3

Methyl 4-chloro-5-(4-chloro-2-fluoro-5-nitro-phenyl)-2-methyl-2H-pyrazole-3-carboxylate

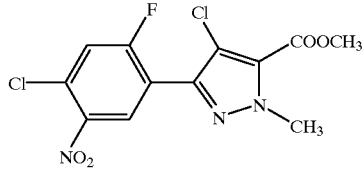

4.1 g of methyl 4-chloro-5-(4-chloro-2-fluoro-phenyl)-2-methyl-2H-pyrazole-3-carboxylate (Example H2) are added to 1.8 ml of concentrated sulfuric acid under $N_2$ as an inert gas, while cooling in an ice bath. Nitrating acid (prepared from 1.4 ml of 65% aqueous nitric acid and 1.6 ml of concentrated sulfuric acid) is then added, while cooling in an ice bath. In the course of the addition, the viscous reaction mixture becomes stirrable (magnetic stirrer). It is subsequently stirred at room temperature for 30 minutes. 2.5 times the amount of nitrating acid added above is added in 3 portions in the course of 3 hours. For the addition, the mixture is always precooled in an ice bath and then subsequently stirred while warming to room temperature. TLC analysis on silica gel 60 $F_{254}$ (Merck) of a worked-up sample using n-hexane/ethyl acetate 5/1 as the eluent shows that all the starting material has reacted. Ice-water is carefully added to the viscous orange-coloured reaction mixture, the resulting mixture is stirred and a little diethyl ether is poured over. The solid formed is filtered off with suction and digested several times with n-hexane/diethyl ether 10/1 and sucked dry. The solid thus obtained is dried overnight at 50° C. in a vacuum drying cabinet. The desired product is obtained;

$^1$H-NMR (d$_6$-DMSO, 300 MHz): 8.33 ppm (d,1H), 8.07 ppm (d, 1H), 4.17 ppm (s, 3H), 3.91 ppm (s, 3H).

EXAMPLE H4

1-(4-Chloro-2-fluoro-phenyl)-ethanone (43.023)

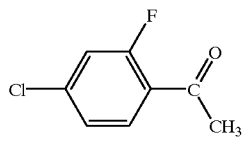

326 g of 4-chloro-2-fluoro-benzoyl chloride are dissolved in 250 ml of dry toluene=solution A. 112.5 g of anhydrous magnesium chloride are suspended in 1.4 1 of dry toluene. While stirring, first 566 ml of triethylamine, then 233 ml of dimethyl malonate (in portions) are added. After the first addition of dimethyl malonate, after an induction period of several minutes, an exothermic reaction occurs. The temperature is kept at about 25° C. by cooling with an ice bath. After the addition, the mixture is subsequently stirred at room temperature for 2 hours. Thereafter, the prepared solution A is added dropwise at room temperature in the course of 90 minutes and the reaction mixture is then subsequently stirred for 1 hour. It is then cooled in an ice bath and 12 mol of hydrochloric acid (300 ml) are added. After dilution with ice-water, the reaction mixture is extracted by shaking and the organic phase is washed with dilute hydrochloric acid and then with brine, dried over sodium sulfate, filtered and evaporated to dryness in vacuo. The resulting yellow oil is diluted with 200 ml of dimethyl sulfoxide and slowly added dropwise to a thoroughly stirred mixture, heated under gentle reflux (oil bath temperature 140° C.), of 60 ml of water and 1400 ml of dimethyl sulfoxide (evolution of gas). After the addition, the mixture is subsequently stirred under gentle reflux for 2 hours. After cooling to room temperature, it is poured onto ice-water and extracted with diethyl ether. The ether phase is washed with water, dried over sodium sulfate and concentrated to dryness in vacuo. Distillation under a high vacuum gives 255 g of a colourless liquid of boiling point 52° C./0.15 mbar.

EXAMPLE H5

1-Chloro-5-fluoro-4-iodo-2-isopropoxy-benzene

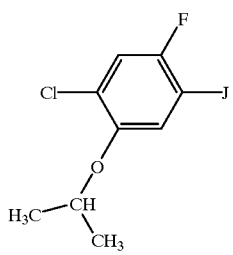

300 g of crude 4-chloro-2-fluoro-5-isopropoxy-phenylamine is initially introduced into the reaction vessel together with 1 1 of water. 1 1 of an approximately 12 molar aqueous hydrochloric acid solution is added dropwise, while stirring and cooling with a dry ice/ethanol cooling bath. A thick but stirrable slurry is thereby formed. A solution of 109 g of sodium nitrite in 250 ml of water is added dropwise at a temperature of less than 5° C. in the course of 40 minutes, while stirring and cooling, and the reaction mixture is subsequently stirred below a temperature of 2° C. for 30 minutes. Thereafter, a solution of 259 g of potassium iodide in 350 ml of water is added dropwise in the course of 45 minutes, while stirring, the temperature being kept below 5° C. (evolution of gas). The emulsion formed is extracted with diethyl ether and the ether phase is washed with sodium disulfite solution ($Na_2S_2O_5$ solution) and then with brine. After drying over sodium sulfate, the ether phase is concentrated and the resulting oil is distilled under a high vacuum under 0.03 mbar. The fraction with a boiling point of 84° C. is collected, 268 g of the desired compound being obtained in the form of a yellow oil.

EXAMPLE H6

4-Chloro-2-fluoro-5-isopropoxy-benzoic acid

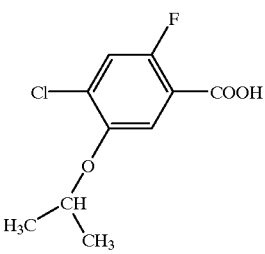

120 g of 1-chloro-5-fluoro-4-iodo-2-isopropoxybenzene (Example H5) are initially introduced into an autoclave together with 2.68 g of $PdCl_2(P(C_6H_5)_3)_2$, 35.4 g of calcium hydroxide, 540 ml of methanol and 18.9 ml of water. Carbon monoxide gas is then forced in up to a pressure of 150 bar at 22° C. The reaction mixture is kept at 100° C. for 12 hours, while stirring. Thereafter, it is cooled to room temperature and the pressure is released. The mixture is flushed out of the autoclave with methanol and concentrated on a rotary evaporator. The residue obtained is poured in portions into dilute and cooled hydrochloric acid and then extracted with diethyl ether. After the ether phase has been washed with brine, it is dried over sodium sulfate and concentrated to dryness. 67.4 g of a slightly brown solid are obtained; melting point 132–137° C.

EXAMPLE H7

1-(4-Chloro-2-fluoro-5-isopropoxyphenyl)-4,4-diethoxy-butane-1,3-dione

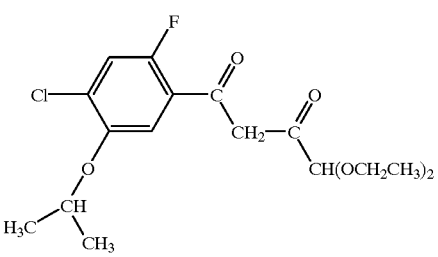

12.0 g of 4-chloro-2-fluoro-5-isopropoxy-acetophenone are dissolved in dry diethyl ether together with 11.0 g of ethyl diethoxyacetate, while cooling with ice. 29 ml of a 21% solution of sodium ethanolate in ethanol are added dropwise, while stirring vigorously, the temperature being kept below 5° C. The ice bath is then removed and replaced by an oil bath. The reaction mixture is subsequently stirred overnight while heating under gentle reflux. The mixture is then cooled to room temperature and diluted with ethyl acetate. An excess of 1 molar hydrochloric acid is added, while stirring and cooling in an ice bath. After extraction by shaking and separation of the phases, the organic phase is washed with water and then dried over sodium sulfate, filtered and evaporated. The resulting solid residue can be used directly for the next reaction stage.

EXAMPLE H8

3-(4-Chloro-2-fluoro-5-isopropoxy-phenyl)-5-diethoxymethyl-1H-pyrazole

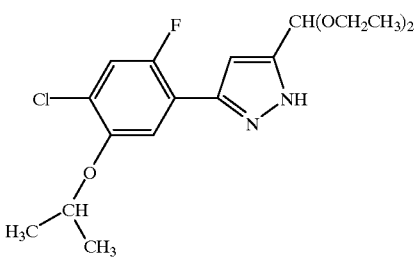

The crude 1-(4-chloro-2-fluoro-5-isopropoxy-phenyl)-4,4-diethoxybutane-1,3-dione (Example H7) is initially introduced into 150 ml of dry ethanol. 2.90 g of hydrazine monohydrate are added dropwise at room temperature, while stirring. The mixture is then stirred for 4 hours, while heating under gentle reflux, and is subsequently cooled and the alcohol is removed on a rotary evaporator in vacuo. The residue obtained is partitioned between aqueous sodium bicarbonate solution and ethyl acetate. After extraction by shaking and separation of the phases, the organic phase is washed with water and then dried over sodium sulfate and concentrated. 17.5 g of a dark yellow oil are obtained.

$^1$H-NMR (CDCl$_3$, 300 MHz): 7.48 ppm (d, 1H), 7.19 ppm (d, 1H), 6.72 ppm (d, 1H), 5.70 ppm (s, 1H), 4.55 ppm (septet, 1H), 3.75–3.55 ppm (m, 4H), 1.36 ppm (d, 6H), 1.29–1.23 ppm (t, 6H).

EXAMPLE H9

Methyl 4-(4-chloro-2-fluoro-5-isopropoxy-phenyl)-2,4-dioxo-butyrate (39.026)

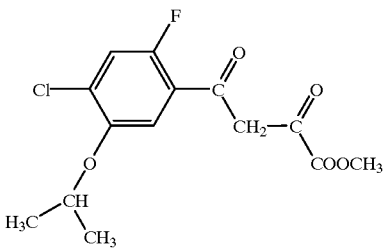

31.5 g of 1-(4-chloro-2-fluoro-5-isopropoxy-phenyl)-ethanone are dissolved in 300 ml of dry diethyl ether. After cooling in an ice bath, 19.3 g of dimethyl oxalate are added dropwise. 38 ml of a 5.4 molar solution of sodium methylate in methanol are added dropwise at 0–5° C. in the course of 40 minutes, while stirring. The mixture is subsequently stirred at the stated temperature for 2 hours. The orange-brown suspension is acidified with dilute hydrochloric acid and diluted with ethyl acetate. After separation of the phases, the organic phase is washed with brine, dried over sodium sulfate, filtered and concentrated. After drying in a vacuum drying cabinet, 42.3 g of an orange to brown solid, which can be employed directly for the next reaction stage, are obtained.

EXAMPLE H10

Methyl 5-(4-chloro-2-fluoro-5-isopropoxy-phenyl)-2H-pyrazolecarboxylate

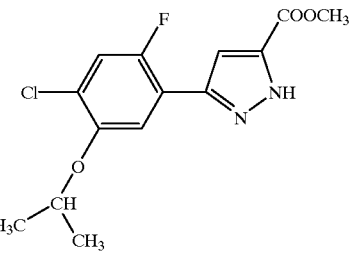

42.3 g of crude methyl 4-(4-chloro-2-fluoro-5-isopropoxy-phenyl)-2,4-dioxo-butyrate (Example H9) are added to a solution of 8.5 ml of hydrazine monohydrate in 150 ml of glacial acetic acid at room temperature. The mixture is then stirred at an oil bath temperature of 100° C. for 2 hours. TLC analysis (silica gel 60 F$_{254}$; eluent n-hexane/ethyl acetate 1/1) of a worked-up sample shows that all the starting material has reacted. The glacial acetic acid is removed on a rotary evaporator and the residue obtained is partitioned between dilute hydrochloric acid and diethyl ether. After separation of the phases, the ether phase is rinsed with dilute hydrochloric acid. A beige solid precipitates out during this operation, and is filtered off and washed with water and diethyl ether. After the aqueous phase has been removed and the ether phase has been rinsed with brine, it is dried over sodium sulfate, filtered and concentrated. The solid obtained is combined with the material on the suction filter and digested with a mixture of n-hexane/ethyl acetate 10/1. The suspension is filtered with suction and the product is washed. After drying in a vacuum drying cabinet at 40° C., 30.3 g of the desired compound are obtained.

$^1$H-NMR (d6-DMSO, 300 MHz): 14.45–13.90 ppm (broad signal, 1H), 7.64 ppm (d, 1H), 7.57 ppm (d, 1H), 7.14 ppm (d, 1H), 4.72 ppm (m, 1H), 3.85 ppm (s, 3H), 1.31 ppm (d, 6H).

EXAMPLE H11

3-(4-Chloro-2-fluoro-5-isopropoxy-phenyl)-5-diethoxymethyl-1-methyl-1H-pyrazole (37.009)

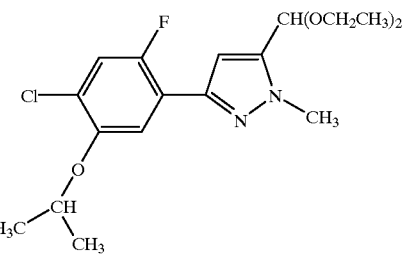

17.5 g of 3-(4-chloro-2-fluoro-5-isopropoxy-phenyl)-5-diethoxymethyl-1H-pyrazole (Example H8) are dissolved in 65 ml of dry N-methylpyrrolidone (NMP), and 20.4 g of potassium carbonate are added. The mixture is heated to 50°

C., while stirring, and a solution of 3.70 ml of methyl iodide in 10 ml of dry NMP is slowly added dropwise. The mixture is subsequently stirred overnight at 50° C. and cooled to room temperature on the following day. It is partitioned between water and diethyl ether. The ether phase is washed several times with water, dried over sodium sulfate and evaporated. Purification of the resulting crude product by means of flash chromatography and n-hexane/ethyl acetate 5/1 and 4/1 as the eluent gives 12.1 g of a yellow oil, which slowly crystallizes out when left to stand.

$^1$H-NMR (CDCl$_3$, 300 MHz): 7.58 ppm (d, 1H), 7.15 ppm (d, 1H), 6.73 ppm (d, 1H), 5.58 ppm (s, 1H), 4.61 ppm (m, 1H), 3.95 ppm (s, 3H), 3.75–3.50 ppm (m, 4H), 1.38 (d, 6H).

EXAMPLE H12

Methyl 5-(4-chloro-2-fluoro-5-isopropoxy-phenyl)-2-methyl-2H-pyrazole-carboxylate

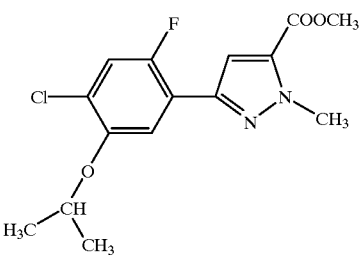

30.3 g of methyl 5-(4-chloro-2-fluoro-5-isopropoxy-phenyl)-2H-pyrazole-carboxylate (Example 10) and 40.2 g of potassium carbonate are suspended in 100 ml of dry N-methylpyrrolidone (NMP). A solution of 9.1 ml of methyl iodide in 10 ml of NMP is added dropwise at a temperature of 55° C., while stirring (slightly exothermic reaction). The suspension formed is stirred at 55° C. for 2.5 hours. TLC analysis (silica gel 60 F$_{254}$, n-hexane/ethyl acetate 1/1) of a sample shows complete conversion of the starting material. The mixture is poured onto ice-water and extracted with diethyl ether. The ether phase is washed with brine, dried over sodium sulfate and filtered. 60 g of silica gel are added to the ether solution and the mixture is evaporated to dryness. After application of the silica gel-product mixture to a flash chromatography column, the column is eluted with n-hexane/ethyl acetate 8/1, 5/1 and 1/1. 9.1 g of the desired compound are obtained as a solid;

$^1$H-NMR (d$_6$-DMSO, 300 MHz): 7.60–7.50 ppm (m, 2H), 7.20 ppm (d, 1H), 4.67 ppm (m, 1H), 4.17 ppm (s, 3H), 3.87 ppm (s, 3H), 1.31 ppm (d, 6H).

The isomeric methyl 5-(4-chloro-2-fluoro-5-isopropoxy-phenyl)-1-methyl-1H-pyrazole-carboxylate of the formula

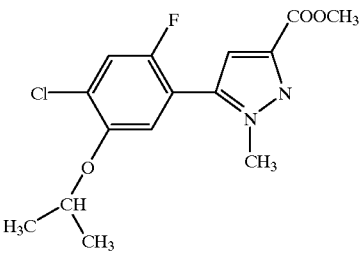

can be obtained as a by-product from subsequent fractions of the flash chromatography;

$^1$H-NMR (d6-DMSO, 300 MHz): 7.65 ppm (d, 1H), 7.34 ppm (d, 1H), 6.96 ppm (s, 1H), 4.72 ppm (m, 1H), 3.85 ppm (s, 3H), 3.80 ppm (s, 3H), 1.28 ppm (d, 6H).

EXAMPLE H13

Methyl 4-chloro-5-(4-chloro-2-fluoro-phenyl)-2-methyl-2H-pyrazole-3-carboxylate

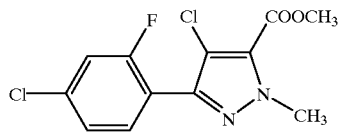

17.0 g of crude methyl 5-(4-chloro-2-fluoro-phenyl)-2-methyl-2H-pyrazole-3-carboxylate are dissolved in 85 ml of glacial acetic acid at room temperature. Chlorine gas is slowly passed over the yellow solution, while stirring. A slight heat effect is detectable. A suspension gradually forms. TLC analysis (silica gel 60 F$_{254}$ (Merck), n-hexane/ethyl acetate 4/1) of a worked-up sample shows that the starting material is still present after 1 hour. 10.0 g of anhydrous sodium acetate are added all at once and stirring is continued. Chlorine gas is passed over the suspension for a further hour. According to TLC analysis, no further starting material is present. The glacial acetic acid is removed on a rotary evaporator, methylene chloride and 30 g of silica gel are added to the residue obtained and the mixture is evaporated on a rotary evaporator. The resulting mixture is chromatographed on a flash chromatography column with n-hexane/ethyl acetate 7/1, 5/1 and 1/1. A precipitate is obtained, and is digested with an n-hexane/diethyl ether mixture. After the solid component has been filtered off with suction and washed, 12.1 g of a white solid are obtained;

$^1$H-NMR (CDCl$_3$, 300 MHz): 7.50–7.40 ppm (m, 1H), 7.30–7.15 ppm (m, 2H), 4.22 ppm (s, 3H), 3.98 ppm (s, 3H).

EXAMPLE H14

Methyl 4-chloro-5-(4-chloro-2-fluoro-5-nitro-phenyl)-2-methyl-2H-pyrazole-3-carboxylate

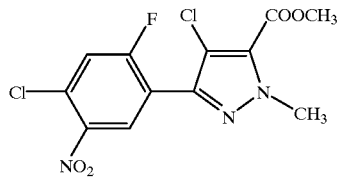

4.1 g of methyl 4-chloro-5-(4-chloro-2-fluoro-phenyl)-2-methyl-2H-pyrazole-3-carboxylate (Example H13) are added to 1.8 ml of concentrated sulfuric acid under N$_2$ as an inert gas, while cooling in an ice bath. Nitrating acid (prepared from 1.4 ml of 65% aqueous nitric acid and 1.6 ml of concentrated sulfuric acid) is then added, while cooling in an ice bath. In the course of the addition, the reaction mixture becomes stirrable (magnetic stirrer). Stirring is continued at room temperature for 30 minutes. 2.5 times the amount of the nitrating acid added above is added again in 3 portions in the course of 3 hours. For the addition of the nitrating acid, the mixture is always precooled in an ice bath and then subsequently stirred while warming up to room temperature. TLC analysis (silica gel 60 F$_{254}$ (Merck), n-hexane/ethyl acetate 5/1) on a worked-up sample shows that all the starting material has reacted. Ice-water is carefully added to the viscous reaction mixture. The resulting mixture is stirred, and a little diethyl ether is poured over. The solid is filtered off with suction, digested several times with n-hexane/diethyl ether 10/1 on the suction filter and sucked dry. The solid obtained is dried overnight at 50° C. in a vacuum drying cabinet. 4.4 g of a solid are obtained;

$^1$H-NMR (d$_6$-DMSO, 300 MHz): 8.33 ppm (d, 1H), 8.07 ppm (d, 1H), 4.17 ppm (s, 3H), 3.91 ppm (s, 3H).

EXAMPLE H15

Methyl 4-chloro-5-(5-amino-4-chloro-2-fluoro-phenyl)-2-methyl-2H-pyrazole-3-carboxylate

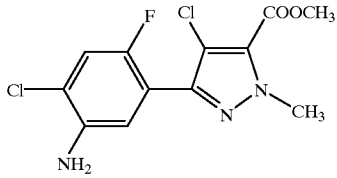

5.88 g of methyl 4-chloro-5-(4-chloro-2-fluoro-5-nitro-phenyl)-2-methyl-2H-pyrazole-3-carboxylate (Example H14) are suspended in 100 ml of glacial acetic acid. The mixture is heated up with the aid of an oil bath (oil bath temperature 100° C.), while stirring. 3.76 g of iron powder are slowly introduced and the mixture is then subsequently stirred at an oil bath temperature of 100° C. for 1 hour. TLC analysis (silica gel 60 F$_{254}$, n-hexane/ethyl acetate 5/2) of a worked-up sample shows that the starting material is no longer present. After cooling to room temperature, the glacial acetic acid is evaporated off on a vacuum rotary evaporator and the resulting residue is partitioned between ethyl acetate and water. After separation of the phases, the organic phase is washed with brine, dried over sodium sulfate, filtered and evaporated to dryness. The brown oil is subjected to addition of carbon tetrachloride and evaporation in vacuo several times. The resulting crude product can be used directly for the next reaction stage (Example H16).

EXAMPLE H16

Methyl 4-chloro-5-(4-chloro-2-fluoro-5-iodo-phenyl)-2-methyl-2H-pyrazole-3-carboxylate

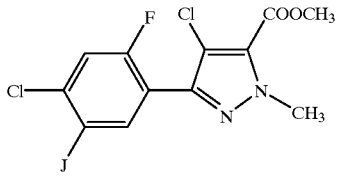

4.3 g of crude methyl 4-chloro-5-(5-amino-4-chloro-2-fluoro-phenyl)-2-methyl-2H-pyrazole-3-carboxylate (Example H15) are introduced into a solution of 25 ml of 12 molar hydrochloric acid in 25 ml of water. The mixture is brought to a temperature of 0–5° C., while stirring, and 1.0 g of sodium nitrite is added at this temperature. The mixture is subsequently stirred for 50 minutes. A solution of 2.37 g of potassium iodide in 2.5 ml of water is then added dropwise in the stated temperature range. After 30 minutes, ice-water is added to the reaction mixture. The aqueous phase is extracted with ethyl acetate and the organic phase is treated with an aqueous sodium disulfite solution (Na$_2$S$_2$O$_5$ solution) and then washed with brine. After drying over sodium sulfate, the organic phase is filtered off, 10 g of silica gel are added and the mixture is evaporated to dryness. After application of this silica gel-product mixture to a flash chromatography column, the column is eluted with n-hexane/ethyl acetate 20/1 and then 10/1. The relevant fractions are combined and evaporated. The residue can be prepared in a pure form by digestion in n-hexane. After filtration with suction and washing with n-hexane, the product is dried in vacuo. Yield of 3.3 g of a white solid of melting point 160–161.5° C.

EXAMPLE H17

4-Chloro-5-(4-chloro-2-fluoro-5-isopropoxy-phenyl)-2-methyl-2H-pyrazole-3-carbaldehyde (34.007)

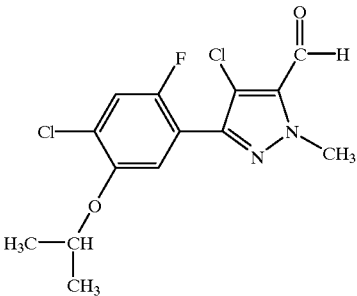

3.00 g of 3-(4-chloro-2-fluoro-5-isopropoxy-phenyl)-5-diethoxymethyl-1-methyl-1H-pyrazole (Example H11) are dissolved in 10 ml of glacial acetic acid at room temperature. Chlorine gas is passed over the solution, while stirring, until TLC analysis (silica gel 60 F$_{254}$, n-hexane/ethyl acetate 4/1) of a worked-up sample shows that the starting material is no longer present. The glacial acetic acid is evaporated off in vacuo and the resulting residue is partitioned between dilute aqueous sodium hydroxide solution and diethyl ether. After the phases have been separated, the organic phase is washed with brine, dried over sodium sulfate, filtered and concentrated. Preparation of the product in a pure form over a flash chromatography column with petroleum ether/ethyl acetate 6/1 gives 1.70 g of a yellow oil;

$^1$H-NMR (d$_6$-DMSO, 300 MHz): 9.98 ppm (s, 1H), 7.63 ppm (d, 1H), 7.25 ppm (d, 1H), 4.66 ppm (m, 1H), 4.17 ppm (s, 3H).

EXAMPLE H18

1-[4-Chloro-5-(4-chloro-2-fluoro-5-isopropoxy-phenyl)-2-methyl-2H-pyrazol-3-yl]-ethanol

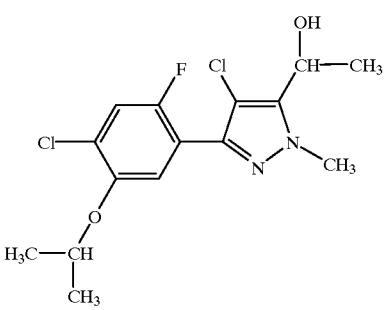

32.0 g of 4-chloro-5-(4-chloro-2-fluoro-5-isopropoxy-phenyl)-2-methyl-2H-pyrazole-3-carbaldehyde (Example H17) are dissolved in 100 ml of dry diethyl ether and the solution is added dropwise in the course of 45 minutes, while stirring, to a 22% solution of CH$_3$MgCl in tetrahydrofuran, which has been initially introduced into the reaction vessel. During this operation, the temperature rises to 40° C. The mixture is subsequently stirred at 40° C. for 90 minutes. After cooling to room temperature, it is poured onto ice-water and rendered acid with 2 molar hydrochloric acid. After extraction by shaking and separation of the phases, the organic phase is washed first with water, then with dilute aqueous sodium bicarbonate solution and then with brine. After drying over sodium sulfate, the mixture is filtered and the filtrate is concentrated in vacuo. Preparation of the pure product by means of a flash chromatography column and n-hexane/ethyl acetate 2/1 gives 18.4 g of the title compound as a yellow oil;

$^1$H-NMR ($d_6$-DMSO, 300 MHz): 7.54 ppm (d, 1H), 7.16 ppm (d, 1H), 5.73 ppm (broad signal, 1H), 5.02 ppm (m, 1H), 4.63 ppm (m, 1H), 3.97 ppm (s, 3H), 1.46 ppm (d, 3H), 1.28 ppm (d, 6H).

EXAMPLE H19

1-[4-Chloro-5-(4-chloro-2-fluoro-5-isopropoxyphenyl)-2-methyl-2H-pyrazol-3-yl]-ethanone

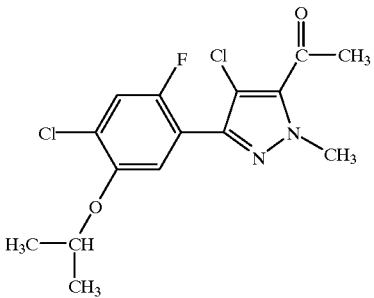

7.0 g of 1-[4-chloro-5-(4-chloro-2-fluoro-5-isopropoxyphenyl)-2-methyl-2H-pyrazol-3-yl]-ethanol (Example H18) are dissolved in 10 ml of methylene chloride and the solution is added dropwise to 6.5 g of pyridinium chlorochromate in 17 ml of methylene chloride at room temperature, while stirring. The mixture is subsequently stirred at this temperature for 3 hours. The black reaction mixture is then filtered over Hyflo Super Cel. After the material on the suction filter has been washed with methylene chloride, the combined organic phases are washed successively with water, aqueous sodium bicarbonate solution, aqueous ammonium chloride solution and brine. The organic phase is then dried over sodium sulfate, filtered and evaporated to dryness in vacuo. 5.62 g of the title compound is obtained in the form of a dark brown oil.

1H-NMR ($d_6$-DMSO, 300 MHz): 7.61 ppm (d, 1H), 7.21 ppm (d, 1H), 4.65 ppm (m, 1H), 4.08 ppm (s, 3H), 2.65 ppm (s, 3H), 1.28 ppm (d, 6H).

The compounds listed in the following tables can also be prepared in an analogous manner or by means of known methods:

TABLE 1

Compounds of the formula Ia

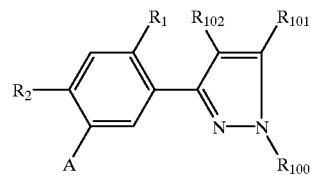

(Ia)

| Compound No. | $R_1$ | $R_2$ | $R_{100}$ | $R_{101}$ | $R_{102}$ | A | Physical data |
|---|---|---|---|---|---|---|---|
| 1.001 | H | Cl | $CH_3$ | CN | Cl | $CH_3$ | |
| 1.002 | H | Cl | $CH_3$ | CN | Cl | $CH_2Br$ | |
| 1.003 | H | Cl | $CH_3$ | —$CSNH_2$ | Cl | $CH_3$ | |
| 1.004 | H | Cl | $CH_3$ | CN | Cl | $CHBr_2$ | |
| 1.005 | F | Cl | $CH_3$ | CN | Cl | $CH_3$ | |
| 1.006 | F | Cl | $CH_3$ | CN | Cl | $CH_2Br$ | |
| 1.007 | F | Cl | $CH_3$ | —$CSNH_2$ | Cl | $CH_3$ | |
| 1.008 | F | Cl | $CH_3$ | CN | Cl | $C_6H_5$ | resin |
| 1.009 | F | Cl | $CH_3$ | —$CSNH_2$ | Cl | ![oxazoline] | |
| 1.010 | F | Cl | $CH_3$ | CN | Cl | ![methyl-oxazoline] | |

TABLE 1-continued

Compounds of the formula Ia

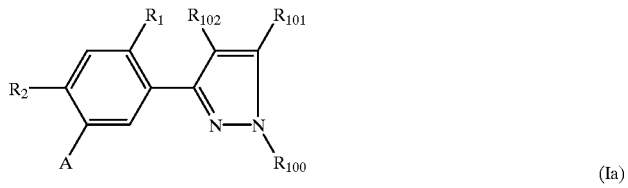

| Compound No. | $R_1$ | $R_2$ | $R_{100}$ | $R_{101}$ | $R_{102}$ | A | Physical data |
|---|---|---|---|---|---|---|---|
| 1.011 | F | Cl | $CH_3$ | CN | Cl | 2-methyl-4-ethyl-4,5-dihydrooxazole | |
| 1.012 | F | Cl | $CH_3$ | CN | Cl | 2-methyl-5-methyl-4,5-dihydrooxazole | |
| 1.013 | F | Cl | $CH_3$ | CN | Cl | 2-methyl-4,5-dihydrothiazole | |
| 1.014 | F | Cl | $CH_3$ | CN | Cl | —$CH_2$—OH | |
| 1.015 | F | Cl | $CH_3$ | CN | Cl | —$CH_2$—Cl | |
| 1.016 | F | Cl | $CH_3$ | CN | Cl | —$CH_2$—COOH | |
| 1.017 | F | Cl | $CH_3$ | CN | Cl | —$CH_2$—COO$CH_2$$CH_3$ | |
| 1.018 | F | Cl | $CH_3$ | CN | Cl | —$CH_2$—O—$CH_2$—$CH_3$ | |
| 1.019 | F | Cl | $CH_3$ | CN | Cl | —$CH_2$—S—CH($CH_3$)$_2$ | |
| 1.020 | F | Cl | $CH_3$ | CN | Cl | —($CH_2$)$_5$$CH_3$ | |
| 1.021 | F | Cl | $CH_3$ | CN | Cl | —$CH_2$—CH=$CH_2$ | m.p. 68–69° C. |
| 1.022 | F | Cl | $CH_3$ | CN | Cl | —C≡C—C($CH_3$)$_2$—OH | |
| 1.023 | F | Cl | $CH_3$ | CN | Cl | —C≡CH | |
| 1.024 | F | Cl | $CH_3$ | CN | Cl | —C≡C—$CH_2$—OH | m.p. 138–139° C. |
| 1.025 | F | Cl | $CH_3$ | CN | Cl | —$CH_2$—$CH_2$—COOH | |
| 1.026 | F | Cl | $CH_3$ | CN | Cl | —$CH_2$—$CH_2$—COO$CH_2$—$CH_3$ | |
| 1.027 | F | Cl | $CH_3$ | CN | Cl | —$CH_2$—CH(Cl)—COO$CH_2$$CH_3$ | resin |
| 1.028 | F | Cl | $CH_3$ | CN | Cl | —$CH_2$—CH(S$CH_3$)—COO$CH_2$—$CH_3$ | resin |
| 1.029 | F | Cl | $CH_3$ | CN | Cl | —CH=CH—COOH | |
| 1.030 | F | Cl | $CH_3$ | CN | Cl | —CH=CH—COO$CH_2$—$CH_3$ | m.p. 124–125° C. |
| 1.031 | F | Cl | $CH_3$ | CN | Cl | 3-(methoxycarbonyl)phenyl | |
| 1.032 | F | Cl | $CH_3$ | CN | Cl | H | m.p. 115–116° C. |
| 1.033 | Cl | Cl | $CH_3$ | CN | Cl | $CH_3$ | |
| 1.034 | H | Cl | $CH_3$ | CN | Cl | H | m.p. 146–150° C. |
| 1.035 | H | F | $CH_3$ | CN | Cl | H | m.p. 122–123° C. |
| 1.036 | F | F | $CH_3$ | CN | Cl | H | m.p. 113–114° C. |
| 1.037 | F | Cl | $CH_3$ | CN | F | H | |
| 1.038 | F | CN | $CH_3$ | CN | Cl | H | |
| 1.039 | F | $NO_2$ | $CH_3$ | CN | Cl | H | |
| 1.040 | F | $NH_2$ | $CH_3$ | CN | Cl | H | |
| 1.041 | F | Cl | $CH_3$ | —$CSNH_2$ | Cl | H | |
| 1.042 | F | OH | $CH_3$ | CN | Cl | H | |
| 1.043 | F | $OCH_3$ | $CH_3$ | CN | Cl | H | |
| 1.044 | F | $OCHF_2$ | $CH_3$ | CN | Cl | H | |
| 1.045 | F | Cl | $CH_3$ | CN | Br | $CH_2$CH(Cl)COO$CH_2$$CH_3$ | m.p. 72–75° C. |
| 1.046 | F | Cl | $CH_3$ | CN | Cl | NHOH | |
| 1.047 | F | Cl | $CH_3$ | CN | Br | NHOH | solid |
| 1.048 | F | Cl | $CH_3$ | CN | Cl | N(COCH$_3$)O(COCH$_3$) | |

TABLE 1-continued

Compounds of the formula Ia

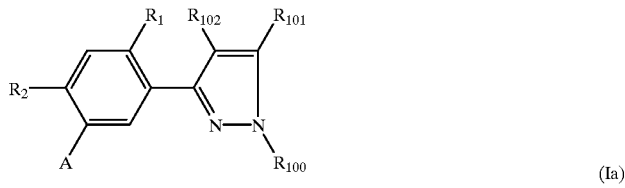

(Ia)

| Compound No. | R₁ | R₂ | R₁₀₀ | R₁₀₁ | R₁₀₂ | A | Physical data |
|---|---|---|---|---|---|---|---|
| 1.049 | F | Cl | CH₃ | CN | Cl | COOCH₂Si(CH₃)₃ | |
| 1.050 | F | Cl | CH₃ | CN | Cl | COOCH(CH₃)CH₂Si(CH₃)₃ | |
| 1.051 | F | Cl | CH₃ | CN | Cl | COOCH₂CH₂Si(CH₃)₃ | |
| 1.052 | Cl | Cl | CH₃ | CN | Cl | COOCH(CH₃)CH₂Si(CH₃)₃ | |
| 1.053 | F | Cl | CH₃ | CSNH₂ | Cl | COOCH(CH₃)CH₂Si(CH₃)₃ | |
| 1.054 | H | Cl | CH₃ | CN | Br | H | m.p. 136–145° C. |
| 1.055 | H | Cl | CHF₂ | CN | Cl | H | m.p. 90–91° C. |
| 1.056 | F | H | CH₃ | CN | Cl | F | |
| 1.057 | F | NO₂ | CH₃ | CN | Cl | F | |
| 1.058 | F | NO₂ | CH₃ | CN | Cl | OCH₃ | |
| 1.059 | F | NO₂ | CH₃ | CN | Cl | OH | |
| 1.060 | F | NH₂ | CH₃ | CN | Cl | OCH₃ | |
| 1.061 | F | H | CH₃ | CN | Br | F | |
| 1.062 | F | NO₂ | CH₃ | CN | Br | F | m.p. 144–146° C. |
| 1.063 | F | NO₂ | CH₃ | CN | Br | OCH₃ | m.p. 173–174° C. |
| 1.064 | F | NO₂ | CH₃ | CN | Br | OH | |
| 1.065 | F | NH₂ | CH₃ | CN | Br | OCH₃ | m.p. 158–161° C. |
| 1.066 | F | Cl | CH₃ | CN | F | H | |
| 1.067 | Cl | Cl | CH₃ | CN | F | H | m.p. 87–88° C. |
| 1.068 | F | Cl | CH₃ | CN | Br | H | m.p. 143–144° C. |

TABLE 2

Compounds of the formula Ib

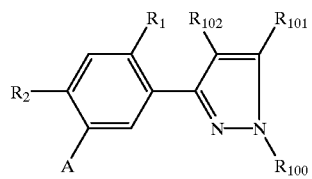

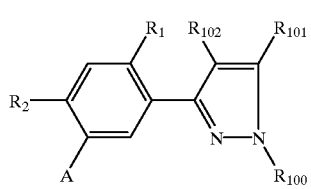

(Ib)

| Compound No. | R₁ | R₂ | R₁₀₀ | R₁₀₁ | R₁₀₂ | A | Physical data |
|---|---|---|---|---|---|---|---|
| 2.001 | H | Cl | CH₃ | CN | Cl | Cl | |
| 2.002 | H | F | CH₃ | CN | Cl | Cl | |
| 2.003 | H | F | CH₃ | CN | Cl | NO₂ | m.p. 142–143° C. |
| 2.004 | H | Cl | CH₃ | CN | Cl | I | m.p. 160–162° C. |
| 2.005 | F | Cl | CH₃ | CN | Cl | Br | m.p. 113–114° C. |
| 2.006 | F | Cl | CH₃ | CN | Cl | I | m.p. 125–126° C. |
| 2.007 | F | Cl | CH₃ | CN | Cl | NO₂ | m.p. 118–120° C. |
| 2.008 | F | Cl | CH₃ | CN | Cl | CN | |
| 2.009 | F | Cl | CH₃ | CN | Br | NO₂ | m.p. 139–140° C. |
| 2.010 | F | F | CH₃ | CN | Cl | Cl | |
| 2.011 | F | F | CH₃ | CN | Cl | NO₂ | |
| 2.012 | Cl | Cl | CH₃ | CN | Cl | NO₂ | resin |
| 2.013 | Cl | Cl | CH₃ | CN | Cl | Br | |
| 2.014 | Cl | Cl | CH₃ | CN | Cl | I | m.p. 120–122° C. |
| 2.015 | F | OH | CH₃ | CN | Cl | NO₂ | |
| 2.016 | F | OCH₃ | CH₃ | CN | Cl | NO₂ | |
| 2.017 | F | OCHF₂ | CH₃ | CN | Cl | NO₂ | |
| 2.018 | F | OCHF₂ | CH₃ | CN | Cl | NO₂ | |
| 2.019 | F | OH | CH₃ | CN | Cl | Br | |
| 2.020 | F | NO₂ | CH₃ | CN | Cl | F | |
| 2.021 | F | NO₂ | CH₃ | CN | Cl | Cl | |
| 2.022 | Cl | NO₂ | CH₃ | CN | Cl | F | |
| 2.023 | Cl | F | CH₃ | CN | Cl | NO₂ | |
| 2.024 | F | Br | CH₃ | CN | Cl | NO₂ | |
| 2.025 | F | Br | CH₃ | CN | Cl | I | |
| 2.026 | F | Br | CH₃ | CN | Cl | CN | |
| 2.027 | F | CN | CH₃ | CN | Cl | CN | |
| 2.028 | F | CN | CH₃ | CN | Cl | Br | |
| 2.029 | F | NO₂ | CH₃ | CN | Br | F | m.p. 144–145° C. |
| 2.030 | F | H | CH₃ | CN | Br | F | m.p. 92–93° C. |
| 2.031 | F | H | CH₃ | CN | Cl | F | |
| 2.032 | F | H | CH₃ | CN | Cl | Cl | |
| 2.033 | F | Cl | CH₃ | CSNH₂ | Cl | I | |
| 2.034 | F | Cl | CH₃ | CSNH₂ | Cl | Br | |
| 2.035 | F | F | CH₃ | CSNH₂ | Cl | NO₂ | |
| 2.036 | F | NO₂ | CH₃ | CSNH₂ | Cl | F | |
| 2.037 | F | NH₂ | CH₃ | CN | Cl | NO₂ | |
| 2.038 | Cl | NH₂ | CH₃ | CN | Cl | NO₂ | |
| 2.039 | H | Cl | CH₃ | CN | Cl | NO₂ | m.p. 143–151° C. |
| 2.040 | F | Cl | CH₃ | CSNH₂ | Cl | CN | |

TABLE 3

Compounds of the formula Ic

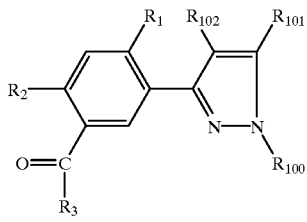

(Ic)

| Compound No. | $R_1$ | $R_2$ | $R_{100}$ | $R_{101}$ | $R_{102}$ | $R_3$ | Physical data |
|---|---|---|---|---|---|---|---|
| 3.001 | H | Cl | $CH_3$ | CN | Cl | Cl | solid |
| 3.002 | H | Br | $CH_3$ | CN | Cl | Cl | |
| 3.003 | H | CN | $CH_3$ | CN | Cl | Cl | |
| 3.004 | F | Cl | $CH_3$ | CN | Cl | Cl | solid |
| 3.005 | F | Br | $CH_3$ | CN | Cl | Cl | |
| 3.006 | F | CN | $CH_3$ | CN | Cl | Cl | |
| 3.007 | F | $NO_2$ | $CH_3$ | CN | Cl | Cl | |
| 3.008 | Cl | Cl | $CH_3$ | CN | Cl | Cl | |
| 3.009 | F | Cl | $CH_3$ | CN | Br | Cl | solid |

TABLE 4

Compounds of the formula Id

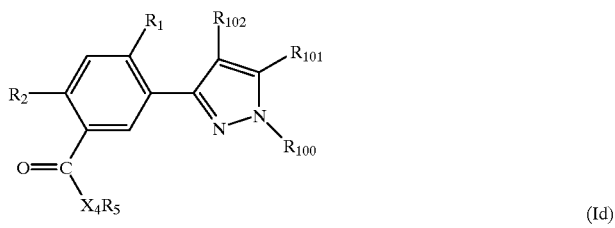

(Id)

| Compound No. | $R_1$ | $R_2$ | $R_{100}$ | $R_{101}$ | $R_{102}$ | $X_4$ | $R_5$ | Physical data |
|---|---|---|---|---|---|---|---|---|
| 4.001 | H | Cl | $CH_3$ | CN | Cl | O | H | m.p. > 210° C. (decomp.) |
| 4.002 | H | Cl | $CH_3$ | CN | Cl | O | $CH_3$ | |
| 4.003 | H | Cl | $CH_3$ | CN | Cl | O | $CH_2CH_3$ | m.p. 160–162° C. |
| 4.004 | H | Cl | $CH_3$ | CN | Cl | O | $CH(CH_3)_2$ | m.p. 87–94° C. |
| 4.005 | F | Cl | $CH_3$ | CN | Cl | O | H | m.p. 224° C. (decomp.) |
| 4.006 | F | Cl | $CH_3$ | CN | Cl | O | $CH_3$ | m.p. 131–132° C. |
| 4.007 | F | Cl | $CH_3$ | CN | Cl | O | $CH_2CH_3$ | m.p. 106–107° C. |
| 4.008 | F | Cl | $CH_3$ | CN | Cl | O | $CH_2$—$CH_2CH_3$ | |
| 4.009 | F | Cl | $CH_3$ | CN | Cl | O | $CH(CH_3)_2$ | m.p. 61–63° C. |
| 4.010 | F | Cl | $CH_3$ | CN | Cl | O | $CH_2CH_2CH_2CH_3$ | |
| 4.011 | F | Cl | $CH_3$ | CN | Cl | O | $CH(CH_3)CH_2CH_3$ | |
| 4.012 | F | Cl | $CH_3$ | CN | Cl | O | $CH_2CH(CH_3)_2$ | |
| 4.013 | F | Cl | $CH_3$ | CN | Cl | O | $C(CH_3)_3$ | |
| 4.014 | F | Cl | $CH_3$ | CN | Cl | O | $(CH_2)_4CH_3$ | |
| 4.015 | F | Cl | $CH_3$ | CN | Cl | O | $CH_2CH_2OCH_3$ | |
| 4.016 | F | Cl | $CH_3$ | CN | Cl | O | $CH_2CH_2OCH_2CH_3$ | |
| 4.017 | F | Cl | $CH_3$ | CN | Cl | O | $CH_2OCH_3$ | |
| 4.018 | F | Cl | $CH_3$ | CN | Cl | O | $CH_2CH_2Cl$ | |
| 4.019 | F | Cl | $CH_3$ | CN | Cl | O | $CH_2SCH_3$ | |
| 4.020 | F | Cl | $CH_3$ | CN | Cl | O | $CH_2CH_2SCH_3$ | |
| 4.021 | F | Cl | $CH_3$ | CN | Cl | O | $CH(CH_3)CH_2SCH_3$ | |
| 4.022 | F | Cl | $CH_3$ | CN | Cl | O | $CH(CH_3)CH_2S$—$CH_2CH_3$ | |
| 4.023 | F | Cl | $CH_3$ | CN | Cl | O | $CH(CH_3)CH_2S$—$CH(CH_3)_2$ | |
| 4.024 | F | Cl | $CH_3$ | CN | Cl | O | $CH_2CH_2$—$N(CH_3)_2$ | |
| 4.025 | F | Cl | $CH_3$ | CN | Cl | O | $CH_2CN$ | |
| 4.026 | F | Cl | $CH_3$ | CN | Cl | O | $CH_2CH_2CN$ | |
| 4.027 | F | Cl | $CH_3$ | CN | Cl | O | $CH(CH_3)CN$ | |
| 4.028 | F | Cl | $CH_3$ | CN | Cl | O | $CH_2CH$=$CH_2$ | |

TABLE 4-continued

Compounds of the formula Id

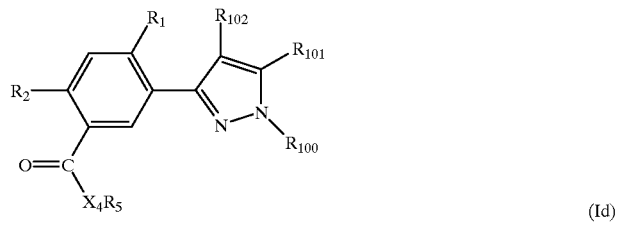

(Id)

| Compound No. | $R_1$ | $R_2$ | $R_{100}$ | $R_{101}$ | $R_{102}$ | $X_4$ | $R_5$ | Physical data |
|---|---|---|---|---|---|---|---|---|
| 4.029 | F | Cl | $CH_3$ | CN | Cl | O | $CH_2C(Cl)=CH_2$ | |
| 4.030 | F | Cl | $CH_3$ | CN | Cl | O | $CH_2C\equiv CH$ | |
| 4.031 | F | Cl | $CH_3$ | CN | Cl | O | ![cyclohexyl] | |
| 4.032 | F | Cl | $CH_3$ | CN | Cl | O | ![CH(CH3)cyclopropyl] | |
| 4.033 | F | Cl | $CH_3$ | CN | Cl | O | ![oxetane] | |
| 4.034 | F | Cl | $CH_3$ | CN | Cl | O | ![CH2-phenyl] | |
| 4.035 | F | Cl | $CH_3$ | CN | Cl | O | Na | |
| 4.036 | F | Cl | $CH_3$ | CN | Cl | O | $H_2N(CH_2CH_3)_2$ | |
| 4.037 | F | Cl | $CH_3$ | CN | Cl | O | $CH(CH_3)CH_2COOCH_3$ | |
| 4.038 | F | Cl | $CH_3$ | CN | Cl | O | $CH(CH_3)CH_2COOCH_2CH_3$ | resin |
| 4.039 | F | Br | $CH_3$ | CN | Cl | O | H | |
| 4.040 | F | Br | $CH_3$ | CN | Cl | O | $CH_3$ | |
| 4.041 | F | Br | $CH_3$ | CN | Cl | O | $CH_2CH_3$ | |
| 4.042 | F | Br | $CH_3$ | CN | Cl | O | $CH(CH_3)_2$ | |
| 4.043 | Cl | Cl | $CH_3$ | CN | Cl | O | H | |
| 4.044 | Cl | Cl | $CH_3$ | CN | Cl | O | $CH_2CH_3$ | m.p. 88–89° C. |
| 4.045 | Cl | Cl | $CH_3$ | CN | Cl | O | $CH(CH_3)_2$ | |
| 4.046 | F | Cl | $CH_3$ | CN | Br | O | $CH(CH_3)_2$ | |
| 4.047 | F | Cl | $CH_3$ | CN | Cl | S | $CH_2CH_3$ | |
| 4.048 | F | Cl | $CH_3$ | CN | Cl | S | $(CH_2)_3CH_3$ | |
| 4.049 | F | Cl | $CH_3$ | CN | Cl | S | $CH(CH_3)_2$ | m.p. 108–110° C. |
| 4.050 | F | Cl | $CH_3$ | CN | Br | S | $CH(CH_3)_2$ | m.p. 125–126° C. |
| 4.051 | F | Cl | $CH_3$ | $CSNH_2$ | Cl | O | H | |
| 4.052 | F | Cl | $CH_3$ | $CSNH_2$ | Cl | O | $CH_3$ | |
| 4.053 | F | Cl | $CH_3$ | $CSNH_2$ | Cl | O | $CH_2CH_3$ | |
| 4.054 | F | Cl | $CH_3$ | $CSNH_2$ | Cl | O | $CH_2CH_2CH_3$ | |
| 4.055 | F | Cl | $CH_3$ | $CSNH_2$ | Cl | O | $CH(CH_3)_2$ | |
| 4.056 | F | Cl | $CH_3$ | $CSNH_2$ | Cl | O | $CH_2CH_2CH_2CH_3$ | |
| 4.057 | F | Cl | $CH_3$ | $CSNH_2$ | Cl | O | $CH(CH_3)CH_2CH_3$ | |
| 4.058 | F | Cl | $CH_3$ | $CSNH_2$ | Cl | O | $CH_2CH(CH_3)_2$ | |
| 4.059 | F | Cl | $CH_3$ | $CSNH_2$ | Cl | O | $CH_2CH_2OCH_2CH_3$ | |
| 4.060 | F | Cl | $CH_3$ | $CSNH_2$ | Cl | O | $CH(CH_3)CH_2SCH_3$ | |
| 4.061 | F | Cl | $CH_3$ | $CSNH_2$ | Cl | O | $CH_2CH=CH_2$ | |
| 4.062 | F | Cl | $CH_3$ | $CSNH_2$ | Cl | O | ![CH2-phenyl] | |
| 4.063 | F | Cl | $CH_3$ | $CSNH_2$ | Cl | O | $CH(CH_3)CH_2COOCH_2CH_3$ | |
| 4.064 | F | Br | $CH_3$ | $CSNH_2$ | Cl | O | $CH_3$ | |
| 4.065 | F | Br | $CH_3$ | $CSNH_2$ | Cl | O | $CH_2CH_3$ | |
| 4.066 | F | Br | $CH_3$ | $CSNH_2$ | Cl | O | $CH(CH_3)_2$ | |

TABLE 4-continued

Compounds of the formula Id

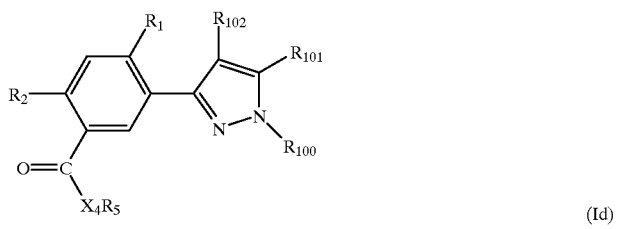

(Id)

| Compound No. | $R_1$ | $R_2$ | $R_{100}$ | $R_{101}$ | $R_{102}$ | $X_4$ | $R_5$ | Physical data |
|---|---|---|---|---|---|---|---|---|
| 4.067 | Cl | Cl | $CH_3$ | $CSNH_2$ | Cl | O | $CH(CH_3)_2$ | |
| 4.068 | H | Cl | $CH_3$ | CN | Cl | O | $CH_2CH{=}CH_2$ | m.p. 120–124° C. |
| 4.069 | F | Cl | $CH_3$ | CN | Br | O | $CH(C_6H_5)_2$ | resin |
| 4.070 | F | Cl | $CH_3$ | CN | Br | O | $CH_2CH_2CN$ | m.p. 152–153° C. |
| 4.071 | F | Cl | $CH_3$ | CN | Br | O | 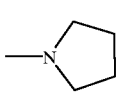 $CH_2$–phenyl | m.p. 151–152° C. |
| 4.072 | F | Cl | $CH_3$ | CN | Br | O | $C(CH_3)_3$ | m.p. 85–86° C. |
| 4.073 | H | Cl | $CH_3$ | CN | Cl | O | $CH_2CH{=}CH_2$ | m.p. 109–117° C. |
| 4.074 | Cl | Cl | $CH_3$ | CN | Cl | O | $CH(CH_3)CH_2COOC_2H_5$ | resin |

TABLE 5

Compounds of the formula Ie

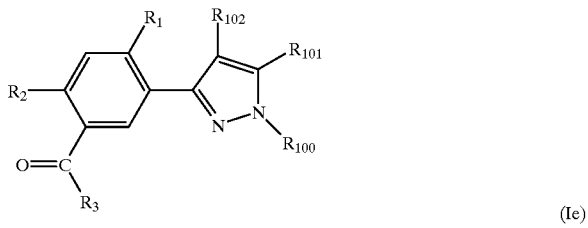

(Ie)

| Compound No. | $R_1$ | $R_2$ | $R_{100}$ | $R_{101}$ | $R_{102}$ | $R_3$ | Physical data |
|---|---|---|---|---|---|---|---|
| 5.001 | H | Cl | $CH_3$ | CN | Cl | $NH_2$ | |
| 5.002 | F | Cl | $CH_3$ | CN | Cl | $NH_2$ | |
| 5.003 | F | Cl | $CH_3$ | CN | Cl | $NHCH_3$ | |
| 5.004 | F | Cl | $CH_3$ | CN | Cl | $NHCH_2CH_2CH_2CH_3$ | |
| 5.005 | F | Cl | $CH_3$ | CN | Cl | $N(CH_3)_2$ | |
| 5.006 | F | Cl | $CH_3$ | CN | Cl | $N(CH_3)CH_2CH_2CH_2CH_3$ | |
| 5.007 | F | Cl | $CH_3$ | CN | Cl | $NHCH_2CH_2OCH_3$ | |
| 5.008 | F | Cl | $CH_3$ | CN | Cl | $NHCH_2CH{=}CH_2$ | |
| 5.009 | F | Cl | $CH_3$ | CN | Cl | $N(CH_2CH{=}CH_2)_2$ | resin |
| 5.010 | F | Cl | $CH_3$ | CN | Cl | 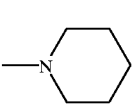 pyrrolidinyl | |
| 5.011 | F | Cl | $CH_3$ | CN | Cl | piperidinyl | |
| 5.012 | F | Cl | $CH_3$ | CN | Cl | 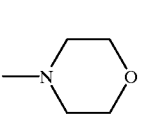 morpholinyl | |

TABLE 5-continued

Compounds of the formula Ie

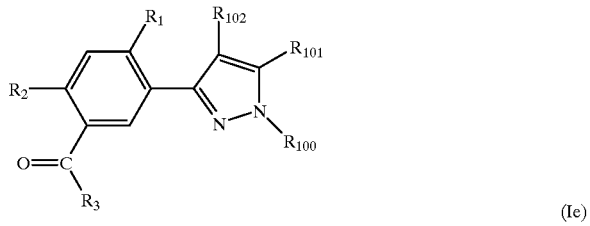

(Ie)

| Compound No. | $R_1$ | $R_2$ | $R_{100}$ | $R_{101}$ | $R_{102}$ | $R_3$ | Physical data |
|---|---|---|---|---|---|---|---|
| 5.013 | F | Cl | $CH_3$ | CN | Cl | 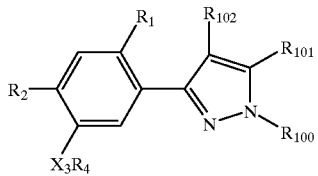 | |
| 5.014 | F | Cl | $CH_3$ | CN | Cl | ON=C(CH$_3$)$_2$ | |
| 5.015 | F | Br | $CH_3$ | CN | Cl | $NH_2$ | |
| 5.016 | Cl | Cl | $CH_3$ | CN | Cl | $NH_2$ | |
| 5.017 | F | Cl | $CH_3$ | $CSNH_2$ | Cl | $NH_2$ | |
| 5.018 | F | Cl | $CH_3$ | $CSNH_2$ | Cl | $NHCH_2CH=CH_2$ | |
| 5.019 | F | Br | $CH_3$ | $CSNH_2$ | Cl | | |
| 5.020 | Cl | Cl | $CH_3$ | $CSNH_2$ | Cl | ON=C(CH$_3$)$_2$ | |
| 5.021 | H | Cl | $CH_3$ | CN | Cl | $NHCH_3$ | m.p. 217–221° C. |
| 5.022 | Cl | Cl | $CH_3$ | CN | Cl | —NH—CH$_2$—C$_6$H$_5$ | m.p. 64–67° C. |

TABLE 6

Compounds of the formula If (If)

| Compound No. | $R_1$ | $R_2$ | $R_{100}$ | $R_{101}$ | $R_{102}$ | $X_3$ | $R_4$ | Physical data |
|---|---|---|---|---|---|---|---|---|
| 6.001 | H | Cl | $CH_3$ | CN | Cl | O | H | m.p. 146–148° C. |
| 6.002 | H | Cl | $CH_3$ | CN | Cl | O | $CH_3$ | |
| 6.003 | H | Cl | $CH_3$ | CN | Cl | O | $CH_2C\equiv CH$ | |
| 6.004 | H | Cl | $CH_3$ | CN | Cl | O | $CH_2COOCH_3$ | |
| 6.005 | H | Cl | $CH_3$ | CN | Cl | O | $CH(CH_3)COOH$ | |
| 6.006 | H | Cl | $CH_3$ | CN | Cl | O | $CH(CH_3)COOCH_2CH_3$ | |
| 6.007 | H | Cl | $CH_3$ | CN | Cl | O | $CH(CH_3)CN$ | |
| 6.008 | F | Cl | $CH_3$ | CN | Cl | O | H | solid |
| 6.009 | F | Cl | $CH_3$ | CN | Cl | O | $CH_3$ | m.p. 156–158° C. |
| 6.010 | F | Cl | $CH_3$ | CN | Br | O | $CH_2CH_3$ | m.p. 141–142° C. |
| 6.011 | F | Cl | $CH_3$ | CN | Cl | O | $CH(CH_3)_2$ | m.p. 86–87° C. |
| 6.012 | F | Cl | $CH_3$ | CN | Br | O | $(CH_2)_5CH_3$ | m.p. 42–43° C. |
| 6.013 | F | Cl | $CH_3$ | CN | Cl | O | $CH_2OCH_3$ | m.p. 115–117° C. |
| 6.014 | F | Cl | $CH_3$ | CN | Cl | O | $CH_2CH_2OCH_2CH_3$ | |
| 6.015 | F | Cl | $CH_3$ | CN | Cl | O | $CH_2SCH_3$ | m.p. 97–98° C. |
| 6.016 | F | Cl | $CH_3$ | CN | Cl | O | $CH(CH_3)CH_2SCH_3$ | |

TABLE 6-continued

Compounds of the formula If

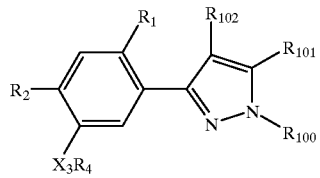

(If)

| Compound No. | $R_1$ | $R_2$ | $R_{100}$ | $R_{101}$ | $R_{102}$ | $X_3$ | $R_4$ | Physical data |
|---|---|---|---|---|---|---|---|---|
| 6.017 | F | Cl | $CH_3$ | CN | Cl | O | $CH(CH_3)CH_2SCH(CH_3)_2$ | |
| 6.018 | F | Cl | $CH_3$ | CN | Cl | O | $CH_2CH_2N(CH_3)_2$ | |
| 6.019 | F | Cl | $CH_3$ | CN | Cl | O | $CH_2CH_2Cl$ | |
| 6.020 | F | Cl | $CH_3$ | CN | Cl | O | $CH_2CH=CH_2$ | |
| 6.021 | F | Cl | $CH_3$ | CN | Cl | O | $CH_2CH=CHCH_3$ | m.p. 87–88° C. |
| 6.022 | F | Cl | $CH_3$ | CN | Cl | O | $CH_2CH=CHCl$ | (E) |
| 6.023 | F | Cl | $CH_3$ | CN | Cl | O | $CH_2CH=CHCl$ | (Z) |
| 6.024 | F | Cl | $CH_3$ | CN | Cl | O | $CH_2C\equiv CH$ | m.p. 138–139° C. |
| 6.025 | F | Cl | $CH_3$ | CN | Cl | O | $CH(CH_3)C\equiv CH$ | m.p. 122–124° C. |
| 6.026 | F | Cl | $CH_3$ | CN | Cl | O | $C(CH_3)_2C\equiv CH$ | |
| 6.027 | F | Cl | $CH_3$ | CN | Cl | O | (cyclohexyl-methyl) | |
| 6.028 | F | Cl | $CH_3$ | CN | Cl | O | (oxetanyl-methyl) | |
| 6.029 | F | Cl | $CH_3$ | CN | Cl | O | $COCH_3$ | m.p. 137–138° C. |
| 6.030 | F | Cl | $CH_3$ | CN | Cl | O | $COCH_2CH_2CH_2CH_2CH_3$ | resin |
| 6.031 | F | Cl | $CH_3$ | CN | Cl | O | $COOCH_3$ | m.p. 131–132° C. |
| 6.032 | F | Cl | $CH_3$ | CN | Cl | O | CO—phenyl | m.p. 136° C. |
| 6.033 | F | Cl | $CH_3$ | CN | Cl | O | $CH_2CN$ | |
| 6.034 | F | Cl | $CH_3$ | CN | Cl | O | $CH(CH_3)CN$ | m.p. 134–135° C. |
| 6.035 | F | Cl | $CH_3$ | CN | Cl | O | $CH_2COOH$ | |
| 6.036 | F | Cl | $CH_3$ | CN | Cl | O | $CH_2COOCH_3$ | |
| 6.037 | F | Cl | $CH_3$ | CN | Cl | O | $CH_2COOCH_2CH_3$ | m.p. 99–100° C. |
| 6.038 | F | Cl | $CH_3$ | CN | Cl | O | $CH_2COO(CH_2)_4CH_3$ | m.p. 115–116° C. |
| 6.039 | F | Cl | $CH_3$ | CN | Cl | O | $CH(CH_3)COOH$ | |
| 6.040 | F | Cl | $CH_3$ | CN | Cl | O | $CH(CH_3)COOCH_3$ | |
| 6.041 | F | Cl | $CH_3$ | CN | Cl | 0 | $CH(CH_3)COOCH_2CH_3$ | m.p. 71–73° C. |
| 6.042 | F | Cl | $CH_3$ | CN | Cl | O | $CH(CH_3)COOCH(CH_3)_2$ | |
| 6.043 | F | Cl | $CH_3$ | CN | Cl | O | $CH(CH_2CH_3)COOCH_3$ | |
| 6.044 | F | Cl | $CH_3$ | CN | Cl | O | $CH_2COOCH_2CH_2SCH_2CH_3$ | |
| 6.045 | F | Cl | $CH_3$ | CN | Cl | O | $CH(CH_3)COOCH(CH_3)CH_2SCH(CH_3)_2$ | |
| 6.046 | F | Cl | $CH_3$ | CN | Cl | O | $CH_2$—phenyl | |
| 6.047 | F | Cl | $CH_3$ | CN | Cl | O | $CH_2$—(4-F-phenyl) | solid |
| 6.048 | F | Cl | $CH_3$ | CN | Cl | O | $CH_2COOCH_2CH_2OCH_3$ | |
| 6.049 | F | Cl | $CH_3$ | CN | Cl | O | $CH(CH_3)COOCH_2CH_2OCH_2CH_3$ | |
| 6.050 | F | Cl | $CH_3$ | CN | Cl | O | $CH_2COOCH_2CH=CH_2$ | |
| 6.051 | F | Cl | $CH_3$ | CN | Cl | O | $CH(CH_3)COOCH_2CH=CH_2$ | m.p. 82–83° C. |
| 6.052 | F | Cl | $CH_3$ | CN | Cl | O | $CH(CH_3)COOCH_2C\equiv CH$ | |
| 6.053 | F | Cl | $CH_3$ | CN | Cl | O | $CH_2COS—CH(CH_3)_2$ | |
| 6.054 | F | Cl | $CH_3$ | CN | Cl | O | $CH(CH_3)COSCH_2CH_2CH_3$ | |

TABLE 6-continued

Compounds of the formula If (If)

[Structure: benzene ring with $R_1$, $R_2$, $X_3R_4$ substituents connected to a pyrazole ring with $R_{100}$, $R_{101}$, $R_{102}$ substituents]

| Compound No. | $R_1$ | $R_2$ | $R_{100}$ | $R_{101}$ | $R_{102}$ | $X_3$ | $R_4$ | Physical data |
|---|---|---|---|---|---|---|---|---|
| 6.055 | F | Cl | $CH_3$ | CN | Cl | O | $CH(CH_3)COSCH_2CH=CH_2$ | |
| 6.056 | F | Cl | $CH_3$ | CN | Cl | O | $CH_2CONH_2$ | |
| 6.057 | F | Cl | $CH_3$ | CN | Cl | O | $CH_2CONHCH_3$ | |
| 6.058 | F | Cl | $CH_3$ | CN | Cl | O | $CH_2CONHCH(CH_3)_2$ | |
| 6.059 | F | Cl | $CH_3$ | CN | Cl | O | $CH(CH_3)CONH_2$ | |
| 6.060 | F | Cl | $CH_3$ | CN | Cl | O | $CH(CH_3)CONHCH_2CH_3$ | |
| 6.061 | F | Cl | $CH_3$ | CN | Cl | O | $CH(CH_3)CON(CH_3)_2$ | |
| 6.062 | F | Cl | $CH_3$ | CN | Cl | O | —CH(1,3-dioxolane) | |
| 6.063 | F | Cl | $CH_3$ | CN | Cl | O | —C(CH$_3$)(1,3-dioxolane) | |
| 6.064 | F | Cl | $CH_3$ | CN | Cl | O | $CH_2COOCH_2$—Ph | m.p. 83–84° C. |
| 6.065 | F | Cl | $CH_3$ | CN | Cl | O | $CH(CH_3)COO$—$CH_2$—Ph | |
| 6.066 | F | Cl | $CH_3$ | CN | Cl | O | $CH_2CONHCH_2CH=CH_2$ | |
| 6.067 | F | Cl | $CH_3$ | CN | Cl | O | $C(CH_3)_2COOH$ | |
| 6.068 | F | Cl | $CH_3$ | CN | Cl | O | $C(CH_3)_2COOCH_3$ | |
| 6.069 | F | Cl | $CH_3$ | CN | Br | O | $C(CH_3)_2COOCH_2CH_3$ | resin |
| 6.070 | F | Cl | $CH_3$ | CN | O | O | $C(CH_3)_2COOCH_2CH=CH_2$ | |
| 6.071 | F | Cl | $CH_3$ | CN | Cl | O | $C(CH_3)_2CONHCH_2CH=CH_2$ | resin |
| 6.072 | F | Br | $CH_3$ | CN | Cl | O | H | |
| 6.073 | F | Br | $CH_3$ | CN | Cl | O | $CH_3$ | |
| 6.074 | F | Br | $CH_3$ | CN | Cl | O | $CH(CH_3)_2$ | |
| 6.075 | F | Br | $CH_3$ | CN | Cl | O | $CH_2C\equiv CH$ | |
| 6.076 | F | Br | $CH_3$ | CN | Cl | O | $CH_2COOH$ | |
| 6.077 | F | Br | $CH_3$ | CN | Cl | O | $CH_2COOCH_2$—Ph | |
| 6.078 | F | Br | $CH_3$ | CN | Cl | O | $CH_2CONH_2$ | |
| 6.079 | F | Br | $CH_3$ | CN | Cl | O | $CH(CH_3)COOH$ | |
| 6.080 | F | Br | $CH_3$ | CN | Cl | O | $CH(CH_3)COOCH_2CH_3$ | |
| 6.081 | F | Br | $CH_3$ | CN | Cl | O | $CH(CH_3)CONHCH_2CH=CH_2$ | |
| 6.082 | F | Br | $CH_3$ | CN | Cl | O | $CH(CH_3)CN$ | |
| 6.083 | F | Br | $CH_3$ | CN | Cl | O | $CH(CH_3)COSCH(CH_3)_2$ | |
| 6.084 | Cl | Cl | $CH_3$ | CN | Cl | O | H | |
| 6.085 | Cl | Cl | $CH_3$ | CN | Cl | O | $CH_3$ | |
| 6.086 | Cl | Cl | $CH_3$ | CN | Cl | O | $CH(CH_3)_2$ | |
| 6.087 | Cl | Cl | $CH_3$ | CN | Cl | O | $CH_2C\equiv CH$ | |

TABLE 6-continued

Compounds of the formula If

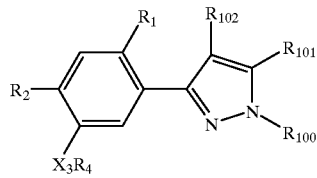

(If)

| Compound No. | $R_1$ | $R_2$ | $R_{100}$ | $R_{101}$ | $R_{102}$ | $X_3$ | $R_4$ | Physical data |
|---|---|---|---|---|---|---|---|---|
| 6.088 | Cl | Cl | $CH_3$ | CN | Cl | O | $CH_2COOCH_2$—C$_6$H$_5$ | |
| 6.089 | Cl | Cl | $CH_3$ | CN | Cl | O | $C(CH_3)_2COOCH_2CH_3$ | |
| 6.090 | F | CN | $CH_3$ | CN | Cl | O | H | |
| 6.091 | F | CN | $CH_3$ | CN | Cl | O | $CH_3$ | |
| 6.092 | F | CN | $CH_3$ | CN | Cl | O | $CH(CH_3)_2$ | |
| 6.093 | F | CN | $CH_3$ | CN | Cl | O | $CH_2C\equiv CH$ | |
| 6.094 | F | CN | $CH_3$ | CN | Cl | O | $CH(CH_3)COOCH_2CH_3$ | |
| 6.095 | F | Cl | $CH_3$ | $CSNH_2$ | Cl | O | H | |
| 6.096 | F | Cl | $CH_3$ | $CSNH_2$ | Cl | O | $CH_3$ | m.p. 175–177° C. |
| 6.097 | F | Cl | $CH_3$ | $CSNH_2$ | Cl | O | $CH(CH_3)_2$ | |
| 6.098 | F | Cl | $CH_3$ | $CSNH_2$ | Cl | O | $CH_2C\equiv CH$ | m.p. 153–156° C. |
| 6.099 | F | Cl | $CH_3$ | $CSNH_2$ | Cl | O | $CH(CH_3)C\equiv CH$ | solid |
| 6.100 | F | Cl | $CH_3$ | $CSNH_2$ | Cl | O | $CH_2COOH$ | |
| 6.101 | F | Cl | $CH_3$ | $CSNH_2$ | Cl | O | $CH_2COOCH_3$ | |
| 6.102 | F | Cl | $CH_3$ | $CSNH_2$ | Cl | O | $CH_2COOCH(CH_3)_2$ | |
| 6.103 | F | Cl | $CH_3$ | $CSNH_2$ | Cl | O | $CH_2COOCH_2$—C$_6$H$_5$ | |
| 6.104 | F | Cl | $CH_3$ | $CSNH_2$ | Cl | O | $CH(CH_3)COOH$ | |
| 6.105 | F | Cl | $CH_3$ | $CSNH_2$ | Cl | O | $CH(CH_3)COOCH_3$ | |
| 6.106 | F | Cl | $CH_3$ | $CSNH_2$ | Cl | O | $CH(CH_3)COOCH_2CH_3$ | resin |
| 6.107 | F | Cl | $CH_3$ | $CSNH_2$ | Cl | O | $CH(CH_3)COOCH(CH_3)_2$ | |
| 6.108 | F | Cl | $CH_3$ | $CSNH_2$ | Cl | O | $CH(CH_3)COOCH_2CH\!=\!CH_2$ | |
| 6.109 | F | Cl | $CH_3$ | $CSNH_2$ | Cl | O | $CH(CH_3)COOCH_2$—C$_6$H$_5$ | |
| 6.110 | F | Cl | $CH_3$ | $CSNH_2$ | Cl | O | $C(CH_3)_2COOH$ | |
| 6.111 | F | Cl | $CH_3$ | $CSNH_2$ | Cl | O | $C(CH_3)_2COOCH_2CH_3$ | |
| 6.112 | F | Cl | $CH_3$ | $CSNH_2$ | Cl | O | $C(CH_3)_2COOCH_2CH\!=\!CH_2$ | |
| 6.113 | F | Cl | $CH_3$ | $CSNH_2$ | Cl | O | $CH(CH_3)CONH_2$ | |
| 6.114 | F | Cl | $CH_3$ | $CSNH_2$ | Cl | O | $CH(CH_3)CONHCH_2CH\!=\!CH_2$ | |
| 6.115 | F | Cl | $CH_3$ | $CSNH_2$ | Cl | O | $CH(CH_3)CN$ | |
| 6.116 | F | Br | $CH_3$ | $CSNH_2$ | Cl | O | H | |
| 6.117 | F | Br | $CH_3$ | $CSNH_2$ | Cl | O | $CH_3$ | |
| 6.118 | F | Br | $CH_3$ | $CSNH_2$ | Cl | O | $CH(CH_3)_2$ | |
| 6.119 | F | Br | $CH_3$ | $CSNH_2$ | Cl | O | $CH_2C\equiv CH$ | |
| 6.120 | F | Br | $CH_3$ | $CSNH_2$ | Cl | O | $CH(CH_3)COOCH(CH_3)_2$ | |
| 6.121 | Cl | Cl | $CH_3$ | $CSNH_2$ | Cl | O | H | |
| 6.122 | Cl | Cl | $CH_3$ | $CSNH_2$ | Cl | O | $CH_2C\equiv CH$ | |
| 6.123 | Cl | Cl | $CH_3$ | $CSNH_2$ | Cl | O | $CH_2COOH$ | |
| 6.124 | H | Cl | $CH_3$ | CN | Cl | S | H | m.p. 146–148° C. |
| 6.125 | H | Cl | $CH_3$ | CN | Cl | S | $CH(CH_3)_2$ | m.p. 119–122° C. |
| 6.126 | H | Cl | $CH_3$ | CN | Cl | S | $CH_2COOCH_3$ | m.p. 121–125° C. |
| 6.127 | F | Cl | $CH_3$ | CN | Cl | S | H | m.p. 127–129° C. |
| 6.128 | F | Cl | $CH_3$ | CN | Cl | S | $CH_3$ | |
| 6.129 | F | Cl | $CH_3$ | CN | Cl | S | $CH(CH_3)_2$ | m.p. 67–70° C. |
| 6.130 | F | Cl | $CH_3$ | CN | Cl | S | $CH_2COOH$ | |
| 6.131 | F | Cl | $CH_3$ | CN | Cl | S | $CH_2COOCH_3$ | m.p. 98–100° C. |
| 6.132 | F | Cl | $CH_3$ | CN | Cl | S | $CH_2COOCH(CH_3)_2$ | m.p. 55–57° C. |

TABLE 6-continued

Compounds of the formula If

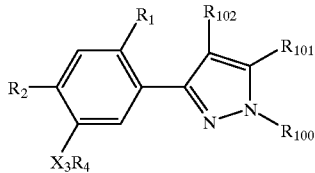

(If)

| Compound No. | $R_1$ | $R_2$ | $R_{100}$ | $R_{101}$ | $R_{102}$ | $X_3$ | $R_4$ | Physical data |
|---|---|---|---|---|---|---|---|---|
| 6.133 | F | Cl | $CH_3$ | CN | Cl | S | $CH_2COOCH_2$—C$_6$H$_5$ | m.p. 99–103° C. |
| 6.134 | F | Cl | $CH_3$ | CN | Cl | S | $CH_2CONHCH_2CH=CH_2$ | m.p. 140–142° C. |
| 6.135 | F | Cl | $CH_3$ | CN | Cl | S | $CH_2CONHCH_2CH_2CH_3$ | m.p. 137–138° C. |
| 6.136 | F | Cl | $CH_3$ | CN | Cl | S | $CH(CH_3)COOH$ | |
| 6.137 | F | Cl | $CH_3$ | CN | Cl | S | $CH(CH_3)COOCH_3$ | |
| 6.138 | F | Cl | $CH_3$ | CN | Cl | S | $CH(CH_3)COOCH_2CH_3$ | |
| 6.139 | F | Cl | $CH_3$ | CN | Cl | S | $CH(CH_3)COOCH(CH_3)_2$ | oil |
| 6.140 | F | Cl | $CH_3$ | CN | Cl | S | $CH(CH_2CH_3)COOH$ | |
| 6.141 | F | Cl | $CH_3$ | CN | Cl | S | $CH_2C\equiv CH$ | m.p. 126–127° C. |
| 6.142 | F | Cl | $CH_3$ | CN | Cl | S | $CH_2OCH_3$ | m.p. 92–96° C. |
| 6.143 | F | Cl | $CH_3$ | CN | Cl | S | $CH_2CH_2O\ CH_2CH_3$ | m.p. 62–66° C. |
| 6.144 | F | Cl | $CH_3$ | CN | Cl | S | $CH(CH_3)CN$ | |
| 6.145 | F | Br | $CH_3$ | CN | Cl | S | H | |
| 6.146 | F | Br | $CH_3$ | CN | Cl | S | $CH_2COOH$ | |
| 6.147 | F | Br | $CH_3$ | CN | Cl | S | $CH_2COOCH_3$ | |
| 6.148 | Cl | Cl | $CH_3$ | CN | Cl | S | H | m.p. 96–99° C. |
| 6.149 | Cl | Cl | $CH_3$ | CN | Cl | S | $CH_3$ | |
| 6.150 | F | Cl | $CH_3$ | $CSNH_2$ | Cl | S | H | |
| 6.151 | F | Cl | $CH_3$ | $CSNH_2$ | Cl | S | $CH_2COOCH_3$ | |
| 6.152 | F | Cl | $CH_3$ | CN | Cl | NH | —$COCH_3$ | |
| 6.153 | F | Cl | $CH_3$ | CN | Cl | $NCH_3$ | —$COCH_3$ | |
| 6.154 | F | Cl | $CH_3$ | CN | Cl | NH | —$COOCH_2CH_3$ | |
| 6.155 | F | Cl | $CH_3$ | CN | Cl | NH | —CO—C$_6$H$_5$ | |
| 6.156 | F | Cl | $CH_3$ | CN | Cl | NH | —$COSCH_3$ | |
| 6.157 | F | Cl | $CH_3$ | CN | Cl | NH | $CONH_2$ | |
| 6.158 | F | Cl | $CH_3$ | CN | Cl | NH | $CONHCH_3$ | |
| 6.159 | F | Cl | $CH_3$ | CN | Cl | $NCH_3$ | $CONHCH_3$ | |
| 6.160 | F | Cl | $CH_3$ | CN | Cl | NH | $CONH(CH_2)_3CH_3$ | |
| 6.161 | F | Cl | $CH_3$ | $CSNH_2$ | Cl | NH | $COCH_3$ | |
| 6.162 | F | Cl | $CH_2CH_3$ | CN | Cl | O | H | |
| 6.163 | F | Cl | $CH_2CH_3$ | CN | Cl | O | $CH_3$ | m.p. 101–103° C. |
| 6.164 | F | Cl | $CH(CH_3)_2$ | CN | Cl | O | H | |
| 6.165 | F | Cl | $CH(CH_3)_2$ | CN | Cl | O | $CH_3$ | m.p. 63–65° C. |
| 6.166 | F | Cl | $CH_2C\equiv CH$ | CN | Cl | O | $CH_3$ | m.p. 94–96° C. |
| 6.167 | F | Cl | $CH_2CN$ | CN | Cl | O | H | |
| 6.168 | F | Cl | $CH_2CN$ | CN | Cl | O | $CH_3$ | |
| 6.169 | F | Cl | $CH_2CN$ | CN | Cl | O | $CH_2C\equiv CH$ | |
| 6.170 | F | Cl | $CH_3$ | CN | Cl | O | $CH_2COOCH_2O\equiv CH$ | m.p. 145–147° C. |
| 6.171 | F | Cl | $CH_3$ | CN | Cl | O | $SO_2CF_3$ | m.p. 78–80° C. |
| 6.172 | F | Cl | $CH_3$ | CN | Cl | O | $COOCH=CH_2$ | m.p. 89–91° C. |
| 6.173 | F | Cl | $CH_3$ | CN | Cl | O | $COC(CH_3)_3$ | resin |
| 6.174 | F | Cl | $CH_3$ | CN | Br | O | H | solid |
| 6.175 | F | Cl | $CH_3$ | $CSNH_2$ | Br | O | H | |
| 6.176 | F | Cl | $CH_3$ | CN | Br | O | $CH_3$ | m.p. 160–162° C. |
| 6.177 | F | Cl | $CH_3$ | $CSNH_2$ | Br | O | $CH_3$ | |
| 6.178 | F | Cl | $CH_3$ | CN | Br | O | $CH_2C\equiv CH$ | |
| 6.179 | F | Cl | $CH_3$ | $CSNH_2$ | Br | O | $CH_2C\equiv CH$ | |
| 6.180 | F | Cl | $CH_3$ | $CONH(C_6H_5)$ | Cl | O | $CH_3$ | m.p. 165–166° C. |
| 6.181 | F | Cl | $CH_3$ | $CONH(CH_3)$ | Cl | O | $CH_3$ | m.p. 158–160° C. |
| 6.182 | F | Cl | $CH_3$ | $NH_2$ | Cl | O | H | |
| 6.183 | F | Cl | $CH_3$ | $NH_2$ | Cl | O | $CH_3$ | m.p. 114–118° C. |
| 6.184 | F | Cl | $CH_3$ | NH—CHO | Cl | O | $CH_3$ | m.p. 199–201° C. |

TABLE 6-continued

Compounds of the formula If

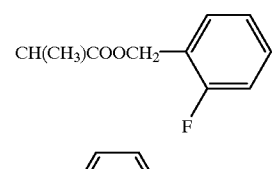

(If)

| Compound No. | $R_1$ | $R_2$ | $R_{100}$ | $R_{101}$ | $R_{102}$ | $X_3$ | $R_4$ | Physical data |
|---|---|---|---|---|---|---|---|---|
| 6.185 | F | Cl | $CH_3$ | NC | Cl | O | H | |
| 6.186 | F | Cl | $CH_3$ | NC | Cl | O | $CH_3$ | m.p. 121–123° C. |
| 6.187 | F | Cl | $CH_3$ | CN | Br | O | $CH_2COOH$ | solid |
| 6.188 | F | Cl | $CH_3$ | CN | Br | O | $CH_2COOC(CH_3)_3$ | solid |
| 6.189 | F | Cl | $CH_3$ | CN | Br | O | $CH_2CH=CHCl$ (E) | solid |
| 6.190 | F | Cl | $CH_3$ | CN | Br | O | $CH_2CH=CHCl$ (Z) | solid |
| 6.191 | F | Cl | $CH_3$ | CN | Br | O | $CH(CH_3)C\equiv CH$ | solid |
| 6.192 | F | Cl | $CH_3$ | $CSNH_2$ | Br | O | $CH(CH_3)C\equiv CH$ | m.p. 130–132° C. |
| 6.193 | F | Cl | $CH_3$ | CN | Br | O |  | m.p. 72–74° C. |
| 6.194 | F | Cl | $CH_3$ | CN | Br | O | 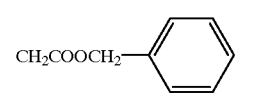 | m.p. 91–93° C. |
| 6.195 | F | Cl | $CH_3$ | CN | Br | O | 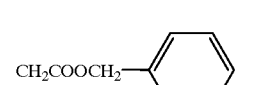 | m.p. 103–104° C. |
| 6.196 | F | Cl | $CH_3$ | $CSNH_2$ | Br | O | 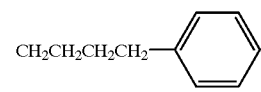 | m.p. 150–151° C. |
| 6.197 | F | Cl | $CH_3$ | CN | Br | O | $CH_2CONH-CH_2CH=CH_2$ | m.p. 133–136° C. |
| 6.198 | F | Cl | $CH_3$ | $CSNH_2$ | Br | O | $CH_2CONHCH_2CH=CH_2$ | m.p. 172–173° C. |
| 6.199 | F | Cl | $CH_3$ | CN | Br | O | $CH_2COOCH_2CH_3$ | |
| 6.200 | F | Cl | $CH_3$ | CN | Br | O | $CH(CH_3)COOH$ | |
| 6.201 | F | Cl | $CH_3$ | CN | Br | O | $CH(CH_3)COOCH_2CH_3$ | |
| 6.202 | F | Cl | $CH_3$ | $CSNH_2$ | Br | O | $CH(CH_3)COOCH_2CH_3$ | |
| 6.203 | F | Cl | $CH_3$ | CN | Br | O | $CH_2COSCH(CH_3)_2$ | m.p. 99–100° C. |
| 6.204 | F | Cl | $CH_3$ | CN | Cl | O | $CH_2CH_2CH_2CH_3$ | solid |
| 6.205 | F | Cl | $CH_3$ | CN | Cl | O | $CH_2CH_2CH_2CH_2CH_3$ | m.p. 53–54° C. |
| 6.206 | F | Cl | $CH_3$ | $CSNH_2$ | Cl | O | $CH_2CH_2CH_2CH_2CH_3$ | m.p. 114–116° C. |
| 6.207 | F | Cl | $CH_3$ | $CSNH_2$ | Cl | O | $CH_2CH_2SCH_2CH_3$ | m.p. 137–139° C. |
| 6.208 | F | Cl | $CH_3$ | CN | Cl | O | $CH_2COSCH_2COOCH_2CH_3$ | m.p. 86–88° C. |
| 6.209 | F | Cl | $CH_3$ | CN | Cl | O | 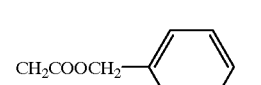 | m.p. 45–48° C. |
| 6.210 | F | Cl | $CH_3$ | $CSNH_2$ | Cl | S |  | m.p. 105–110° C. |
| 6.211 | F | Cl | $CH_3$ | $CSNH_2$ | Cl | S | $CH_2COOCH(CH_3)_2$ | m.p. >85° C. |
| 6.212 | F | Cl | $CH_3$ | CN | Cl | O | $CH_2COOCH_2C\equiv CH$ | m.p. 145–147° C. |

TABLE 6-continued

Compounds of the formula If

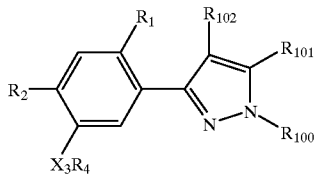

(If)

| Compound No. | $R_1$ | $R_2$ | $R_{100}$ | $R_{101}$ | $R_{102}$ | $X_3$ | $R_4$ | Physical data |
|---|---|---|---|---|---|---|---|---|
| 6.213 | F | Cl | $CH_3$ | CN | Cl | O | $CH_2COOCH_2$—phenyl | m.p. 83–84° C. |
| 6.214 | F | Cl | $CH_3$ | CN | Cl | O | $CH_2CH_2SCH_2CH_3$ | m.p. 92–93° C. |
| 6.215 | F | Cl | $CH_3$ | CN | Cl | O | $C(CH_3)_2COOCH_2CH_3$ | resin |
| 6.216 | F | Cl | $CH_3$ | CN | Cl | O | $CH(CH_3)CF_3$ | m.p. 82–85° C. |
| 6.217 | F | Cl | $CH_3$ | CN | Cl | O | —$CH(CH_3)COOCH_2$-(2-F-phenyl) | m.p. 53–55° C. |
| 6.218 | F | Br | $CH_3$ | CN | Br | O | —$CH_2C{\equiv}CH$ | m.p. 153–156° C. |
| 6.219 | F | CN | $CH_3$ | CN | Br | O | $CH_3$ | m.p. 220–221° C. |
| 6.220 | F | Br | $CH_3$ | CN | Br | O | $CH_3$ | m.p. 173–175° C. |
| 6.221 | Cl | Cl | $CH_3$ | CN | Cl | S | $CH_2COOCH_3$ | m.p. 108–111° C. |
| 6.222 | Cl | Cl | $CH_3$ | CN | Cl | S | —$CH(CH_3)COOCH_3$ | m.p. 108–110° C. |

TABLE 7

Compounds of the formula Ig

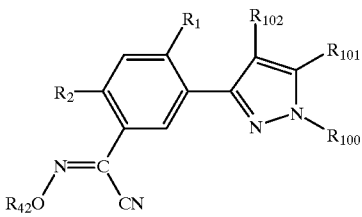

(Ig)

| Compound No. | $R_1$ | $R_2$ | $R_{100}$ | $R_{101}$ | $R_{102}$ | $R_{42}$ | Physical data |
|---|---|---|---|---|---|---|---|
| 7.01 | F | Cl | $CH_3$ | CN | Cl | H | |
| 7.02 | F | Cl | $CH_3$ | CN | Cl | $CH_3$ | |
| 7.03 | F | Cl | $CH_3$ | CN | Cl | $CH_2CH{=}CH_2$ | |
| 7.04 | F | Cl | $CH_3$ | CN | Cl | $CH_2C{\equiv}CH$ | |
| 7.05 | F | Cl | $CH_3$ | CN | Cl | $CH_2COOCH_3$ | |
| 7.06 | F | Cl | $CH_3$ | CN | Cl | $CH(CH_3)COOCH_2CH_3$ | |
| 7.07 | Cl | Cl | $CH_3$ | CN | Cl | $CH(CH_3)COOCH_2CH_3$ | |

TABLE 8

Compounds of the formula Ih

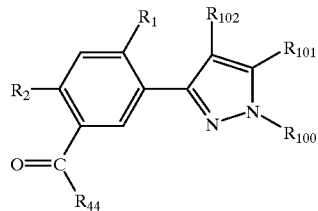

(Ih)

| Compound No. | $R_1$ | $R_2$ | $R_{100}$ | $R_{101}$ | $R_{102}$ | $R_{44}$ | Physical data |
|---|---|---|---|---|---|---|---|
| 8.01 | F | Cl | $CH_3$ | CN | Cl | H | |
| 8.02 | F | Cl | $CH_3$ | CN | Cl | $CH_3$ | |
| 8.03 | F | Cl | $CH_3$ | CN | Cl | $CF_3$ | |
| 8.04 | F | Cl | $CH_3$ | CN | Cl | cyclopropyl | |
| 8.05 | F | Cl | $CH_3$ | CN | Cl | $CH_2CH_3$ | |
| 8.06 | F | Cl | $CH_3$ | CN | Cl | $CH_2OCH_3$ | |
| 8.07 | F | Cl | $CH_3$ | CN | Cl | $CH_2Br$ | |

TABLE 9

Compounds of the formula Ii

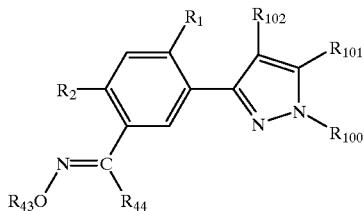

(Ii)

| Compound No. | $R_1$ | $R_2$ | $R_{100}$ | $R_{101}$ | $R_{102}$ | $R_{43}$ | $R_{44}$ | Physical data |
|---|---|---|---|---|---|---|---|---|
| 9.01 | F | Cl | $CH_3$ | CN | Cl | H | H | |
| 9.02 | F | Cl | $CH_3$ | CN | Cl | $CH_3$ | H | |
| 9.03 | F | Cl | $CH_3$ | CN | Cl | H | $CH_3$ | |
| 9.04 | F | Cl | $CH_3$ | CN | Cl | $CH(CH_3)COOCH_3$ | $CH_3$ | |
| 9.05 | F | Cl | $CH_3$ | CN | Cl | $CH_2CH=CH_2$ | $CH_3$ | |
| 9.06 | F | Cl | $CH_3$ | CN | Cl | $CH_3$ | $CH_3$ | |
| 9.07 | F | Cl | $CH_3$ | $CSNH_2$ | Cl | $CH_3$ | $CH_3$ | |

TABLE 10

Compounds of the formula Ij

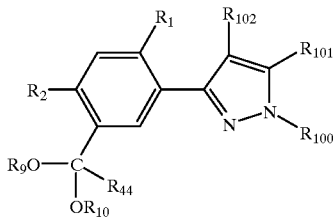

(Ij)

| Compound No. | $R_1$ | $R_2$ | $R_{100}$ | $R_{101}$ | $R_{102}$ | $R_9$ | $R_{10}$ | $R_{44}$ | Physical data |
|---|---|---|---|---|---|---|---|---|---|
| 10.01 | F | Cl | $CH_3$ | CN | Cl | $CH_3$ | $CH_3$ | $CH_3$ | |
| 10.02 | F | Cl | $CH_3$ | CN | Cl | —$CH_2CH_2$— | | $CH_3$ | |
| 10.03 | F | Cl | $CH_3$ | CN | Cl | —$CH(CH_3)CH_2$— | | $CH_3$ | |
| 10.04 | F | Cl | $CH_3$ | CN | Cl | —$CH(CH_3)CH(CH_3)$— | | $CH_3$ | |
| 10.05 | F | Cl | $CH_3$ | $CSNH_2$ | Cl | —$CH(CH_3)CH_2$— | | $CH_3$ | |
| 10.06 | F | Cl | $CH_3$ | $CSNH_2$ | Cl | —$CH(CH_3)CH(CH_3)$— | | $CH_3$ | |
| 10.07 | Cl | Cl | $CH_3$ | CN | Cl | —$CH(CH_3)CH(CH_3)$— | | $CH_3$ | |

TABLE 11

Compounds of the formula Ik

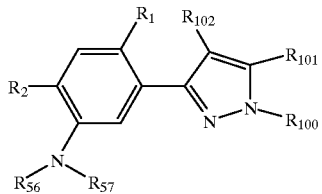

(Ik)

| Compound No. | $R_1$ | $R_2$ | $R_{100}$ | $R_{101}$ | $R_{102}$ | $R_{56}$ | $R_{57}$ | Physical data |
|---|---|---|---|---|---|---|---|---|
| 11.01 | H | Cl | $CH_3$ | CN | Cl | H | H | m.p. 144–147° C. |
| 11.02 | H | Cl | $CH_3$ | CN | Cl | $CH_3$ | H | |
| 11.03 | H | Cl | $CH_3$ | CN | Cl | $CH_2CH=CH_2$ | H | |
| 11.04 | F | Cl | $CH_3$ | CN | Cl | H | H | m.p. 163–165° C. |
| 11.05 | F | Cl | $CH_3$ | CN | Cl | $CH_3$ | H | |
| 11.06 | F | Cl | $CH_3$ | CN | Cl | $CH_2CH=CH_2$ | H | |
| 11.07 | F | Cl | $CH_3$ | CN | Cl | $CH_2CH=CH_2$ | $CH_2CH=CH_2$ | resin |
| 11.08 | F | Cl | $CH_3$ | CN | Cl | $CH_2$—C$_6$H$_5$ | H | |
| 11.09 | F | Cl | $CH_3$ | CN | Cl | $CH_2CN$ | H | |
| 11.10 | F | Cl | $CH_3$ | CN | Cl | $CH_2COOCH_3$ | H | |
| 11.11 | F | Cl | $CH_3$ | CN | Cl | $CH_2COOCH_3$ | $CH_3$ | |
| 11.12 | F | Cl | $CH_3$ | CN | Cl | $CH(CH_3)COOCH_3$ | H | |
| 11.13 | F | Cl | $CH_3$ | CN | Cl | $CH(CH_3)COOCH_2CH_3$ | H | |
| 11.14 | F | Cl | $CH_3$ | CN | Cl | $CH(CH_3)COOCH_2CH_3$ | $CH_3$ | |
| 11.15 | F | Cl | $CH_3$ | CN | Cl | $CH_2CH_2$—morpholinyl | H | |
| 11.16 | F | Cl | $CH_3$ | CN | Cl | $CH_2CONH_2$ | H | |
| 11.17 | F | Cl | $CH_3$ | CN | Cl | $CH_2CONH_2$ | $CH_3$ | |
| 11.18 | F | Cl | $CH_3$ | $CSNH_2$ | Cl | $CH_2COOCH_3$ | $CH_3$ | |
| 11.19 | Cl | Cl | $CH_3$ | CN | Cl | $CH_2COOCH_3$ | $CH_3$ | |

TABLE 11-continued

Compounds of the formula Ik

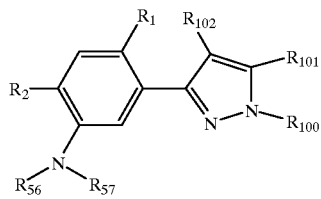

(Ik)

| Compound No. | $R_1$ | $R_2$ | $R_{100}$ | $R_{101}$ | $R_{102}$ | $R_{56}$ | $R_{57}$ | Physical data |
|---|---|---|---|---|---|---|---|---|
| 11.20 | F | Cl | $CH_3$ | CN | Cl | | | |
| 11.21 | Cl | Cl | $CH_3$ | CN | Cl | H | H | solid |

For 11.20, $R_{56}$–$R_{57}$ together form a morpholino group (—N(CH$_2$CH$_2$)$_2$O).

TABLE 12

Compounds of the formula Im

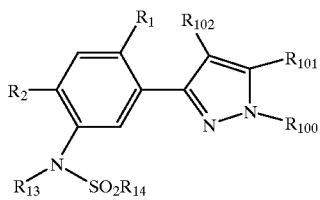

(Im)

| Compound No. | $R_1$ | $R_2$ | $R_{100}$ | $R_{101}$ | $R_{102}$ | $R_{13}$ | $R_{14}$ | Physical data |
|---|---|---|---|---|---|---|---|---|
| 12.01 | H | Cl | $CH_3$ | CN | Cl | H | $SO_2CH_3$ | m.p. 87–94° C. |
| 12.02 | H | Cl | $CH_3$ | CN | Cl | $SO_2CH_3$ | $SO_2CH_3$ | m.p. >205° C. |
| 12.03 | F | Cl | $CH_3$ | CN | Cl | H | $SO_2CH_3$ | |
| 12.04 | F | Cl | $CH_3$ | CN | Cl | $SO_2CH_3$ | $SO_2CH_3$ | |
| 12.05 | F | Cl | $CH_3$ | CN | Cl | H | $SO_2CH_2CH_3$ | |
| 12.06 | F | Cl | $CH_3$ | CN | Cl | $SO_2CH_2CH_3$ | $SO_2CH_2CH_3$ | m.p. 189–191° C. |
| 12.07 | F | Cl | $CH_3$ | CN | Cl | H | $SO_2CH(CH_3)_2$ | |
| 12.08 | F | Cl | $CH_3$ | CN | Cl | $SO_2CH(CH_3)_2$ | $SO_2CH(CH_3)_2$ | |
| 12.09 | F | Cl | $CH_3$ | CN | Cl | H | $SO_2$-phenyl | |
| 12.10 | F | Cl | $CH_3$ | CN | Cl | $SO_2$-phenyl | $SO_2$-phenyl | |
| 12.11 | F | Cl | $CH_3$ | CN | Cl | $CH_3$ | $SO_2CH_3$ | |
| 12.12 | F | Cl | $CH_3$ | CN | Cl | $CH_2CH=CH_2$ | $SO_2CH_2CH_3$ | |
| 12.13 | F | Cl | $CH_3$ | CN | Cl | $CH_2$-phenyl | $SO_2CH(CH_3)_2$ | |
| 12.14 | F | Cl | $CH_3$ | $CSNH_2$ | Cl | $CH_2CH_3$ | $SO_2CH_2CH_3$ | |

TABLE 12-continued

Compounds of the formula Im

(Im)

| Compound No. | $R_1$ | $R_2$ | $R_{100}$ | $R_{101}$ | $R_{102}$ | $R_{13}$ | $R_{14}$ | Physical data |
|---|---|---|---|---|---|---|---|---|
| 12.15 | Cl | Cl | $CH_3$ | CN | Cl | H | $SO_2CH_3$ | resin |
| 12.16 | Cl | Cl | $CH_3$ | CN | Cl | $SO_2CH_3$ | $SO_2CH_3$ | m.p. 189–191° C. |
| 12.17 | Cl | Cl | $CH_3$ | CN | Cl | H | $SO_2CH(CH_3)_2$ | |
| 12.18 | Cl | Cl | $CH_3$ | CN | Cl | $SO_2CH(CH_3)_2$ | $SO_2CH(CH_3)_2$ | |
| 12.19 | Cl | Cl | $CH_3$ | $CSNH_2$ | Cl | $CH_2CH=CH_2$ | $SO_2CH_3$ | |
| 12.20 | F | Br | $CH_3$ | CN | Cl | H | $SO_2CH_2CH_3$ | |
| 12.21 | F | Br | $CH_3$ | CN | Cl | $SO_2CH_2CH_3$ | $SO_2CH_2CH_3$ | |
| 12.22 | F | Cl | $CH_3$ | CN | Cl | H | $SO_2$—◁ | |
| 12.23 | F | Cl | $CH_3$ | CN | Cl | $SO_2$—◁ | $SO_2$—◁ | |

TABLE 13

Compounds of the formula In

(In)

| Compound No. | $R_1$ | $R_2$ | $R_{100}$ | $R_{101}$ | $R_{102}$ | $R_{15}$ | $A_1$ | Physical data |
|---|---|---|---|---|---|---|---|---|
| 13.01 | H | Cl | $CH_3$ | CN | Cl | H | CN | |
| 13.02 | H | Cl | $CH_3$ | CN | Cl | H | COCl | |
| 13.03 | H | Cl | $CH_3$ | CN | Cl | $CH_3$ | COCl | |
| 13.04 | H | Cl | $CH_3$ | CN | Cl | H | $CONH_2$ | |
| 13.05 | F | Cl | $CH_3$ | CN | Cl | H | CN | |
| 13.06 | F | Cl | $CH_3$ | CN | Cl | H | COCl | |
| 13.07 | F | Cl | $CH_3$ | CN | Cl | H | $CONH_2$ | |
| 13.08 | F | Cl | $CH_3$ | CN | Cl | H | $CONH(CH_3)$ | |
| 13.09 | F | Cl | $CH_3$ | CN | Cl | $CH_3$ | COCl | |
| 13.10 | F | Cl | $CH_3$ | CN | Cl | F | COCl | |
| 13.11 | F | Cl | $CH_3$ | CN | Br | H | COCl | |
| 13.12 | F | Cl | $CH_3$ | CN | Cl | $CH_3$ | CN | |
| 13.13 | Cl | Cl | $CH_3$ | CN | Cl | H | CN | |
| 13.14 | Cl | Cl | $CH_3$ | CN | Cl | H | COCl | |
| 13.15 | Cl | Cl | $CH_3$ | CN | Cl | H | $CONH_2$ | |
| 13.16 | Cl | Cl | $CH_3$ | CN | Cl | H | $CONHCH_2CH=CH_2$ | |
| 13.17 | Cl | Cl | $CH_3$ | CN | Cl | $CH_3$ | CN | |
| 13.18 | Cl | Cl | $CH_3$ | CN | Cl | $CH_3$ | COCl | |
| 13.19 | Cl | Cl | $CH_3$ | CN | Cl | $CH_3$ | $CONH_2$ | |

TABLE 14

Compounds of the formula Io

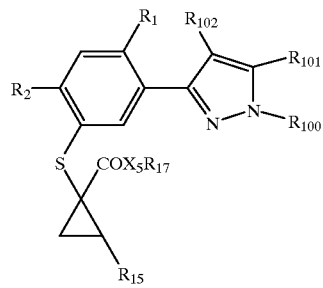

(Io)

| Compound No. | $R_1$ | $R_2$ | $R_{100}$ | $R_{101}$ | $R_{102}$ | $X_5$ | $R_{15}$ | $R_{17}$ | Physical data |
|---|---|---|---|---|---|---|---|---|---|
| 14.01 | H | Cl | $CH_3$ | CN | Cl | O | H | H | |
| 14.02 | H | Cl | $CH_3$ | CN | Cl | O | H | $CH_3$ | |
| 14.03 | H | Cl | $CH_3$ | CN | Cl | O | H | $CH(CH_3)_2$ | |
| 14.04 | H | Cl | $CH_3$ | CN | Cl | O | H | $CH_2CH=CH_2$ | |
| 14.05 | F | Cl | $CH_3$ | CN | Cl | O | H | H | |
| 14.06 | F | Cl | $CH_3$ | CN | Cl | O | H | $CH_3$ | |
| 14.07 | F | Cl | $CH_3$ | CN | Cl | O | H | $CH_2CH_3$ | |
| 14.08 | F | Cl | $CH_3$ | CN | Cl | O | H | $CH(CH_3)_2$ | |
| 14.09 | F | Cl | $CH_3$ | CN | Cl | O | H | $CH_2CH_2CH_2CH_3$ | |
| 14.10 | F | Cl | $CH_3$ | CN | Cl | O | H | $CH_2CH_2Cl$ | |
| 14.11 | F | Cl | $CH_3$ | CN | Cl | O | H | $CH_2CH_2CH_3$ | |
| 14.12 | F | Cl | $CH_3$ | CN | Cl | O | H | | |
| 14.13 | F | Cl | $CH_3$ | CN | Cl | O | H | $CH(CH_3)N(CH_3)_2$ | |
| 14.14 | F | Cl | $CH_3$ | CN | Cl | O | H | cyclohexyl | |
| 14.15 | F | Cl | $CH_3$ | CN | Cl | O | H | $CH_2C\equiv CH$ | |
| 14.16 | F | Cl | $CH_3$ | CN | Cl | O | H | $CH_2$-phenyl | |
| 14.17 | F | Cl | $CH_3$ | CN | Cl | O | $CH_3$ | $CH_2CH_3$ | |
| 14.18 | F | Cl | $CH_3$ | CN | Cl | O | F | $CH_3$ | |
| 14.19 | F | Cl | $CH_3$ | CN | Cl | O | F | $CH(CH_3)_2$ | |
| 14.20 | F | Cl | $CH_3$ | $CSNH_2$ | Cl | O | H | H | |
| 14.21 | F | Cl | $CH_3$ | $CSNH_2$ | Cl | O | H | $CH_3$ | |
| 14.22 | F | Cl | $CH_3$ | $CSNH_2$ | Cl | O | H | cyclopentyl | |
| 14.23 | F | Br | $CH_3$ | CN | Cl | O | H | $CH_2C\equiv CH$ | |
| 14.24 | F | Br | $CH_3$ | CN | Cl | O | H | H | |
| 14.25 | F | CN | $CH_3$ | CN | Cl | O | H | H | |
| 14.26 | F | CN | $CH_3$ | CN | Cl | O | H | $CH_2CH_3$ | |
| 14.27 | F | Cl | $CH_3$ | CN | Br | O | H | H | |
| 14.28 | F | Cl | $CH_3$ | CN | Br | O | H | $CH_3$ | |
| 14.29 | Cl | Cl | $CH_3$ | CN | Cl | O | H | H | |
| 14.30 | Cl | Cl | $CH_3$ | CN | Cl | O | H | $CH_3$ | |
| 14.31 | Cl | Cl | $CH_3$ | CN | Cl | O | H | $CH_2CH_3$ | |
| 14.32 | Cl | Cl | $CH_3$ | CN | Cl | O | H | cyclohexyl | |
| 14.33 | Cl | Cl | $CH_3$ | CN | Cl | O | H | $CH_2CH=CH_2$ | |
| 14.34 | Cl | Cl | $CH_3$ | $CSNH_2$ | Cl | O | H | H | |
| 14.35 | Cl | Cl | $CH_3$ | $CSNH_2$ | Cl | O | H | $CH_2CH_3$ | |
| 14.36 | Cl | Cl | $CH_3$ | $CSNH_2$ | Cl | O | $CH_3$ | $CH(CH_3)_2$ | |

TABLE 15

Compounds of the formula Ip

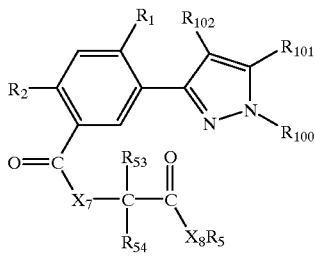

(Ip)

| Compound No. | $R_1$ | $R_2$ | $R_{100}$ | $R_{101}$ | $R_{102}$ | $X_7$ | $R_{53}$ | $R_{54}$ | $X_8$ | $R_5$ | Physical data |
|---|---|---|---|---|---|---|---|---|---|---|---|
| 15.001 | H | Cl | $CH_3$ | CN | Cl | O | $CH_3$ | $CH_3$ | O | H | solid |
| 15.002 | H | Cl | $CH_3$ | CN | Cl | O | $CH_3$ | $CH_3$ | O | $CH_3$ | 116–125° C. |
| 15.003 | H | Cl | $CH_3$ | CN | Cl | O | $CH_3$ | $CH_3$ | O | $CH_2CH_3$ | |
| 15.004 | H | Cl | $CH_3$ | CN | Cl | O | $CH_3$ | $CH_3$ | O | $CH(CH_3)_2$ | |
| 15.005 | H | Cl | $CH_3$ | CN | Cl | O | $CH_3$ | $CH_3$ | O | $CH_2CH=CH_2$ | |
| 15.006 | H | Cl | $CH_3$ | CN | Cl | O | $CH_3$ | $CH_3$ | O | $CH_2$–C$_6$H$_5$ | |
| 15.007 | F | Cl | $CH_3$ | CN | Cl | O | $CH_3$ | $CH_3$ | O | H | |
| 15.008 | F | Cl | $CH_3$ | CN | Cl | O | $CH_3$ | $CH_3$ | O | $CH_3$ | |
| 15.009 | F | Cl | $CH_3$ | CN | Cl | O | $CH_3$ | $CH_3$ | O | $CH_2CH_3$ | resin |
| 15.010 | F | Cl | $CH_3$ | CN | Cl | O | $CH_3$ | $CH_3$ | O | $CH_2CH_2CH_2CH_3$ | |
| 15.011 | F | Cl | $CH_3$ | CN | Cl | O | $CH_3$ | $CH_3$ | O | $CH(CH_3)_2$ | |
| 15.012 | F | Cl | $CH_3$ | CN | Cl | O | $CH_3$ | $CH_3$ | O | $CH(CH_2CH_3)(CH_3)$ | |
| 15.013 | F | Cl | $CH_3$ | CN | Cl | O | $CH_3$ | $CH_3$ | O | $CH_2CH=CH_2$ | |
| 15.014 | F | Cl | $CH_3$ | CN | Cl | O | $CH_3$ | $CH_3$ | O | $CH(CH_3)CH=CH_2$ (rac.) | |
| 15.015 | F | Cl | $CH_3$ | CN | Cl | O | $CH_3$ | $CH_3$ | O | $CH(CH_3)CH=CH_2$ (S) | |
| 15.016 | F | Cl | $CH_3$ | CN | Cl | O | $CH_3$ | $CH_3$ | O | $CH_2C\equiv CH$ | |
| 15.017 | F | Cl | $CH_3$ | CN | Cl | O | $CH_3$ | $CH_3$ | O | $CH_2$–C$_6$H$_5$ | |
| 15.018 | F | Cl | $CH_3$ | CN | Cl | O | $CH_3$ | $CH_3$ | O | $CH_2CH_2OCH_3$ | |
| 15.019 | F | Cl | $CH_3$ | CN | Cl | O | $CH_3$ | $CH_3$ | O | $CH(CH_3)CH_2SCH_2CH_3$ | |
| 15.020 | F | Cl | $CH_3$ | CN | Cl | O | $CH_3$ | $CH_3$ | O | cyclohexyl | |
| 15.021 | F | Cl | $CH_3$ | CN | Cl | O | $CH_3$ | $CH_3$ | O | $CH(CH_2CH_3)CH=CH_2$ | |
| 15.022 | F | Cl | $CH_3$ | CN | Cl | O | $CH_3$ | $CH_3$ | O | $CH_2CH_2N(CH_3)_2$ | |
| 15.023 | F | Cl | $CH_3$ | CN | Cl | O | $CH_3$ | $CH_3$ | O | $CH_2CH_2CN$ | |
| 15.024 | F | Cl | $CH_3$ | CN | Cl | O | $CH_3$ | $CH_3$ | O | $CH_3$ | |
| 15.025 | F | Cl | $CH_3$ | CN | Cl | O | $CH_3$ | $CH_3$ | O | $CH_2CH_3$ | |
| 15.026 | F | Cl | $CH_3$ | CN | Cl | O | $CH_3$ | $CH_3$ | O | $CH(CH_3)_2$ | |
| 15.027 | F | Cl | $CH_3$ | CN | Br | O | $CH_3$ | $CH_3$ | O | H | |
| 15.028 | F | Cl | $CH_3$ | CN | Br | O | $CH_3$ | $CH_3$ | O | $CH_3$ | |
| 15.029 | F | Cl | $CH_3$ | CN | Br | O | $CH_3$ | $CH_3$ | O | $CH_2CH_3$ | |
| 15.030 | F | Cl | $CH_3$ | CN | Br | O | $CH_3$ | $CH_3$ | O | $CH(CH_3)_2$ | |
| 15.031 | F | Cl | $CH_3$ | CN | Br | O | $CH_3$ | $CH_3$ | O | $CH_2CH=CH_2$ | resin |
| 15.032 | F | Cl | $CH_3$ | CN | Br | O | $CH_3$ | $CH_3$ | O | $CH(CH_3)CH=CH_2$ | |
| 15.033 | F | Cl | $CH_3$ | CN | Br | O | $CH_3$ | $CH_3$ | O | $CH_2$–C$_6$H$_5$ | resin |
| 15.034 | F | Br | $CH_3$ | CN | Cl | O | $CH_3$ | $CH_3$ | O | H | |
| 15.035 | F | Br | $CH_3$ | CN | Cl | O | $CH_3$ | $CH_3$ | O | $CH_3$ | |
| 15.036 | F | Br | $CH_3$ | CN | Cl | O | $CH_3$ | $CH_3$ | O | $CH_2CH_3$ | |
| 15.037 | F | Br | $CH_3$ | CN | Cl | O | $CH_3$ | $CH_3$ | O | $CH_2CH=CH_2$ | |

TABLE 15-continued

Compounds of the formula Ip

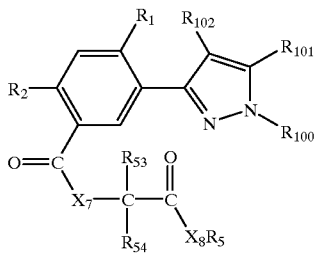

(Ip)

| Compound No. | $R_1$ | $R_2$ | $R_{100}$ | $R_{101}$ | $R_{102}$ | $X_7$ | $R_{53}$ | $R_{54}$ | $X_8$ | $R_5$ | Physical data |
|---|---|---|---|---|---|---|---|---|---|---|---|
| 15.038 | F | Br | $CH_3$ | CN | Cl | O | $CH_3$ | $CH_3$ | O | $CH(CH_3)CH=CH_2$ (rac.) | |
| 15.039 | F | Br | $CH_3$ | CN | Cl | O | $CH_3$ | $CH_3$ | O | $CH(CH_3)CH=CH_2$ (S) | |
| 15.040 | F | Br | $CH_3$ | CN | Cl | O | $CH_3$ | $CH_3$ | O | $CH_2C\equiv CH$ | |
| 15.041 | F | Br | $CH_3$ | CN | Cl | O | $CH_3$ | $CH_3$ | O | $CH_2$–phenyl | |
| 15.042 | F | CN | $CH_3$ | CN | Cl | O | $CH_3$ | $CH_3$ | O | H | |
| 15.043 | F | CN | $CH_3$ | CN | Cl | O | $CH_3$ | $CH_3$ | O | $CH_2CH_3$ | |
| 15.044 | F | CN | $CH_3$ | CN | Cl | O | $CH_3$ | $CH_3$ | O | $CH_2CH=CH_2$ | |
| 15.045 | F | CN | $CH_3$ | CN | Cl | O | $CH_3$ | $CH_3$ | O | $CH(CH_3)CH=CH_2$ | |
| 15.046 | F | Cl | $CH_3$ | $CSNH_2$ | Cl | O | $CH_3$ | $CH_3$ | O | H | |
| 15.047 | F | Cl | $CH_3$ | $CSNH_2$ | Cl | O | $CH_3$ | $CH_3$ | O | $CH_2CH_3$ | |
| 15.048 | F | Cl | $CH_3$ | $CSNH_2$ | Cl | O | $CH_3$ | $CH_3$ | O | $CH_2CH=CH_2$ | |
| 15.049 | F | Cl | $CH_3$ | $CSNH_2$ | Cl | O | $CH_3$ | $CH_3$ | O | $CH(CH_3)CH=CH_2$ (rac.) | |
| 15.050 | F | Cl | $CH_3$ | $CSNH_2$ | Cl | O | $CH_3$ | $CH_3$ | O | $CH(CH_3)CH=CH_2$ (S) | |
| 15.051 | F | Cl | $CH_3$ | $CSNH_2$ | Cl | O | $CH_3$ | $CH_3$ | O | $CH_2$–phenyl | |
| 15.052 | F | Cl | $CH_3$ | $CSNH_2$ | Cl | O | $CH_3$ | $CH_3$ | O | $CH_2CH_2N(CH_3)_2$ | |
| 15.053 | F | Cl | $CH_3$ | $CSNH_2$ | Cl | O | $CH_3$ | $CH_3$ | S | $CH_2CH_3$ | |
| 15.054 | F | Cl | $CH_3$ | $CSNH_2$ | Br | O | $CH_3$ | $CH_3$ | O | $CH_2CH=CH_2$ | resin |
| 15.055 | F | Cl | $CH_3$ | $CSNH_2$ | Br | O | $CH_3$ | $CH_3$ | O | $CH_2$–phenyl | |
| 15.056 | F | Br | $CH_3$ | CN | Br | O | $CH_3$ | $CH_3$ | O | $CH_2CH=CH_2$ | |
| 15.057 | F | Br | $CH_3$ | $CSNH_2$ | Br | O | $CH_3$ | $CH_3$ | O | $CH_2CH_3$ | |
| 15.058 | F | CN | $CH_3$ | CN | Br | O | $CH_3$ | $CH_3$ | O | $CH_2CH=CH_2$ | |
| 15.059 | Cl | Cl | $CH_3$ | CN | Cl | O | $CH_3$ | $CH_3$ | O | H | |
| 15.060 | Cl | Cl | $CH_3$ | CN | Cl | O | $CH_3$ | $CH_3$ | O | $CH_3$ | |
| 15.061 | Cl | Cl | $CH_3$ | CN | Cl | O | $CH_3$ | $CH_3$ | O | $CH_2CH_3$ | resin |
| 15.062 | Cl | Cl | $CH_3$ | CN | Cl | O | $CH_3$ | $CH_3$ | O | $CH_2CH_2CH_2CH_2CH_3$ | |
| 15.063 | Cl | Cl | $CH_3$ | CN | Cl | O | $CH_3$ | $CH_3$ | O | $CH(CH_3)_2$ | |
| 15.064 | Cl | Cl | $CH_3$ | CN | Cl | O | $CH_3$ | $CH_3$ | O | $CH_2CH=CH_2$ | |
| 15.065 | Cl | Cl | $CH_3$ | CN | Cl | O | $CH_3$ | $CH_3$ | O | $CH(CH_3)CH=CH_2$ (rac.) | |
| 15.066 | Cl | Cl | $CH_3$ | CN | Cl | O | $CH_3$ | $CH_3$ | O | $CH(CH_3)CH=CH_2$ (S) | |
| 15.067 | Cl | Cl | $CH_3$ | CN | Cl | O | $CH_3$ | $CH_3$ | O | $CH_2$–phenyl | |
| 15.068 | Cl | Cl | $CH_3$ | CN | Cl | O | $CH_3$ | $CH_3$ | O | $CH_2CH_2OCH_3$ | |
| 15.069 | Cl | Cl | $CH_3$ | CN | Cl | O | $CH_3$ | $CH_3$ | O | $CH(CH_3)CH_2SCH_2CH_3$ | |
| 15.070 | Cl | Br | $CH_3$ | CN | Cl | O | $CH_3$ | $CH_3$ | O | $CH_2CH_3$ | |
| 15.071 | Cl | CN | $CH_3$ | CN | Cl | O | $CH_3$ | $CH_3$ | O | $CH_2CH=CH_2$ | |
| 15.072 | Cl | Cl | $CH_3$ | CN | Br | O | $CH_3$ | $CH_3$ | O | $CH_3$ | |
| 15.073 | Cl | Cl | $CH_3$ | $CSNH_2$ | Cl | O | $CH_3$ | $CH_3$ | O | H | |
| 15.074 | Cl | Cl | $CH_3$ | $CSNH_2$ | Cl | O | $CH_3$ | $CH_3$ | O | $CH_2CH_3$ | |

TABLE 15-continued

Compounds of the formula Ip

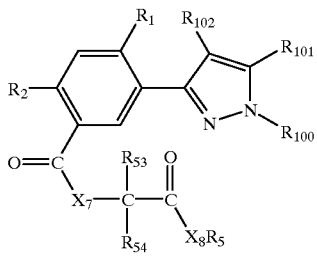

(Ip)

| Compound No. | $R_1$ | $R_2$ | $R_{100}$ | $R_{101}$ | $R_{102}$ | $X_7$ | $R_{53}$ | $R_{54}$ | $X_8$ | $R_5$ | Physical data |
|---|---|---|---|---|---|---|---|---|---|---|---|
| 15.075 | Cl | Cl | $CH_3$ | $CSNH_2$ | Cl | O | $CH_3$ | $CH_3$ | O | $CH_2CH=CH_2$ | |
| 15.076 | Cl | Cl | $CH_3$ | $CSNH_2$ | Cl | O | $CH_3$ | $CH_3$ | O | $CH(CH_3)CH=CH_2$ | |
| 15.077 | Cl | Cl | $CH_3$ | $CSNH_2$ | Cl | O | $CH_3$ | $CH_3$ | O | $CH_2$—C$_6$H$_5$ | |
| 15.078 | Cl | Br | $CH_3$ | $CSNH_2$ | Cl | O | $CH_3$ | $CH_3$ | O | $CH_2CH_2OCH_3$ | |
| 15.079 | H | Cl | $CH_3$ | CN | Cl | O | H | H | O | $CH_2CH_3$ | |
| 15.080 | F | Cl | $CH_3$ | CN | Cl | O | H | H | O | H | |
| 15.081 | F | Cl | $CH_3$ | CN | Cl | O | H | H | O | $CH_2CH_3$ | |
| 15.082 | F | Cl | $CH_3$ | CN | Cl | O | H | H | O | $CH_2CH=CH_2$ | |
| 15.083 | F | Cl | $CH_3$ | CN | Cl | O | H | H | O | $CH_2$—C$_6$H$_5$ | |
| 15.084 | F | Cl | $CH_3$ | $CSNH_2$ | Cl | O | H | H | O | $CH_2CH_3$ | |
| 15.085 | Cl | Cl | $CH_3$ | CN | Cl | O | H | H | O | $CH_3$ | |
| 15.086 | Cl | Cl | $CH_3$ | CN | Cl | O | H | H | O | $CH(CH_3)_2$ | |
| 15.087 | Cl | Cl | $CH_3$ | $CSNH_2$ | Cl | O | H | H | O | $CH_2CH=CH_2$ | |
| 15.088 | H | Cl | $CH_3$ | CN | Cl | O | H | $CH_3$ | O | H | |
| 15.089 | H | Cl | $CH_3$ | CN | Cl | O | H | $CH_3$ | O | $CH_2CH_3$ | |
| 15.090 | H | Cl | $CH_3$ | CN | Cl | O | H | $CH_3$ | O | $CH_2$—C$_6$H$_5$ | |
| 15.091 | F | Cl | $CH_3$ | CN | Cl | O | H | $CH_3$ | O | H | |
| 15.092 | F | Cl | $CH_3$ | CN | Cl | O | H | $CH_3$ | O | $CH_3$ | |
| 15.093 | F | Cl | $CH_3$ | CN | Cl | O | H | $CH_3$ | O | $CH_2CH_3$ | |
| 15.094 | F | Cl | $CH_3$ | CN | Cl | O | H | $CH_3$ | O | $CH_2CH_2CH_2CH_3$ | |
| 15.095 | F | Cl | $CH_3$ | CN | Cl | O | H | $CH_3$ | O | $CH_2CH=CH_2$ (rac.) | |
| 15.096 | F | Cl | $CH_3$ | CN | Cl | O | H | $CH_3$ | O | $CH_2CH=CH_2$ (S) | |
| 15.097 | F | Cl | $CH_3$ | CN | Cl | O | H | $CH_3$ | O | $CH(CH_3)CH=CH_2$ | |
| 15.098 | F | Cl | $CH_3$ | CN | Cl | O | H | $CH_3$ | O | $CH(CH_3)_2$ | |
| 15.099 | F | Cl | $CH_3$ | CN | Cl | O | H | $CH_3$ | O | $CH_2C\equiv CH$ | |
| 15.100 | F | Cl | $CH_3$ | CN | Cl | O | H | $CH_3$ | O | $CH_2CH_2N(CH_2CH_3)_2$ | |
| 15.101 | F | Cl | $CH_3$ | CN | Cl | O | H | $CH_3$ | O | $CH_2$—C$_6$H$_5$ | |
| 15.102 | F | Cl | $CH_3$ | CN | Cl | O | H | $CH_3$ | O | $CH(CH_3)CH_2SCH_3$ | |
| 15.103 | F | Cl | $CH_3$ | CN | Cl | O | H | $CH_3$ | S | $CH_2CH_3$ | |
| 15.104 | F | Br | $CH_3$ | CN | Cl | O | H | $CH_3$ | O | H (rac.) | |
| 15.105 | F | Br | $CH_3$ | CN | Cl | O | H | $CH_3$ | O | H (S) | |
| 15.106 | F | Br | $CH_3$ | CN | Cl | O | H | $CH_3$ | O | $CH_2CH_3$ | |
| 15.107 | F | Br | $CH_3$ | CN | Cl | O | H | $CH_3$ | O | $CH_2CH=CH_2$ | |
| 15.108 | F | CN | $CH_3$ | CN | Cl | O | H | $CH_3$ | O | $CH(CH_3)_2$ | |
| 15.109 | F | CN | $CH_3$ | CN | Cl | O | H | $CH_3$ | O | $CH_2CH_3$ | |
| 15.110 | F | Cl | $CH_3$ | CN | Br | O | H | $CH_3$ | O | $CH_3$ | |
| 15.111 | F | Cl | $CH_3$ | $CSNH_2$ | Cl | O | H | $CH_3$ | O | H (rac.) | |

TABLE 15-continued

Compounds of the formula Ip

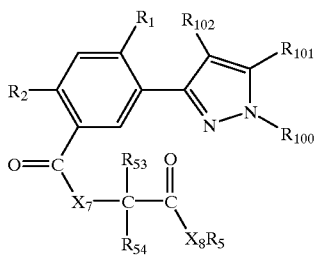

(Ip)

| Compound No. | $R_1$ | $R_2$ | $R_{100}$ | $R_{101}$ | $R_{102}$ | $X_7$ | $R_{53}$ | $R_{54}$ | $X_8$ | $R_5$ | Physical data |
|---|---|---|---|---|---|---|---|---|---|---|---|
| 15.112 | F | Cl | $CH_3$ | $CSNH_2$ | Cl | O | H | $CH_3$ | O | H (S) | |
| 15.113 | F | Cl | $CH_3$ | $CSNH_2$ | Cl | O | H | $CH_3$ | O | $CH_3$ | |
| 15.114 | F | Cl | $CH_3$ | $CSNH_2$ | Cl | O | H | $CH_3$ | O | $CH_2CH_3$ | |
| 15.115 | F | Cl | $CH_3$ | $CSNH_2$ | Cl | O | H | $CH_3$ | O | $CH_2CH=CH_2$ | |
| 15.116 | F | Cl | $CH_3$ | $CSNH_2$ | Cl | O | H | $CH_3$ | O | $CH_2$-C$_6$H$_5$ | |
| 15.117 | F | Cl | $CH_3$ | $CSNH_2$ | Br | O | H | $CH_3$ | O | $CH(CH_3)_2$ | |
| 15.118 | F | Br | $CH_3$ | $CSNH_2$ | Cl | O | H | $CH_3$ | O | $CH_2CH_3$ | |
| 15.119 | Cl | Cl | $CH_3$ | CN | Cl | O | H | $CH_3$ | O | H | |
| 15.120 | Cl | Cl | $CH_3$ | CN | Cl | O | H | $CH_3$ | O | $CH_2CH_3$ | resin |
| 15.121 | Cl | Cl | $CH_3$ | CN | Cl | O | H | $CH_3$ | O | $CH_2CH=CH_2$ | |
| 15.122 | Cl | Cl | $CH_3$ | CN | Cl | O | H | $CH_3$ | O | $CH(CH_3)CH=CH_2$ | |
| 15.123 | Cl | Cl | $CH_3$ | CN | Cl | O | H | $CH_3$ | O | $CH(CH_3)_2$ | |
| 15.124 | Cl | Cl | $CH_3$ | CN | Cl | O | H | $CH_3$ | S | $CH_2CH_3$ | |
| 15.125 | Cl | Cl | $CH_3$ | $CSNH_2$ | Cl | O | H | $CH_3$ | O | H | |
| 15.126 | Cl | Cl | $CH_3$ | $CSNH_2$ | Cl | O | H | $CH_3$ | O | $CH_2CH_3$ | |
| 15.127 | Cl | Cl | $CH_3$ | $CSNH_2$ | Cl | O | H | $CH_3$ | O | $CH_2$-C$_6$H$_5$ | |
| 15.128 | Cl | Cl | $CH_3$ | $CSNH_2$ | Br | O | H | $CH_3$ | O | $CH_2CH=CH_2$ | |
| 15.129 | F | Cl | $CH_3$ | CN | Cl | S | $CH_3$ | $CH_3$ | O | $CH_2CH=CH_2$ | |
| 15.130 | F | Cl | $CH_3$ | CN | Cl | S | $CH_3$ | $CH_3$ | O | $CH(CH_3)CH_2CH_3$ | |
| 15.131 | F | Cl | $CH_3$ | CN | Br | S | $CH_3$ | $CH_3$ | O | $CH_3$ | |
| 15.132 | F | Cl | $CH_3$ | CN | Cl | S | H | $CH_3$ | O | $CH_2CH_3$ | |
| 15.133 | F | Cl | $CH_3$ | CN | Br | S | H | $CH_3$ | O | $CH_2$-C$_6$H$_5$ | |
| 15.134 | F | Cl | $CH_3$ | CN | Br | S | H | $CH_3$ | O | H | |
| 15.135 | F | Cl | $CH_3$ | $CSNH_2$ | Cl | S | H | H | O | $CH_2CH_2CH_2CH_3$ | |
| 15.136 | F | Cl | $CH_3$ | $CSNH_2$ | Br | S | H | H | O | $CH_2CH=CH_2$ | |
| 15.137 | F | Cl | $CH_3$ | CN | Cl | NH | $CH_3$ | $CH_3$ | O | H | |
| 15.138 | F | Cl | $CH_3$ | CN | Cl | NH | $CH_3$ | $CH_3$ | O | $CH_2CH_3$ | |
| 15.139 | F | Cl | $CH_3$ | CN | Cl | NH | $CH_3$ | $CH_3$ | O | $CH(CH_3)CH=CH_2$ | |
| 15.140 | F | Cl | $CH_3$ | $CSNH_2$ | Cl | NH | $CH_3$ | $CH_3$ | O | $CH_3$ | |
| 15.141 | F | Cl | $CH_3$ | CN | Br | NH | $CH_3$ | $CH_3$ | O | $CH_2$-C$_6$H$_5$ | |
| 15.142 | F | Cl | $CH_3$ | CN | Cl | NH | H | $CH_3$ | O | H | |
| 15.143 | F | Cl | $CH_3$ | CN | Cl | NH | H | $CH_3$ | O | $CH(CH_3)_2$ | |
| 15.144 | F | Cl | $CH_3$ | CN | Br | NH | H | $CH_3$ | O | $CH_2CH_3$ | |
| 15.145 | Cl | Cl | $CH_3$ | CN | Cl | NH | H | $CH_3$ | O | $CH_2CH=CH_2$ | |
| 15.146 | Cl | Cl | $CH_3$ | $CSNH_2$ | Cl | NH | H | $CH_3$ | O | $CH_3$ | |
| 15.147 | F | Cl | $CH_3$ | CN | Cl | NH | H | H | O | H | |
| 15.148 | F | Cl | $CH_3$ | CN | Cl | NH | H | H | O | $CH_2CH_3$ | |

TABLE 15-continued

Compounds of the formula Ip

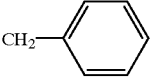

(Ip)

| Compound No. | $R_1$ | $R_2$ | $R_{100}$ | $R_{101}$ | $R_{102}$ | $X_7$ | $R_{53}$ | $R_{54}$ | $X_8$ | $R_5$ | Physical data |
|---|---|---|---|---|---|---|---|---|---|---|---|
| 15.149 | F | Cl | $CH_3$ | CN | Cl | NH | H | H | O | $CH(CH_3)_2$ | |
| 15.150 | F | Cl | $CH_3$ | $CSNH_2$ | Cl | NH | H | H | O | $CH_2CH\!=\!CH_2$ | |
| 15.151 | F | Cl | $CH_3$ | $CSNH_2$ | Cl | NH | H | H | O | $CH_3$ | |
| 15.152 | Cl | Cl | $CH_3$ | CN | Cl | NH | H | H | O | $CH_2CH_2CH_3$ | |
| 15.153 | Cl | Cl | $CH_3$ | CN | Cl | NH | H | H | |  | |
| 15.154 | F | Cl | $CH_3$ | CN | Cl | $N(CH_3)$ | H | H | O | H | |
| 15.155 | F | Cl | $CH_3$ | CN | Cl | $N(CH_2CH\!=\!CH_2)$ | H | $CH_3$ | O | $CH_2CH_3$ | |
| 15.156 | F | Cl | $CH_3$ | CN | Cl | NH | H | $CH(CH_3)_2$ | O | $CH_3$ | |
| 15.157 | F | Cl | $CH_3$ | CN | Cl | O |  | | O | $CH_2CH\!=\!CH_2$ | |
| 15.158 | F | Cl | $CH_3$ | CN | Cl | O |  | | O | $CH_2CH_3$ | |
| 15.159 | F | Cl | $CH_3$ | CN | Br | O | 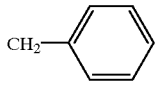 | | O |  | |
| 15.160 | F | Cl | $CH_3$ | $CSNH_2$ | Cl | O | | | O | $CH_3$ | |
| 15.161 | F | Cl | $CH_3$ | CN | Cl | O | H | $CH_2CH_2CH_3$ | O | $CH_2CH\!=\!CH_2$ | |
| 15.162 | F | Br | $CH_3$ | CN | Cl | O | H | $CH_2CH\!=\!CH_2$ | O | $CH_3$ | |
| 15.163 | F | Cl | $CH_3$ | CN | Cl | S | H | H | O | $CH_2CH_3$ | 75–77° C. |

TABLE 16

Compounds of the formula Iq

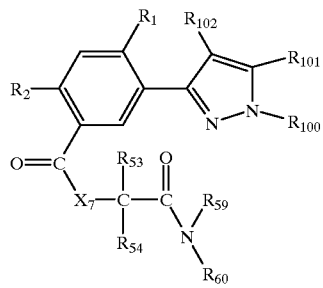

(Iq)

| Compound No. | $R_1$ | $R_2$ | $R_{100}$ | $R_{101}$ | $R_{102}$ | $X_7$ | $R_{53}$ | $R_{54}$ | $R_{59}$ | $R_{60}$ | Physical data |
|---|---|---|---|---|---|---|---|---|---|---|---|
| 16.001 | H | Cl | $CH_3$ | CN | Cl | O | $CH_3$ | $CH_3$ | H | H | |
| 16.002 | H | Cl | $CH_3$ | CN | Cl | O | H | $CH_3$ | H | $CH_2CH=CH_2$ | |
| 16.003 | F | Cl | $CH_3$ | CN | Cl | O | $CH_3$ | $CH_3$ | H | $CH_2CH=CH_2$ | |
| 16.004 | F | Cl | $CH_3$ | CN | Cl | O | $CH_3$ | $CH_3$ | $CH_2CH=CH_2$ | $CH_2CH=CH_2$ | |
| 16.005 | F | Cl | $CH_3$ | CN | Cl | O | $CH_3$ | $CH_3$ | $CH_3$ | $CH_3$ | |
| 16.006 | F | Cl | $CH_3$ | $CSNH_2$ | Cl | O | $CH_3$ | $CH_3$ | H | $CH_2$–phenyl | |
| 16.007 | F | Cl | $CH_3$ | $CSNH_2$ | Cl | O | $CH_3$ | $CH_3$ | $CH_2CH=CH_2$ | $CH_2$–phenyl | |
| 16.008 | F | Cl | $CH_3$ | $CSNH_2$ | Cl | O | $CH_3$ | $CH_3$ | H | 4-methylphenyl | |
| 16.009 | F | Cl | $CH_3$ | CN | Cl | O | $CH_3$ | $CH_3$ | \multicolumn{2}{c|}{pyrrolidinyl} | |
| 16.010 | F | Cl | $CH_3$ | CN | Br | O | $CH_3$ | $CH_3$ | \multicolumn{2}{c|}{morpholinyl} | |
| 16.011 | F | Cl | $CH_3$ | CN | Cl | O | $CH_3$ | $CH_3$ | H | H | |
| 16.012 | F | Cl | $CH_3$ | CN | Cl | O | $CH_3$ | $CH_3$ | H | $CH_2CH_3$ | |
| 16.013 | F | Cl | $CH_3$ | CN | Br | O | $CH_3$ | $CH_3$ | H | $CH_2CH=CH_2$ | |
| 16.014 | F | Cl | $CH_3$ | CN | Br | O | $CH_3$ | $CH_3$ | H | $CH_2$–phenyl | |
| 16.015 | F | Cl | $CH_3$ | $CSNH_2$ | Cl | O | $CH_3$ | $CH_3$ | H | H | |
| 16.016 | F | Cl | $CH_3$ | $CSNH_2$ | Cl | O | $CH_3$ | $CH_3$ | H | $CH_3$ | |
| 16.017 | F | Cl | $CH_3$ | $CSNH_2$ | Cl | O | $CH_3$ | $CH_3$ | $CH_2CH_3$ | $CH_2CH_3$ | |
| 16.018 | F | Cl | $CH_3$ | $CSNH_2$ | Cl | O | $CH_3$ | $CH_3$ | H | $CH_2CH=CH_2$ | |
| 16.019 | F | Cl | $CH_3$ | $CSNH_2$ | Cl | O | $CH_3$ | $CH_3$ | H | $CH_2$–(4-Cl-phenyl) | |
| 16.020 | F | Cl | $CH_3$ | $CSNH_2$ | Cl | O | $CH_3$ | $CH_3$ | \multicolumn{2}{c|}{morpholinyl} | |

TABLE 16-continued

Compounds of the formula Iq

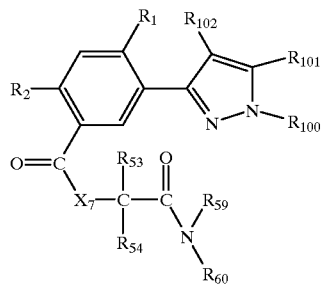

(Iq)

| Compound No. | $R_1$ | $R_2$ | $R_{100}$ | $R_{101}$ | $R_{102}$ | $X_7$ | $R_{53}$ | $R_{54}$ | $R_{59}$ | $R_{60}$ | Physical data |
|---|---|---|---|---|---|---|---|---|---|---|---|
| 16.021 | Cl | Cl | $CH_3$ | CN | Cl | O | $CH_3$ | $CH_3$ | H | H | |
| 16.022 | Cl | Cl | $CH_3$ | CN | Cl | O | $CH_3$ | $CH_3$ | H | $CH_3$ | |
| 16.023 | Cl | Cl | $CH_3$ | CN | Cl | O | $CH_3$ | $CH_3$ | \multicolumn{2}{c}{pyrrolidinyl} | |
| 16.024 | Cl | Cl | $CH_3$ | CN | Cl | O | $CH_3$ | $CH_3$ | H | $CH_2CH=CH_2$ | |
| 16.025 | Cl | Cl | $CH_3$ | $CSNH_2$ | Cl | O | $CH_3$ | $CH_3$ | H | $CH_2CH_3$ | |
| 16.026 | Cl | Cl | $CH_3$ | $CSNH_2$ | Cl | O | $CH_3$ | $CH_3$ | H | $CH_2$-Ph | |
| 16.027 | F | Br | $CH_3$ | CN | Cl | O | $CH_3$ | $CH_3$ | H | $CH_3C{\equiv}CH$ | |
| 16.028 | F | Br | $CH_3$ | CN | Cl | O | $CH_3$ | $CH_3$ | $CH_3$ | $CH_2$-Ph | |
| 16.029 | F | Cl | $CH_3$ | CN | Cl | O | H | $CH_3$ | H | $CH_3$ | |
| 16.030 | F | Cl | $CH_3$ | CN | Cl | O | H | $CH_3$ | $CH_3$ | $CH_3$ | |
| 16.031 | F | Cl | $CH_3$ | CN | Cl | O | H | $CH_3$ | H | $CH_2CH=CH_2$ | |
| 16.032 | F | Cl | $CH_3$ | CN | Cl | O | H | $CH_3$ | \multicolumn{2}{c}{aziridinyl} | |
| 16.033 | F | Cl | $CH_3$ | $CSNH_2$ | Cl | O | H | $CH_3$ | H | $CH_2CH=CH_2$ | |
| 16.034 | F | Cl | $CH_3$ | $CSNH_2$ | Cl | O | H | $CH_3$ | H | H | |
| 16.035 | Cl | Cl | $CH_3$ | CN | Cl | O | H | $CH_3$ | H | $CH_2$-Ph | |
| 16.036 | Cl | Cl | $CH_3$ | CN | Cl | O | H | $CH_3$ | \multicolumn{2}{c}{morpholinyl} | |
| 16.037 | F | Cl | $CH_3$ | CN | Cl | O | H | H | H | $CH_2CH_3$ | |
| 16.038 | F | Cl | $CH_3$ | CN | Cl | O | H | H | \multicolumn{2}{c}{piperidinyl} | |
| 16.039 | F | Cl | $CH_3$ | $CSNH_2$ | Cl | O | H | H | H | $CH_2CH_2CH_2CH_3$ | |

TABLE 16-continued

Compounds of the formula Iq

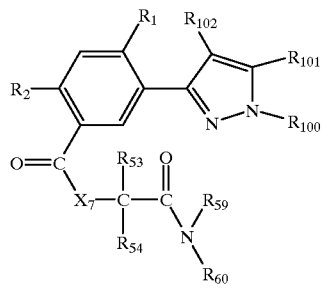

(Iq)

| Compound No. | $R_1$ | $R_2$ | $R_{100}$ | $R_{101}$ | $R_{102}$ | $X_7$ | $R_{53}$ | $R_{54}$ | $R_{59}$ | $R_{60}$ | Physical data |
|---|---|---|---|---|---|---|---|---|---|---|---|
| 16.040 | F | Cl | $CH_3$ | $CSNH_2$ | Br | O | H | H | H | $CH_2$-phenyl | |
| 16.041 | Cl | Cl | $CH_3$ | CN | Cl | O | H | H | H | $CH_2CH_3$ | |
| 16.042 | Cl | Cl | $CH_3$ | CN | Cl | O | H | H | $CH_2CH=CH_2$ | $CH_2CH=CH_2$ | |
| 16.043 | Cl | Cl | $CH_3$ | $CSNH_2$ | Cl | O | H | H | H | $CH_2$-phenyl | |
| 16.044 | F | Cl | $CH_3$ | CN | Cl | S | H | $CH_3$ | H | $CH_3$ | |
| 16.045 | F | Cl | $CH_3$ | CN | Cl | S | H | H | H | $CH_2CH=CH_2$ | |
| 16.046 | F | Cl | $CH_3$ | CN | Br | S | H | $CH_3$ | morpholino | | |
| 16.047 | Cl | Cl | $CH_3$ | CN | Cl | S | H | H | H | $CH(CH_3)_2$ | |
| 16.048 | Cl | Cl | $CH_3$ | CN | Cl | S | H | H | $CH_3$ | $CH_3$ | |
| 16.049 | F | Cl | $CH_3$ | CN | Cl | NH | $CH_3$ | $CH_3$ | H | H | |
| 16.050 | F | Cl | $CH_3$ | CN | Cl | NH | $CH_3$ | $CH_3$ | aziridinyl | | |
| 16.051 | F | Cl | $CH_3$ | CN | Cl | NH | $CH_3$ | $CH_3$ | H | $CH_2CH_3$ | |
| 16.052 | F | Cl | $CH_3$ | CN | Cl | $N(CH_3)$ | $CH_3$ | $CH_3$ | H | $CH_2CH=CH_2$ | |
| 16.053 | F | Cl | $CH_3$ | CN | Cl | NH | H | $CH_3$ | H | $CH_3$ | |
| 16.054 | F | Cl | $CH_3$ | $CSNH_2$ | Cl | NH | H | $CH_3$ | $CH_3$ | $CH_2CH=CH_2$ | |
| 16.055 | F | Br | $CH_3$ | CN | Cl | NH | H | $CH_3$ | H | $CH_2CH=CH_2$ | |
| 16.056 | Cl | Cl | $CH_3$ | CN | Cl | NH | $CH_3$ | $CH_3$ | H | $CH_2CH=CH_2$ | |
| 16.057 | Cl | Cl | $CH_3$ | CN | Cl | NH | $CH_3$ | $CH_3$ | $CH_2CH_3$ | $CH_2CH_3$ | |
| 16.058 | Cl | Cl | $CH_3$ | CN | Cl | $N(CH_2CH=CH_2)$ | $CH_3$ | $CH_3$ | H | $CH_3$ | |
| 16.059 | Cl | Cl | $CH_3$ | CN | Cl | NH | H | $CH_3$ | H | $CH(CH_3)_2$ | |
| 16.060 | Cl | Cl | $CH_3$ | CN | Cl | NH | H | $CH_3$ | H | H | |
| 16.061 | Cl | Cl | $CH_3$ | CN | Cl | NH | H | H | H | $CH_2$-phenyl | |
| 16.062 | Cl | Cl | $CH_3$ | CN | Cl | $N(CH_2)$ | H | H | piperidino | | |
| 16.063 | Cl | Cl | $CH_3$ | CN | Cl | NH | H | H | H | $CH_2CH_2CH_3$ | |
| 16.064 | Cl | Cl | $CH_3$ | $CSNH_2$ | Cl | NH | H | H | $CH_3$ | $CH_3$ | |
| 16.065 | F | Cl | $CH_3$ | CN | Cl | NH | H | H | H | H | |

TABLE 16-continued

Compounds of the formula Iq

(Iq)

| Compound No. | $R_1$ | $R_2$ | $R_{100}$ | $R_{101}$ | $R_{102}$ | $X_7$ | $R_{53}$ | $R_{54}$ | $R_{59}$ | $R_{60}$ | Physical data |
|---|---|---|---|---|---|---|---|---|---|---|---|
| 16.066 | F | Br | $CH_3$ | CN | Cl | NH | H | H |  | | |
| 16.067 | F | Cl | $CH_3$ | $CSNH_2$ | Cl | $N(CH_3)$ | H | H | H | $CH_2CH=CH_2$ | |
| 16.068 | F | Cl | $CH_3$ | $CSNH_2$ | Cl | NH | H | H | H | $CH_3$ | |
| 16.069 | F | Cl | $CH_3$ | CN | Cl | NH | H | $CH(CH_3)_2$ | H | $CH_3$ | |
| 16.070 | F | Cl | $CH_3$ | $CSNH_2$ | Cl | $N(CH_3)$ | H | $CH(CH_3)_2$ | $CH_2CH_3$ | $CH_2CH_3$ | |
| 16.071 | F | Cl | $CH_3$ | CN | Cl | O |  | H | $CH_2CH=CH_2$ | | |
| 16.072 | F | Cl | $CH_3$ | CN | Br | O |  | $CH_3$ | $CH_3$ | | |
| 16.073 | F | Br | $CH_3$ | $CSNH_2$ | Cl | O | H | $CH_2CH=CH_2$ |  | | |
| 16.074 | F | Cl | $CH_3$ | CN | Cl | S |  | H | $CH_2CH_3$ | | |
| 16.075 | F | Cl | $CH_3$ | CN | Cl | O | 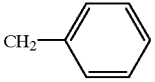 | $CH_3$ | $CH_3$ | | |
| 16.076 | F | Cl | $CH_3$ | CN | Cl | O | H | $CH_2CH_3$ | H |  | |
| 16.077 | F | Cl | $CH_3$ | CN | Cl | O | H | $CCl_3$ | H | $CH_3$ | |
| 16.078 | F | Cl | $CH_3$ | CN | Cl | O | H | $CH_2Cl$ | $CH_3$ | $CH_3$ | |
| 16.079 | F | Cl | $CH_3$ | CN | Cl | O | H | $CF_3$ | H | $CH_2CH=CH_2$ | |

TABLE 17

Compounds of the formula Ir

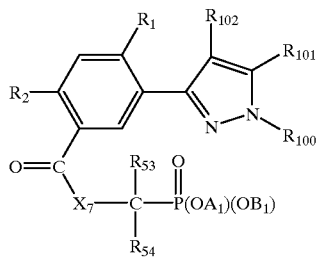

(Ir)

| Compound No. | $R_1$ | $R_2$ | $R_{100}$ | $R_{101}$ | $R_{102}$ | $X_7$ | $R_{53}$ | $R_{54}$ | $A_1$ | $B_1$ | Physical data |
|---|---|---|---|---|---|---|---|---|---|---|---|
| 17.001 | F | Cl | $CH_3$ | CN | Cl | O | H | H | H | H | |
| 17.002 | F | Cl | $CH_3$ | CN | Cl | O | H | $CH_3$ | H | H | |
| 17.003 | F | Cl | $CH_3$ | CN | Cl | O | H | $CCl_3$ | H | H | |
| 17.004 | F | Cl | $CH_3$ | $CSNH_2$ | Cl | O | H | $CH_2CH_3$ | H | H | |
| 17.005 | F | Cl | $CH_3$ | $CSNH_2$ | Cl | O | $CH_3$ | $CH_3$ | H | H | |
| 17.006 | F | Cl | $CH_3$ | CN | Br | O | $CH_3$ | $CH_2CH_3$ | H | H | |
| 17.007 | F | Cl | $CH_3$ | CN | Cl | NH | H | H | H | H | |
| 17.008 | F | Cl | $CH_3$ | $CSNH_2$ | Cl | $N(CH_3)$ | H | H | H | H | |
| 17.009 | F | Br | $CH_3$ | CN | Cl | NH | H | $CH_3$ | H | H | |
| 17.010 | F | Cl | $CH_3$ | CN | Cl | NH | $CH_3$ | $CH_3$ | H | H | |
| 17.011 | F | Cl | $CH_3$ | $CSNH_2$ | Cl | $N(CH_3)$ | H | $CH_2CH_3$ | H | H | |
| 17.012 | F | Cl | $CH_3$ | CN | Cl | O | $CH_3$ | $CH_3$ | H | H | |
| 17.013 | Cl | Cl | $CH_3$ | CN | Cl | O | H | H | H | H | |
| 17.014 | Cl | Cl | $CH_3$ | CN | Cl | O | H | $CH_3$ | H | H | |
| 17.015 | Cl | Cl | $CH_3$ | CN | Cl | O | $CH_3$ | $CH_3$ | H | H | |
| 17.016 | Cl | Cl | $CH_3$ | $CSNH_2$ | Cl | O | H | H | H | H | |
| 17.017 | Cl | Cl | $CH_3$ | $CSNH_2$ | Cl | O | H | $CH_3$ | H | H | |
| 17.018 | Cl | Cl | $CH_3$ | CN | Cl | NH | H | H | H | H | |
| 17.019 | Cl | Cl | $CH_3$ | CN | Cl | $N(CH_3)$ | H | $CH_3$ | H | H | |
| 17.020 | Cl | Cl | $CH_3$ | $CSNH_2$ | Cl | NH | $CH_3$ | $CH_3$ | H | H | |
| 17.021 | Cl | Cl | $CH_3$ | CN | Cl | NH | $CH_3$ | $CH_3$ | H | H | |
| 17.022 | H | Cl | $CH_3$ | CN | Cl | O | H | H | H | H | |
| 17.023 | F | Cl | $CH_3$ | $CSNH_2$ | Cl | O | H | H | $CH_3$ | $CH_3$ | |
| 17.024 | F | Cl | $CH_3$ | CN | Cl | O | H | H | $CH_2CH_3$ | $CH_2CH_3$ | |
| 17.025 | F | Cl | $CH_3$ | CN | Cl | O | H | H | $CH_2CH=CH_2$ | $CH_2CH=CH_2$ | |
| 17.026 | F | Cl | $CH_3$ | CN | Cl | O | H | H | $CH_2$-Ph | $CH_2$-Ph | |
| 17.027 | F | Cl | $CH_3$ | CN | Cl | O | H | H | H | $CH_3$ | |
| 17.028 | F | Cl | $CH_3$ | CN | Cl | O | H | H | H | $CH_2CH=CH_2$ | |
| 17.029 | F | Cl | $CH_3$ | $CSNH_2$ | Cl | O | H | H | H | $CH_2$-Ph | |
| 17.030 | F | Cl | $CH_3$ | CN | Cl | O | H | $CH_3$ | $CH_2CH_3$ | $CH_2CH_3$ | |
| 17.031 | F | Cl | $CH_3$ | CN | Cl | O | H | $CH_3$ | H | $CH_2CH=CH_2$ | |
| 17.032 | F | Cl | $CH_3$ | $CSNH_2$ | Cl | O | H | $CH_3$ | $CH_3$ | $CH_3$ | |
| 17.033 | F | Br | $CH_3$ | CN | Cl | O | H | $CH_2CH_2CH_3$ | $CH_2CH_3$ | $CH_2CH_3$ | |
| 17.034 | F | Cl | $CH_3$ | CN | Cl | O | $CH_3$ | $CH_3$ | $CH_3$ | $CH_3$ | |
| 17.035 | F | Cl | $CH_3$ | $CSNH_2$ | Cl | O | $CH_3$ | $CH_3$ | $CH_2CH_3$ | $CH_2CH_3$ | |
| 17.036 | F | Cl | $CH_3$ | CN | Br | O | $CH_3$ | $CH_3$ | H | $CH_2CH=CH_2$ | |
| 17.037 | F | Cl | $CH_3$ | CN | Cl | O | $CH_3$ | $CH_3$ | H | $CH_2$-Ph | |
| 17.038 | Cl | Cl | $CH_3$ | CN | Cl | O | H | H | $CH_2CH_3$ | $CH_2CH_3$ | |

TABLE 17-continued

Compounds of the formula Ir

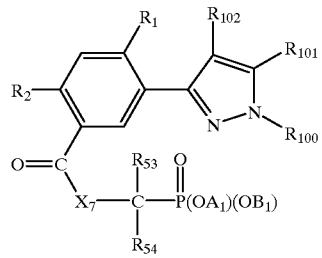

(Ir)

| Compound No. | $R_1$ | $R_2$ | $R_{100}$ | $R_{101}$ | $R_{102}$ | $X_7$ | $R_{53}$ | $R_{54}$ | $A_1$ | $B_1$ | Physical data |
|---|---|---|---|---|---|---|---|---|---|---|---|
| 17.039 | Cl | Cl | $CH_3$ | CN | Cl | O | H | H | H | $CH_2$-Ph | |
| 17.040 | Cl | Cl | $CH_3$ | $CSNH_2$ | Cl | O | H | H | $CH_3$ | $CH_3$ | |
| 17.041 | Cl | Cl | $CH_3$ | CN | Cl | O | H | $CH_2CH_3$ | $CH_2CH_3$ | $CH_2CH_3$ | |
| 17.042 | Cl | Cl | $CH_3$ | $CSNH_2$ | Cl | O | H | $CH_2CH_2CH_3$ | $CH_2CH=CH_2$ | $CH_2CH=CH_2$ | |
| 17.043 | F | Cl | $CH_3$ | CN | Cl | O | cyclopropyl | | $CH_3$ | $CH_3$ | |
| 17.044 | F | Br | $CH_3$ | CN | Cl | O | cyclopentyl | | $CH_2CH=CH_2$ | $CH_2CH=CH_2$ | |
| 17.045 | F | Cl | $CH_3$ | CN | Br | NH | H | H | $CH_2CH_3$ | $CH_2CH_3$ | |
| 17.046 | F | Cl | $CH_3$ | CN | Cl | $N(CH_3)$ | H | H | H | $CH_2$-Ph | |
| 17.047 | F | Cl | $CH_3$ | $CSNH_2$ | Cl | NH | H | $CH_3$ | $CH_3$ | $CH_3$ | |
| 17.048 | F | Cl | $CH_3$ | CN | Br | $N(CH_2CH_3)$ | H | $CH_3$ | $CH_2CH_3$ | $CH_2CH_3$ | |
| 17.049 | F | Cl | $CH_3$ | $CSNH_2$ | Br | $N(CH_3)$ | H | $CH_3$ | $CH_2$-Ph | $CH_2$-Ph | |
| 17.050 | F | Cl | $CH_3$ | CN | Cl | NH | $CH_3$ | $CH_3$ | $CH_2CH=CH_2$ | $CH_2CH=CH_2$ | |
| 17.051 | Cl | Cl | $CH_3$ | CN | Cl | NH | H | H | $CH_2CH_3$ | $CH_2CH_3$ | |
| 17.052 | Cl | Cl | $CH_3$ | $CSNH_2$ | Cl | NH | H | H | H | $CH_2CH=CH_2$ | |
| 17.053 | Cl | Cl | $CH_3$ | $CSNH_2$ | Cl | $N(CH_3)$ | H | H | $CH_3$ | $CH_3$ | |
| 17.054 | F | Cl | $CH_3$ | CN | Cl | O | H | $CCl_3$ | $CH_2CH_3$ | $CH_2CH_3$ | |

TABLE 18

Compounds of the formula Is

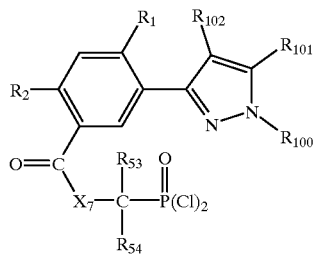

(Is)

| Compound No. | R₁ | R₂ | R₁₀₀ | R₁₀₁ | R₁₀₂ | X₇ | R₅₃ | R₅₄ | Physical data |
|---|---|---|---|---|---|---|---|---|---|
| 18.01 | H | Cl | CH₃ | CN | Cl | O | H | H | |
| 18.02 | F | Cl | CH₃ | CN | Cl | O | H | H | |
| 18.03 | F | Cl | CH₃ | CN | Br | O | H | H | |
| 18.04 | F | Br | CH₃ | CN | Cl | O | H | H | |
| 18.05 | Cl | Cl | CH₃ | CN | Cl | O | H | H | |
| 18.06 | F | Cl | CH₃ | CN | Cl | O | H | CH₃ | |
| 18.07 | F | Cl | CH₃ | CN | Br | O | H | CH₃ | |
| 18.08 | F | Br | CH₃ | CN | Cl | O | H | CH₃ | |
| 18.09 | Cl | Cl | CH₃ | CN | Cl | O | H | CH₃ | |
| 18.10 | F | Cl | CH₃ | CN | Cl | O | CH₃ | CH₃ | |
| 18.11 | F | Cl | CH₃ | CN | Br | O | CH₃ | CH₃ | |
| 18.12 | F | Br | CH₃ | CN | Cl | O | CH₃ | CH₃ | |
| 18.13 | Cl | Cl | CH₃ | CN | Cl | O | CH₃ | CH₃ | |
| 18.14 | F | Cl | CH₃ | CN | Cl | N(CH₃) | H | H | |
| 18.15 | Cl | Cl | CH₃ | CN | Cl | N(CH₃) | H | H | |
| 18.16 | F | Cl | CH₃ | CN | Br | N(CH₃) | H | H | |
| 18.17 | F | Cl | CH₃ | CN | Cl | N(CH₃) | H | CH₃ | |
| 18.18 | Cl | Cl | CH₃ | CN | Cl | N(CH₃) | H | CH₃ | |
| 18.19 | F | Cl | CH₃ | CN | Br | N(CH₃) | H | CH₃ | |
| 18.20 | F | Cl | CH₃ | CN | Cl | N(CH₃) | CH₃ | CH₃ | |

TABLE 19

Compounds of the formula It

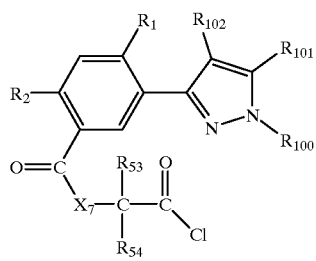

(It)

| Compound No. | R₁ | R₂ | R₁₀₀ | R₁₀₁ | R₁₀₂ | X₇ | R₅₃ | R₅₄ | Physical data |
|---|---|---|---|---|---|---|---|---|---|
| 19.01 | H | Cl | CH₃ | CN | Cl | O | H | H | |
| 19.02 | H | Cl | CH₃ | CN | Cl | O | H | CH₃ | |
| 19.03 | H | Cl | CH₃ | CN | Cl | O | CH₃ | CH₃ | |
| 19.04 | H | Cl | CH₃ | CN | Cl | NH | H | H | |
| 19.05 | H | Cl | CH₃ | CN | Cl | NH | H | CH₃ | |
| 19.06 | F | Cl | CH₃ | CN | Cl | O | H | H | |
| 19.07 | F | Cl | CH₃ | CN | Br | O | H | H | |
| 19.08 | F | Cl | CH₃ | CN | Cl | O | H | CH₃ | |
| 19.09 | F | Cl | CH₃ | CN | Br | O | H | CH₃ | |
| 19.10 | F | Cl | CH₃ | CN | Cl | O | CH₃ | CH₃ | |
| 19.11 | F | Cl | CH₃ | CN | Br | O | CH₃ | CH₃ | |
| 19.12 | F | Br | CH₃ | CN | Cl | O | H | H | |
| 19.13 | F | Br | CH₃ | CN | Cl | O | H | CH₃ | |
| 19.14 | F | Br | CH₃ | CN | Cl | O | CH₃ | CH₃ | |
| 19.15 | Cl | Cl | CH₃ | CN | Cl | O | H | H | |
| 19.16 | Cl | Cl | CH₃ | CN | Cl | O | H | CH₃ | |
| 19.17 | Cl | Cl | CH₃ | CN | Cl | O | CH₃ | CH₃ | |
| 19.18 | F | Cl | CH₃ | CN | Cl | NH | H | H | |
| 19.19 | F | Cl | CH₃ | CN | Cl | N(CH₃) | H | H | |
| 19.20 | F | Cl | CH₃ | CN | Br | NH | H | H | |
| 19.21 | F | Br | CH₃ | CN | Cl | NH | H | H | |
| 19.22 | F | Cl | CH₃ | CN | Cl | NH | H | CH₃ | |
| 19.23 | F | Cl | CH₃ | CN | Cl | N(CH₃) | H | CH₃ | |
| 19.24 | F | Cl | CH₃ | CN | Br | NH | H | CH₃ | |
| 19.25 | F | Br | CH₃ | CN | Cl | NH | H | CH₃ | |
| 19.26 | F | Cl | CH₃ | CN | Cl | NH | CH₃ | CH₃ | |
| 19.27 | F | Cl | CH₃ | CN | Cl | N(CH₃) | CH₃ | CH₃ | |
| 19.28 | F | Cl | CH₃ | CN | Br | NH | CH₃ | CH₃ | |
| 19.29 | F | Br | CH₃ | CN | Cl | NH | CH₃ | CH₃ | |
| 19.30 | Cl | Cl | CH₃ | CN | Cl | NH | CH₃ | CH₃ | |
| 19.31 | Cl | Cl | CH₃ | CN | Cl | N(CH₃) | CH₃ | CH₃ | |
| 19.32 | F | Cl | CH₃ | CN | Cl | S | H | H | |
| 19.33 | F | Cl | CH₃ | CN | Br | S | H | H | |
| 19.34 | F | Br | CH₃ | CN | Cl | S | H | H | |
| 19.35 | Cl | Cl | CH₃ | CN | Cl | O | ▽ | | |
| 19.36 | F | Br | CH₃ | CN | Cl | O | ▽ | | |
| 19.37 | F | Cl | CH₃ | CN | Br | O | ▽ | | |

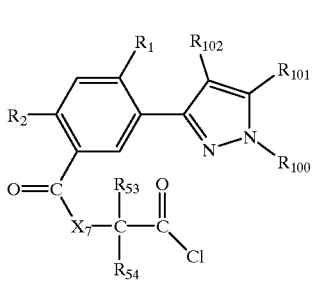

TABLE 20

Compounds of the formula Iu

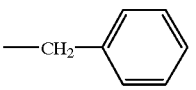

| Compound No. | $R_{22}$ | $R_{19}$ | $R_{100}$ | $R_{101}$ | $R_{102}$ | Physical data |
|---|---|---|---|---|---|---|
| 20.001 | H | H | H | CN | Cl | m.p. >280° C. |
| 20.002 | H | CH$_3$ | CH$_3$ | CN | Cl | |
| 20.003 | H | CH$_2$—CH$_3$ | CH$_3$ | CN | Cl | |
| 20.004 | H | —CH(CH$_3$)$_2$ | CH$_3$ | CN | Cl | |
| 20.005 | H | CH$_2$—C≡CH | CH$_3$ | CN | Cl | |
| 20.006 | H | —CH(CH$_3$)C≡CH | CH$_3$ | CN | Cl | |
| 20.007 | H | CH$_2$—CH=CH$_2$ | CH$_3$ | CN | Cl | |
| 20.008 | H | CH$_2$COOCH$_3$ | CH$_3$ | CN | Cl | |
| 20.009 | H | CH(CH$_3$)COOCH$_3$ | CH$_3$ | CN | Cl | |
| 20.010 | H | CH$_2$—COOC$_2$H$_5$ | CH$_3$ | CN | Cl | |
| 20.011 | H | CH(CH$_3$)COOC$_2$H$_5$ | CH$_3$ | CN | Cl | |
| 20.012 | H | —CH$_2$—CH=CH—Cl | CH$_3$ | CN | Cl | |
| 20.013 | H | —CH(CH$_3$)—CH$_2$—CH$_3$ | CH$_3$ | CN | Cl | |
| 20.014 | H | —CH$_2$—CN | CH$_3$ | CN | Cl | |
| 20.015 | H | —CH(CH$_3$)CN | CH$_3$ | CN | Cl | |
| 20.016 | Cl | —CH$_3$ | CH$_3$ | CN | Cl | |
| 20.017 | Cl | —CH(CH$_3$)$_2$ | CH$_3$ | CN | Cl | |
| 20.018 | Cl | —CH$_2$—COOCH$_3$ | CH$_3$ | CN | Cl | |
| 20.019 | Cl | —CH$_2$—COOC$_2$H$_5$ | CH$_3$ | CN | Cl | |
| 20.020 | Cl | —CH(CH$_3$)COOCH$_3$ | CH$_3$ | CN | Cl | |
| 20.021 | Cl | —CH$_2$—C≡CH | CH$_3$ | CN | Cl | |
| 20.022 | Cl | —CH(CH$_3$)—C≡CH | CH$_3$ | CN | Cl | |
| 20.023 | H | —CH$_2$—C≡CH | CH$_3$ | CN | Br | |
| 20.024 | H | —CH(CH$_3$)C≡CH | CH$_3$ | CN | Br | |
| 20.025 | F | CH$_3$ | CH$_3$ | CN | Cl | |
| 20.026 | F | C$_2$H$_5$ | CH$_3$ | CN | Cl | |
| 20.027 | F | CH$_2$—CH$_2$—CH$_3$ | CH$_3$ | CN | Cl | |
| 20.028 | F | CH(CH$_3$)$_2$ | CH$_3$ | CN | Cl | |
| 20.029 | F | —CH(CH$_3$)C$_2$H$_5$ | CH$_3$ | CN | Cl | |
| 20.030 | F | —CH$_2$—COOCH$_3$ | CH$_3$ | CN | Cl | |
| 20.031 | F | —CH$_2$—COOC$_2$H$_5$ | CH$_3$ | CN | Cl | |
| 20.032 | F | —CH(CH$_3$)COOCH$_3$ | CH$_3$ | CN | Cl | |
| 20.033 | F | —CH(CH$_3$)COOC$_2$H$_5$ | CH$_3$ | CN | Cl | |
| 20.034 | F | —CH$_2$—CH=CH$_2$ | CH$_3$ | CN | Cl | |
| 20.035 | F | —CH$_2$—C≡CH | CH$_3$ | CN | Cl | |
| 20.036 | F | —CH(CH$_3$)C≡CH | CH$_3$ | CN | Cl | |
| 20.037 | F | —CH$_2$CN | CH$_3$ | CN | Cl | |
| 20.038 | F | —CH(CH$_3$)CN | CH$_3$ | CN | Cl | |
| 20.039 | F | —CH$_2$—CH=CHCl | CH$_3$ | CN | Cl | |
| 20.040 | F | —CH$_2$—O—CH$_3$ | CH$_3$ | CN | Cl | |
| 20.041 | F | —CH$_2$—O—C$_2$H$_5$ | CH$_3$ | CN | Cl | |
| 20.042 | F | —CH$_2$—C$_6$H$_5$ | CH$_3$ | CN | Cl | |
| 20.043 | F | —CH$_2$—CH=CH—CH$_3$ | CH$_3$ | CN | Cl | |
| 20.044 | F | —H | CH$_3$ | CN | Br | |
| 20.045 | F | —CH(CH$_3$)$_2$ | CH$_3$ | CN | Br | |
| 20.046 | F | —CH$_2$—C≡CH | CH$_3$ | CN | Br | |
| 20.047 | F | —CH(CH$_3$)C≡CH | CH$_3$ | CN | Br | |
| 20.048 | F | —H | CH$_3$ | CSNH$_2$ | Cl | |
| 20.049 | F | —CH$_3$ | CH$_3$ | CSNH$_2$ | Cl | |
| 20.050 | F | —C$_2$H$_5$ | CH$_3$ | CSNH$_2$ | Cl | |
| 20.051 | F | —CH(CH$_3$)$_2$ | CH$_3$ | CSNH$_2$ | Cl | |
| 20.052 | F | —CH$_2$—COOCH$_3$ | CH$_3$ | CSNH$_2$ | Cl | |
| 20.053 | F | —CH(CH$_3$)COOCH$_3$ | CH$_3$ | CSNH$_2$ | Cl | |
| 20.054 | F | —CH$_2$—CH=CH$_2$ | CH$_3$ | CSNH$_2$ | Cl | |
| 20.055 | F | —CH$_2$—C≡CH | CH$_3$ | CSNH$_2$ | Cl | |

TABLE 20-continued

Compounds of the formula Iu

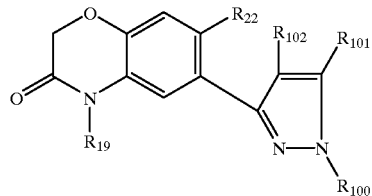

(Iu)

| Compound No. | $R_{22}$ | $R_{19}$ | $R_{100}$ | $R_{101}$ | $R_{102}$ | Physical data |
|---|---|---|---|---|---|---|
| 20.056 | F | —CH(CH$_3$)C≡CH | CH$_3$ | CSNH$_2$ | Cl | |
| 20.057 | Cl | CH$_2$—C≡CH | CH$_3$ | CSNH$_2$ | Cl | |
| 20.058 | F | CH$_2$—C≡CH | CH$_3$ | CSNH$_2$ | Br | |
| 20.059 | F | —CH(CH$_3$)C≡CH | CH$_3$ | CSNH$_2$ | Br | |
| 20.060 | F | —CH(CH$_3$)$_2$ | CH$_3$ | CSNH$_2$ | Br | |
| 20.061 | H | H | CH$_3$ | CSNH$_2$ | Cl | |
| 20.062 | H | H | CH$_3$ | CSNH$_2$ | Br | |
| 20.063 | F | H | CH$_3$ | CSNH$_2$ | Br | |
| 20.064 | H | CH$_3$ | CH$_3$ | CSNH$_2$ | Cl | |
| 20.065 | H | CH$_3$ | CH$_3$ | CSNH$_2$ | Cl | |
| 20.066 | H | CH$_3$ | CH$_3$ | CSNH$_2$ | Br | |
| 20.067 | F | CH$_3$ | CH$_3$ | CSNH$_2$ | Br | |
| 20.068 | H | CH(CH$_3$)$_2$ | CH$_3$ | CSNH$_2$ | Cl | |
| 20.069 | H | CH(CH$_3$)$_2$ | CH$_3$ | CSNH$_2$ | Br | |
| 20.070 | F | CH(CH$_3$)$_2$ | CH$_3$ | CSNH$_2$ | Br | |
| 20.071 | H | CH$_2$—CH=CH$_2$ | CH$_3$ | CSNH$_2$ | Cl | |
| 20.072 | F | CH$_2$—CH=CH$_2$ | CH$_3$ | CSNH$_2$ | Cl | |
| 20.073 | H | CH$_2$—CH=CH$_2$ | CH$_3$ | CSNH$_2$ | Br | |
| 20.074 | F | CH$_2$—CH=CH$_2$ | CH$_3$ | CSNH$_2$ | Br | |
| 20.075 | H | CH$_2$—C≡CH | CH$_3$ | CSNH$_2$ | Cl | |
| 20.076 | F | CH$_2$—C≡CH | CH$_3$ | CSNH$_2$ | Cl | |
| 20.077 | H | CH$_2$—C≡CH | CH$_3$ | CSNH$_2$ | Br | |
| 20.078 | F | CH$_2$—C≡CH | CH$_3$ | CSNH$_2$ | Br | |
| 20.079 | H | CH$_2$—COOC$_2$H$_5$ | CH$_3$ | CSNH$_2$ | Cl | |
| 20.080 | F | CH$_2$—COOC$_2$H$_5$ | CH$_3$ | CSNH$_2$ | Cl | |
| 20.081 | H | CH$_2$—COOC$_2$H$_5$ | CH$_3$ | CSNH$_2$ | Br | |
| 20.082 | F | CH$_2$—COOC$_2$H$_5$ | CH$_3$ | CSNH$_2$ | Br | |
| 20.083 | H | CH(CH$_3$)COOCH$_3$ | CH$_3$ | CSNH$_2$ | Cl | |
| 20.084 | F | CH(CH$_3$)COOCH$_3$ | CH$_3$ | CSNH$_2$ | Cl | |
| 20.085 | H | CH(CH$_3$)COOCH$_3$ | CH$_3$ | CSNH$_2$ | Br | |
| 20.086 | F | CH(CH$_3$)COOCH$_3$ | CH$_3$ | CSNH$_2$ | Br | |

TABLE 21

Compounds of the formula Iv

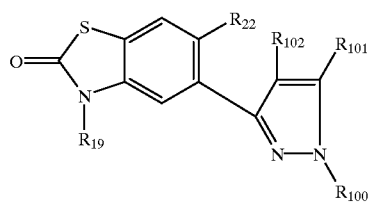

(Iv)

| Compound No. | $R_{22}$ | $R_{19}$ | $R_{100}$ | $R_{101}$ | $R_{102}$ | Physical data |
|---|---|---|---|---|---|---|
| 21.001 | H | H | H | CN | Cl | m.p. >280° C. |
| 21.002 | H | CH$_3$ | CH$_3$ | CN | Cl | |
| 21.003 | H | C$_2$H$_5$ | CH$_3$ | CN | Cl | |
| 21.004 | H | CH(CH$_3$)$_2$ | CH$_3$ | CN | Cl | m.p. 183° C. |
| 21.005 | H | —CH(CH$_3$)C$_2$H$_5$ | CH$_3$ | CN | Cl | |
| 21.006 | H | —CH$_2$—COOCH$_3$ | CH$_3$ | CN | Cl | |
| 21.007 | H | —CH$_2$—COOC$_2$H$_5$ | CH$_3$ | CN | Cl | |

TABLE 21-continued

Compounds of the formula Iv

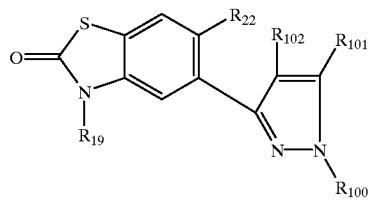

(Iv)

| Compound No. | $R_{22}$ | $R_{19}$ | $R_{100}$ | $R_{101}$ | $R_{102}$ | Physical data |
|---|---|---|---|---|---|---|
| 21.008 | H | —CH(CH$_3$)COOCH$_3$ | CH$_3$ | CN | Cl | |
| 21.009 | H | —CH(CH$_3$)—COOC$_2$H$_5$ | CH$_3$ | CN | Cl | |
| 21.010 | H | —CH$_2$—C≡CH | CH$_3$ | CN | Cl | |
| 21.011 | H | —CH(CH$_3$)C≡CH | CH$_3$ | CN | Cl | |
| 21.012 | H | —CH(CH$_3$)CN | CH$_3$ | CN | Cl | |
| 21.013 | Cl | —CH$_3$ | CH$_3$ | CN | Cl | |
| 21.014 | Cl | —CH(CH$_3$)$_2$ | CH$_3$ | CN | Cl | |
| 21.015 | Cl | —CH$_2$—C≡CH | CH$_3$ | CN | Cl | |
| 21.016 | Cl | —CH(CH$_3$)COOC$_2$H$_5$ | CH$_3$ | CN | Cl | |
| 21.017 | F | H | CH$_3$ | CN | Cl | |
| 21.018 | F | CH$_3$ | CH$_3$ | CN | Cl | |
| 21.019 | F | C$_2$H$_5$ | CH$_3$ | CN | Cl | |
| 21.020 | F | CH$_2$—CH$_2$—CH$_3$ | CH$_3$ | CN | Cl | |
| 21.021 | F | CH(CH$_3$)$_2$ | CH$_3$ | CN | Cl | m.p. 167–169° C. |
| 21.022 | F | CH(CH$_3$)C$_2$H$_5$ | CH$_3$ | CN | Cl | |
| 21.023 | F | —CH$_2$—CH(CH$_3$)$_2$ | CH$_3$ | CN | Cl | |
| 21.024 | F | —CH$_2$—CH=CH$_2$ | CH$_3$ | CN | Cl | |
| 21.025 | F | —CH$_2$—C≡CH | CH$_3$ | CN | Cl | |
| 21.026 | F | —CH(CH$_3$)C≡CH | CH$_3$ | CN | Cl | |
| 21.027 | F | —CH$_2$—COOCH$_3$ | CH$_3$ | CN | Cl | |
| 21.028 | F | —CH(CH$_3$)COOCH$_3$ | CH$_3$ | CN | Cl | |
| 21.029 | F | —CH(CH$_3$)COOC$_2$H$_5$ | CH$_3$ | CN | Cl | |
| 21.030 | F | —CH$_2$—CN | CH$_3$ | CN | Cl | |
| 21.031 | F | —CH(CH$_3$)CN | CH$_3$ | CN | Cl | |
| 21.032 | F | —CH$_2$—O—CH$_3$ | CH$_3$ | CN | Cl | |
| 21.033 | F | —CH$_2$—O—C$_2$H$_5$ | CH$_3$ | CN | Cl | |
| 21.034 | H | CH$_3$ | CH$_3$ | CN | Br | |
| 21.035 | H | CH(CH$_3$)$_2$ | CH$_3$ | CN | Br | |
| 21.036 | H | CH(CH$_3$)COOC$_2$H$_5$ | CH$_3$ | CN | Br | |
| 21.037 | H | CH(CH$_3$)$_2$ | CH$_3$ | CSNH$_2$ | Cl | |
| 21.038 | H | —CH(CH$_3$)COOC$_2$H$_5$ | CH$_3$ | CSNH$_2$ | Cl | |
| 21.039 | Cl | —CH(CH$_3$)$_2$ | CH$_3$ | CSNH$_2$ | Cl | |
| 21.040 | F | CH$_3$ | CH$_3$ | CSNH$_2$ | Cl | |
| 21.041 | F | CH(CH$_3$)$_2$ | CH$_3$ | CSNH$_2$ | Cl | |
| 21.042 | F | CH$_2$COOC$_2$H$_5$ | CH$_3$ | CSNH$_2$ | Cl | |
| 21.043 | F | CH(CH$_3$)COOC$_2$H$_5$ | CH$_3$ | CSNH$_2$ | Cl | |
| 21.044 | F | CH(CH$_3$)$_2$ | CH$_3$ | CSNH$_2$ | Br | |
| 21.045 | F | CH(CH$_3$)COOC$_2$H$_5$ | CH$_3$ | CSNH$_2$ | Br | |
| 21.046 | H | H | CH$_3$ | CSNH$_2$ | Cl | |
| 21.047 | F | H | CH$_3$ | CSNH$_2$ | Cl | |
| 21.048 | Cl | H | CH$_3$ | CSNH$_2$ | Cl | |
| 21.049 | H | H | CH$_3$ | CSNH$_2$ | Br | |
| 21.050 | F | H | CH$_3$ | CSNH$_2$ | Br | |
| 21.051 | Cl | H | CH$_3$ | CSNH$_2$ | Br | |
| 21.052 | H | —CH(CH$_3$)$_2$ | CH$_3$ | CSNH$_2$ | Cl | |
| 21.053 | F | —CH(CH$_3$)$_2$ | CH$_3$ | CSNH$_2$ | Cl | |
| 21.054 | Cl | CH(CH$_3$)$_2$ | CH$_3$ | CSNH$_2$ | Cl | |
| 21.055 | H | CH(CH$_3$)$_2$ | CH$_3$ | CSNH$_2$ | Br | |
| 21.056 | Cl | CH(CH$_3$)$_2$ | CH$_3$ | CSNH$_2$ | Br | |
| 21.057 | H | CH$_2$—C≡CH | CH$_3$ | CSNH$_2$ | Cl | |
| 21.058 | F | CH$_2$—C≡CH | CH$_3$ | CSNH$_2$ | Cl | |
| 21.059 | Cl | CH$_2$—C≡CH | CH$_3$ | CSNH$_2$ | Cl | |
| 21.060 | H | CH$_2$—C≡CH | CH$_3$ | CSNH$_2$ | Br | |
| 21.061 | F | CH$_2$—C≡CH | CH$_3$ | CSNH$_2$ | Br | |
| 21.062 | Cl | CH$_2$—C≡CH | CH$_3$ | CSNH$_2$ | Br | |
| 21.063 | H | CH$_2$—COOC$_2$H$_5$ | CH$_3$ | CSNH$_2$ | Cl | |
| 21.064 | F | CH$_2$—COOC$_2$H$_5$ | CH$_3$ | CSNH$_2$ | Cl | |
| 21.065 | Cl | CH$_2$—COOC$_2$H$_5$ | CH$_3$ | CSNH$_2$ | Cl | |
| 21.066 | H | CH$_2$—COOC$_2$H$_5$ | CH$_3$ | CSNH$_2$ | Br | |
| 21.067 | F | CH$_2$—COOC$_2$H$_5$ | CH$_3$ | CSNH$_2$ | Br | |
| 21.068 | Cl | CH$_2$—COOC$_2$H$_5$ | CH$_3$ | CSNH$_2$ | Br | |

TABLE 21-continued

Compounds of the formula Iv

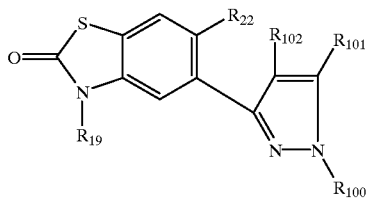

(Iv)

| Compound No. | $R_{22}$ | $R_{19}$ | $R_{100}$ | $R_{101}$ | $R_{102}$ | Physical data |
|---|---|---|---|---|---|---|
| 21.069 | F | $CH_2$—CH=$CH_2$ | $CH_3$ | $CSNH_2$ | Cl | |
| 21.070 | F | $CH_2$—CH=$CH_2$ | $CH_3$ | $CSNH_2$ | Br | |
| 21.071 | F | $CH(CH_3)C\equiv CH$ | $CH_3$ | $CSNH_2$ | Cl | |
| 21.072 | F | $CH(CH_3)C\equiv CH$ | $CH_3$ | $CSNH_2$ | Br | |
| 21.073 | F | —$CH_2COOCH_3$ | $CH_3$ | $CSNH_2$ | Cl | |
| 21.074 | F | $CH_2$—$COOCH_3$ | $CH_3$ | $CSNH_2$ | Br | |
| 21.075 | F | $CH(CH_3)COOCH_3$ | $CH_3$ | $CSNH_2$ | Cl | |
| 21.076 | F | $CH(CH_3)COOCH_3$ | $CH_3$ | $CSNH_2$ | Br | |
| 21.077 | F | $CH_2$—CH=$CH_2$ | $CH_3$ | $CSNH_2$ | Cl | |
| 21.078 | H | $CH_2$—CH=$CH_2$ | $CH_3$ | $CSNH_2$ | Br | |
| 21.079 | H | $CH(CH_3)C\equiv CH$ | $CH_3$ | $CSNH_2$ | Cl | |
| 21.080 | H | $CH(CH_3)C\equiv CH$ | $CH_3$ | $CSNH_2$ | Br | |
| 21.081 | H | $CH_2$—$COOCH_3$ | $CH_3$ | $CSNH_2$ | Cl | |
| 21.082 | H | $CH_2$—$COOCH_3$ | $CH_3$ | $CSNH_2$ | Br | |
| 21.083 | H | $CH(CH_3)COOCH_3$ | $CH_3$ | $CSNH_2$ | Cl | |
| 21.084 | H | $CH(CH_3)COOCH_3$ | $CH_3$ | $CSNH_2$ | Br | |
| 21.085 | H | $CH_2COOCH_3$ | $CH_3$ | $CSNH_2$ | Cl | |
| 21.086 | F | $CH_2COOCH_3$ | $CH_3$ | $CSNH_2$ | Cl | |

TABLE 22

Compounds of the formula Iw

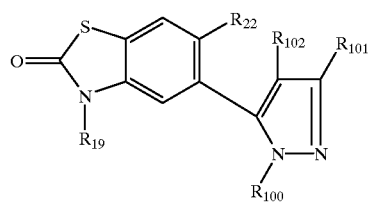

(Iw)

| Compound No. | $R_{22}$ | $R_{19}$ | $R_{100}$ | $R_{101}$ | $R_{102}$ | Physical data |
|---|---|---|---|---|---|---|
| 22.001 | H | H | $CH_3$ | CN | Cl | |
| 22.002 | F | H | $CH_3$ | CN | Cl | |
| 22.003 | Cl | H | $CH_3$ | CN | Cl | |
| 22.004 | F | $CH_3$ | $CH_3$ | CN | Cl | |
| 22.005 | F | $CH(CH_3)_2$ | $CH_3$ | CN | Cl | |
| 22.006 | F | $CH_2$—CH=$CH_2$ | $CH_3$ | CN | Cl | |
| 22.007 | F | $CH_2$—$C\equiv CH$ | $CH_3$ | CN | Cl | |
| 22.008 | F | $CH_2$—$COOCH_3$ | $CH_3$ | CN | Cl | |
| 22.009 | F | $CH_2$—$COOC_2H_5$ | $CH_3$ | CN | Cl | |
| 22.010 | F | $CH(CH_3)COOC_2H_5$ | $CH_3$ | CN | | |
| 22.011 | F | —$CH(CH_3)\equiv CH$ | $CH_3$ | CN | Cl | |
| 22.012 | F | —$CH_3$ | $CH_3$ | CN | Br | |
| 22.013 | F | —$CH(CH_3)_2$ | $CH_3$ | CN | Br | |

TABLE 22-continued

Compounds of the formula Iw

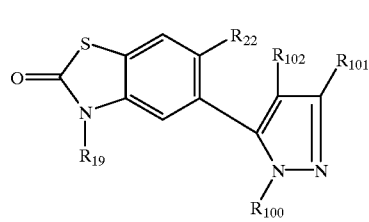

(Iw)

| Compound No. | $R_{22}$ | $R_{19}$ | $R_{100}$ | $R_{101}$ | $R_{102}$ | Physical data |
|---|---|---|---|---|---|---|
| 22.014 | F | —$CH_2$—CH=$CH_2$ | $CH_3$ | CN | Br | |
| 22.015 | F | —$CH_2$—$C\equiv CH$ | $CH_3$ | CN | Br | |
| 22.016 | F | $CH_2$—$COOCH_3$ | $CH_3$ | CN | Br | |
| 22.017 | F | —$CH_2$—$COOC_2H_5$ | $CH_3$ | CN | Br | |
| 22.018 | F | —$CH(CH_3)COOC_2H_5$ | $CH_3$ | CN | Br | |
| 22.019 | F | —$CH(CH_3)C\equiv CH$ | $CH_3$ | CN | Br | |
| 22.020 | H | —$CH(CH_3)_2$ | $CH_3$ | CN | Cl | resin |

TABLE 23

Compounds of the formula Ix

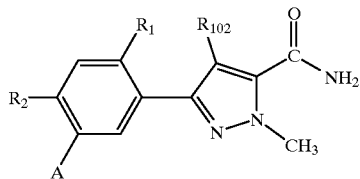

(Ix)

| Compound No. | $R_{102}$ | $R_1$ | $R_2$ | A | Physical data |
|---|---|---|---|---|---|
| 23.001 | Cl | F | Cl | H | |
| 23.002 | Cl | F | Cl | OH | solid |
| 23.003 | Cl | F | Cl | $OCH_3$ | 173–175° C. |
| 23.004 | Cl | F | Cl | $OCH_2C_6H_5$ | |
| 23.005 | Cl | F | Cl | $OCH_2CH=CH_2$ | |
| 23.006 | Cl | F | Cl | $OCH(CH_3)_2$ | solid |
| 23.007 | Cl | F | Cl | $COOCH_3$ | |
| 23.008 | Cl | F | Cl | $COOCH(CH_3)_2$ | 162–165° C. |
| 23.009 | Cl | F | Cl | $OCH_2OCH_3$ | |
| 23.010 | Cl | F | Cl | $COOCH_2CH=CH_2$ | |
| 23.011 | Cl | F | Cl | $COOCH_2C_6H_5$ | |
| 23.012 | Cl | F | Cl | $NO_2$ | |
| 23.013 | Cl | F | Cl | $NHSO_2CH_3$ | |
| 23.014 | Cl | F | Cl | $N(SO_2CH_3)_2$ | |
| 23.015 | Cl | F | Cl | $NH_2$ | |
| 23.016 | Cl | F | Cl | I | 226–228° C. |
| 23.017 | Cl | F | Cl | Br | |
| 23.018 | Cl | F | Cl | Cl | |
| 23.019 | Cl | F | Cl | F | |
| 23.020 | Cl | F | Cl | $SO_2Cl$ | |
| 23.021 | Cl | F | Cl | SH | |
| 23.022 | Cl | F | Cl | $SCH_3$ | |
| 23.023 | Cl | F | Cl | $SCH_2CH=CH_2$ | |
| 23.024 | Cl | F | Cl | $SCH(CH_3)_2$ | |
| 23.025 | Cl | F | Cl | $CH_3$ | |
| 23.026 | Cl | F | Cl | CHO | |
| 23.027 | Cl | F | Cl | $CH_2Cl$ | |
| 23.028 | Cl | F | Cl | $CH_2OH$ | |
| 23.029 | Cl | F | Cl | $OCH_2COOCH_3$ | |
| 23.030 | Cl | F | Cl | $OCH_2COOCH_2CH_3$ | |
| 23.031 | Cl | F | Cl | $SCH_2COOCH_3$ | |
| 23.032 | Cl | F | Cl | $SCH_2COOCH_2CH_3$ | |
| 23.033 | Cl | H | Cl | H | |
| 23.034 | Cl | H | Cl | OH | |
| 23.035 | Cl | H | Cl | $NO_2$ | |
| 23.036 | Cl | H | Cl | $NH_2$ | |
| 23.037 | Cl | H | Cl | I | |
| 23.038 | Cl | H | Cl | Br | |
| 23.039 | Cl | H | Cl | Cl | |
| 23.040 | Cl | H | Cl | F | |
| 23.041 | Cl | H | Cl | $OCH_3$ | |
| 23.042 | Cl | H | Cl | COOH | |
| 23.043 | Cl | H | Cl | COCl | |
| 23.044 | Cl | H | Cl | $COOCH_3$ | |
| 23.045 | Cl | H | Cl | $OCH_2CH=CH_2$ | |
| 23.046 | Cl | H | Cl | $COOCH_2CH=CH_2$ | |
| 23.047 | Cl | H | Cl | $OCH_2CH=CH_2$ | |
| 23.048 | Cl | H | Cl | $OCH_2OCH_3$ | |
| 23.049 | Cl | H | Cl | $OCH_2C_6H_5$ | |
| 23.050 | Cl | H | Cl | $SO_2Cl$ | |
| 23.051 | Cl | H | Cl | SH | |
| 23.052 | Cl | H | Cl | $SCH_3$ | |
| 23.053 | Cl | H | Cl | $SCH_2CH=CH_2$ | |
| 23.054 | Cl | H | Cl | $SCH_2C_6H_5$ | |
| 23.055 | Cl | H | Cl | $CH_3$ | |
| 23.056 | Cl | H | Cl | $CH_2Cl$ | |
| 23.057 | Cl | H | Cl | $CH_2OH$ | |
| 23.058 | Cl | H | Cl | CHO | |
| 23.059 | Cl | Cl | Cl | OH | |
| 23.060 | Br | F | Cl | $COOCH_2CH_2CN$ | solid |
| 23.061 | Cl | Cl | Cl | $NO_2$ | |
| 23.062 | Cl | Cl | Cl | $NH_2$ | |
| 23.063 | Br | F | Cl | I | 205–207° C. |

TABLE 23-continued

Compounds of the formula Ix

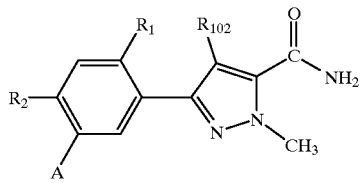

(Ix)

| Compound No. | $R_{102}$ | $R_1$ | $R_2$ | A | Physical data |
|---|---|---|---|---|---|
| 23.064 | Br | F | Cl | Br | |
| 23.065 | Br | F | Cl | Cl | |
| 23.066 | Br | F | Cl | H | 167–168° C. |
| 23.067 | Br | F | Cl | OH | solid |
| 23.068 | Br | F | Cl | $OCH_3$ | 191–193° C. |
| 23.069 | Br | F | Cl | SH | |
| 23.070 | Br | F | Cl | $SCH_3$ | |
| 23.071 | Br | F | Cl | $SO_2Cl$ | |
| 23.072 | Br | F | Cl | $OCH_2CH=CH_2$ | |
| 23.073 | Br | F | Cl | $OCH_2C_6H_5$ | |
| 23.074 | Br | F | Cl | $SCH_2CH=CH_2$ | |
| 23.075 | Br | F | Cl | $OCH(CH_3)_2$ | |
| 23.076 | Br | F | Cl | $SCH(CH_3)_2$ | |
| 23.077 | Br | F | Cl | $SCH_2C_6H_5$ | |
| 23.078 | Br | F | Cl | $COOCH_3$ | 158–160° C. |
| 23.079 | Br | F | Cl | COOH | |
| 23.080 | Br | F | Cl | COCl | |
| 23.081 | Br | F | Cl | $COOCH(CH_3)_2$ | |
| 23.082 | Br | F | Cl | $COOCH_2CH=CH_2$ | |
| 23.083 | Br | F | Cl | $COOCH_2C_6H_5$ | solid |
| 23.084 | Br | F | Cl | $CH_3$ | |
| 23.085 | Br | F | Cl | $CH_2OH$ | |
| 23.086 | Br | F | Cl | $CH_2Cl$ | |
| 23.087 | Br | F | Cl | CHO | |
| 23.088 | Cl | F | $CH_3$ | H | |
| 23.089 | Cl | F | $CH_3$ | $NO_2$ | |
| 23.090 | Cl | F | $CH_3$ | $NH_2$ | |
| 23.091 | Cl | F | $CH_3$ | I | |
| 23.092 | Cl | F | $CH_3$ | Br | |
| 23.093 | Cl | F | $CH_3$ | OH | |
| 23.094 | Cl | F | $CH_3$ | $OCH_3$ | |
| 23.095 | Cl | F | $CH_3$ | $SO_2Cl$ | |
| 23.096 | Cl | F | $CH_3$ | SH | |
| 23.097 | Cl | F | $CH_3$ | $SCH_3$ | |
| 23.098 | Cl | F | $CH_3$ | COOH | |
| 23.099 | Cl | F | $CH_3$ | COCl | |
| 23.100 | Cl | F | $CH_3$ | $COOCH_3$ | |
| 23.101 | Cl | F | $CH_3$ | $CH_3$ | |
| 23.102 | Cl | F | $CH_3$ | CHO | |
| 23.103 | Cl | F | $CH_3$ | $CH_2Cl$ | |
| 23.104 | Cl | F | $CH_3$ | $CH_2OH$ | |
| 23.105 | Cl | F | $NO_2$ | H | |
| 23.106 | Cl | F | $NO_2$ | F | |
| 23.107 | Cl | F | $NO_2$ | Cl | |
| 23.108 | Cl | F | $NO_2$ | Br | |
| 23.109 | Cl | F | $NO_2$ | I | |
| 23.110 | Cl | F | $NO_2$ | $OCH_3$ | |
| 23.111 | Cl | F | $NO_2$ | $OCH_2OCH_3$ | |
| 23.112 | Cl | F | $NO_2$ | $OCH_2CH=CH_2$ | |
| 23.113 | Cl | F | $NO_2$ | $OCH_2C_6H_5$ | |
| 23.114 | Cl | F | $NO_2$ | OH | |
| 23.115 | Cl | F | $NO_2$ | $SCH_3$ | |
| 23.116 | Cl | F | $NO_2$ | $SCH_2CH=CH_2$ | |
| 23.117 | Cl | F | $NO_2$ | $SCH_2C_6H_5$ | |
| 23.118 | Cl | F | $NO_2$ | $SCOCH_3$ | |
| 23.119 | Cl | F | $NO_2$ | $SCOC_6H_5$ | |
| 23.120 | Cl | F | $NO_2$ | $OCH_2COOCH_3$ | |
| 23.121 | Cl | F | $NO_2$ | $OCH_2COOCH_2CH=CH_2$ | |
| 23.122 | Cl | F | $NO_2$ | $OCH_2COOCH_2C_6H_5$ | |
| 23.123 | Cl | F | $NO_2$ | $OCH_2COOH$ | |
| 23.124 | Cl | F | $NO_2$ | $OCH_2COCl$ | |
| 23.125 | Cl | F | $NO_2$ | $SCH_2COOCH_3$ | |
| 23.126 | Cl | F | $NO_2$ | $SCH_2COOCH_2CH=CH_2$ | |

TABLE 23-continued

Compounds of the formula Ix

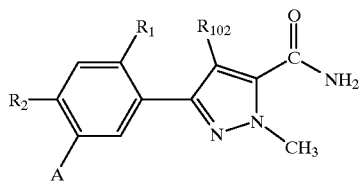

(Ix)

| Compound No. | $R_{102}$ | $R_1$ | $R_2$ | A | Physical data |
|---|---|---|---|---|---|
| 23.127 | Cl | F | $NO_2$ | $SCH_2COOCH_2C_6H_5$ | |
| 23.128 | Cl | F | $NO_2$ | $SCH_2COOH$ | |
| 23.129 | Cl | F | $NO_2$ | $SCH_2COCl$ | |
| 23.130 | Cl | F | Br | H | |
| 23.131 | Cl | F | Br | OH | |
| 23.132 | Cl | F | Br | $OCH_3$ | |
| 23.133 | Cl | F | Br | COOH | |
| 23.134 | Cl | F | Br | $COOCH_3$ | |
| 23.135 | Cl | F | Br | SH | |
| 23.136 | Cl | F | Br | I | |
| 23.137 | Cl | Cl | Cl | $OCH_3$ | |
| 23.138 | Cl | Cl | Cl | COOH | |
| 23.139 | Cl | Cl | Cl | $COOCH_3$ | |
| 23.140 | Cl | Cl | Cl | Br | |
| 23.141 | Cl | Cl | Cl | I | |
| 23.142 | Cl | Cl | Cl | SH | |
| 23.143 | Cl | F | Cl | $CH(CH_3)C\equiv CH$ | 165–166° C. |
| 23.144 | Cl | H | Cl | $SCH_2COOCH_3$ | 155–156° C. |
| 23.145 | Cl | F | Cl | COOH | 247–249° C. |
| 23.146 | Cl | F | Cl | $COOC(CH_3)COOC_2H_5$ | 108–109° C. |
| 23.147 | Br | F | Cl | $COOC(CH_3)COOC_2H_5$ | |
| 23.148 | Cl | F | Cl | $COOC(CH_3)COOH$ | |
| 23.149 | Br | F | Cl | $COOC(CH_3)COOH$ | |
| 23.150 | Cl | F | H | F | |
| 23.151 | Br | F | H | F | 158–159° C. |
| 23.152 | Cl | Cl | H | Cl | |
| 23.153 | Cl | F | F | H | 195–196° C. |
| 23.154 | Br | F | F | H | |
| 23.155 | Cl | F | F | $NO_2$ | |
| 23.156 | Br | F | F | $NO_2$ | |
| 23.157 | Cl | F | $NH_2$ | $OCH_3$ | |
| 23.158 | Br | F | $NH_2$ | $OCH_3$ | |
| 23.159 | Cl | F | $NH_2$ | $OCH_2$—C$_6$H$_5$ | |
| 23.160 | Br | F | $NH_2$ | $OCH_2$—C$_6$H$_5$ | |
| 23.161 | Cl | F | Cl | $OSO_2CF_3$ | |
| 23.162 | Br | F | Cl | $OSO_2CF_3$ | |
| 23.163 | Cl | F | Cl | $CH=CH-COOC_2H_5$ | solid |
| 23.164 | Cl | F | Cl | $OCH(CH_3)C\equiv CH$ | 165–166° C. |
| 23.165 | Br | F | Cl | $OCH(CH_3)C\equiv CH$ | |
| 23.166 | Cl | F | Cl | $COOC_2H_5$ | solid |
| 23.167 | Br | F | Cl | $COOC_2H_5$ | |
| 23.168 | Cl | F | Cl | C$_6$H$_5$ | |
| 23.169 | Cl | F | Cl | $N(CH_2CH=CH_2)_2$ | resin |
| 23.170 | Cl | F | Cl | $C\equiv C-CH_2OH$ | |
| 23.171 | Br | F | Cl | $C\equiv C-CH_2OH$ | 220–224° C. |
| 23.172 | Cl | F | Cl | $COOC(CH_3)_3$ | solid |
| 23.173 | Br | F | Cl | $COOC(CH_3)_3$ | |

TABLE 23-continued

Compounds of the formula Ix

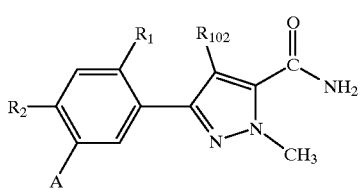

(Ix)

| Compound No. | $R_{102}$ | $R_1$ | $R_2$ | A | Physical data |
|---|---|---|---|---|---|
| 23.174 | Cl | F | Cl | COSCH(CH$_3$)$_2$ | |
| 23.175 | Br | F | Cl | COSCH(CH$_3$)$_2$ | solid |
| 23.176 | Cl | F | Cl | COOCH$_2$CH$_2$CN | |
| 23.177 | Cl | F | F | NH$_2$ | 197–198° C. |

TABLE 24

Compounds of the formula Iy

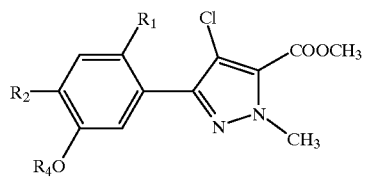

(Iy)

| Compound No. | $R_1$ | $R_2$ | $R_4$ | Physical data |
|---|---|---|---|---|
| 24.001 | H | Cl | H | |
| 24.002 | H | Br | H | |
| 24.003 | H | NO$_2$ | H | |
| 24.004 | H | CN | H | |
| 24.005 | F | Cl | H | |
| 24.006 | F | Br | H | |
| 24.007 | F | NO$_2$ | H | |
| 24.008 | F | CN | H | |
| 24.009 | Cl | Cl | H | |
| 24.010 | Cl | NO$_2$ | H | |
| 24.011 | H | Cl | CH$_3$ | |
| 24.012 | H | Br | CH$_3$ | |
| 24.013 | H | NO$_2$ | CH$_3$ | |
| 24.014 | H | CN | CH$_3$ | |
| 24.015 | F | Cl | CH$_3$ | solid |
| 24.016 | F | Br | CH$_3$ | |
| 24.017 | F | NO$_2$ | CH$_3$ | solid |
| 24.018 | F | CN | CH$_3$ | |
| 24.019 | Cl | Cl | CH$_3$ | |
| 24.020 | Cl | NO$_2$ | CH$_3$ | |
| 24.021 | H | Cl | —CH(CH$_3$)$_2$ | |
| 24.022 | H | Br | —CH(CH$_3$)$_2$ | |
| 24.023 | H | NO$_2$ | —CH(CH$_3$)$_2$ | |
| 24.024 | H | CN | —CH(CH$_3$)$_2$ | |
| 24.025 | F | Cl | —CH(CH$_3$)$_2$ | solid |
| 24.026 | F | Br | —CH(CH$_3$)$_2$ | |
| 24.027 | F | NO$_2$ | —CH(CH$_3$)$_2$ | |
| 24.028 | F | CN | —CH(CH$_3$)$_2$ | |
| 24.029 | Cl | Cl | —CH(CH$_3$)$_2$ | |
| 24.030 | Cl | NO$_2$ | —CH(CH$_3$)$_2$ | |
| 24.031 | H | Cl | —COOCH$_3$ | |
| 24.032 | H | Br | —COOCH$_3$ | |
| 24.033 | H | NO$_2$ | —COOCH$_3$ | |
| 24.034 | H | CN | —COOCH$_3$ | |
| 24.035 | F | Cl | —COOCH$_3$ | |
| 24.036 | F | Br | —COOCH$_3$ | |
| 24.037 | F | NO$_2$ | —COOCH$_3$ | |
| 24.038 | F | CN | —COOCH$_3$ | |
| 24.039 | Cl | Cl | —COOCH$_3$ | |
| 24.040 | Cl | NO$_2$ | —COOCH$_3$ | |
| 24.041 | H | Cl | —CH$_2$OCH$_3$ | |
| 24.042 | H | Br | —CH$_2$OCH$_3$ | |
| 24.043 | H | NO$_2$ | —CH$_2$OCH$_3$ | |
| 24.044 | H | CN | —CH$_2$OCH$_3$ | |
| 24.045 | F | Cl | —CH$_2$OCH$_3$ | |
| 24.046 | F | Br | —CH$_2$OCH$_3$ | |
| 24.047 | F | NO$_2$ | —CH$_2$OCH$_3$ | |
| 24.048 | F | CN | —CH$_2$OCH$_3$ | |
| 24.049 | Cl | Cl | —CH$_2$OCH$_3$ | |
| 24.050 | Cl | NO$_2$ | —CH$_2$OCH$_3$ | |
| 24.051 | H | Cl | —CH$_2$—C$_6$H$_5$ | |
| 24.052 | H | Br | —CH$_2$—C$_6$H$_5$ | |
| 24.053 | H | NO$_2$ | —CH$_2$—C$_6$H$_5$ | |
| 24.054 | H | CN | —CH$_2$—C$_6$H$_5$ | |
| 24.055 | F | Cl | —CH$_2$—C$_6$H$_5$ | |
| 24.056 | F | Br | —CH$_2$—C$_6$H$_5$ | |
| 24.057 | F | NO$_2$ | —CH$_2$—C$_6$H$_5$ | |
| 24.058 | F | CN | —CH$_2$—C$_6$H$_5$ | |
| 24.059 | Cl | CL | —CH$_2$—C$_6$H$_5$ | |
| 24.060 | Cl | NO$_2$ | —CH$_2$—C$_6$H$_5$ | |
| 24.061 | H | Cl | —CH$_2$—CH=CH$_2$ | |
| 24.062 | H | Br | —CH$_2$—CH=CH$_2$ | |
| 24.063 | H | NO$_2$ | —CH$_2$—CH=CH$_2$ | |
| 24.064 | H | CN | —CH$_2$—CH=CH$_2$ | |
| 24.065 | F | Cl | —CH$_2$—CH=CH$_2$ | |
| 24.066 | F | Br | —CH$_2$—CH=CH$_2$ | |
| 24.067 | F | NO$_2$ | —CH$_2$—CH=CH$_2$ | |
| 24.068 | F | CN | —CH$_2$—CH=CH$_2$ | |
| 24.069 | Cl | Cl | —CH$_2$—CH=CH$_2$ | |
| 24.070 | Cl | NO$_2$ | —CH$_2$—CH=CH$_2$ | |
| 24.071 | F | Cl | —CH$_2$COOH | |
| 24.072 | F | Cl | —CH(CH$_3$)COOH | |
| 24.073 | F | Cl | —C(CH$_3$)$_2$COOH | |
| 24.074 | F | NH$_2$ | —CH$_3$ | resin |

TABLE 24-continued

Compounds of the formula Iy

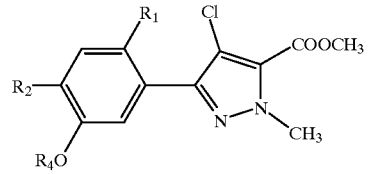

(Iy)

| Compound No. | R₁ | R₂ | R₄ | Physical data |
|---|---|---|---|---|
| 24.075 | F | NH₂ | —CH₂—C₆H₅ | |
| 24.076 | Cl | NH₂ | —CH₃ | |
| 24.077 | F | H | —CH₃ | |
| 24.078 | Cl | H | —CH₃ | |

TABLE 25

Compounds of the formula Iyy

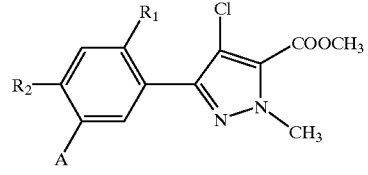

(Iyy)

| Compound No. | R₁ | R₂ | A | Physical data |
|---|---|---|---|---|
| 25.001 | H | Cl | NO₂ | |
| 25.002 | H | Cl | NH₂ | |
| 25.003 | H | Cl | Br | |
| 25.004 | H | Cl | I | |
| 25.005 | F | Cl | NO₂ | m.p. 166–167° C. |
| 25.006 | F | Cl | NH₂ | m.p. 127–128° C. |
| 25.007 | F | Cl | NHSO₂CH₃ | |
| 25.008 | F | Cl | N(SO₂CH₃)₂ | |
| 25.009 | F | Cl | SH | |
| 25.010 | F | Cl | SCH₃ | |
| 25.011 | F | Cl | SCH₂—C₆H₅ | |
| 25.012 | F | Cl | Br | |
| 25.013 | F | Cl | I | m.p. 166–167° C. |
| 25.014 | F | Cl | SCH₂COOH | |
| 25.015 | F | Cl | SCH(CH₃)COOH | |
| 25.016 | F | Cl | SC(CH₃)₂COOH | |
| 25.017 | Cl | Cl | NO₂ | m.p. 203–205° C. |
| 25.018 | Cl | Cl | NH₂ | solid |
| 25.019 | Cl | Cl | NHSO₂CH₃ | |
| 25.020 | Cl | Cl | N(SO₂CH₃)₂ | solid |
| 25.021 | F | Cl | N(CH₂CH=CH₂) | oil |
| 25.022 | Cl | Cl | SH | |
| 25.023 | Cl | Cl | SCH₃ | |
| 25.024 | Cl | Cl | SCH₂—C₆H₅ | |
| 25.025 | Cl | Cl | SCH₂COOH | |
| 25.026 | Cl | Cl | SCH(CH₃)COOH | |
| 25.027 | Cl | Cl | SC(CH₃)₂COOH | |
| 25.028 | Cl | Cl | Br | |
| 25.029 | Cl | Cl | I | |
| 25.030 | F | H | F | m.p. 89–91° C. |
| 25.031 | F | NO₂ | F | m.p. 160–162° C. |
| 25.032 | F | F | H | m.p. 151–152° C. |
| 25.033 | F | F | NO₂ | m.p. 156–158° C. |
| 25.034 | F | F | NH₂ | m.p. 91–92° C. |
| 25.035 | F | OCH₃ | NO₂ | |
| 25.036 | F | OH | NO₂ | |
| 25.037 | Cl | H | Cl | |
| 25.038 | Cl | NO₂ | Cl | |
| 25.039 | F | H | Br | |
| 25.040 | F | H | I | |
| 25.041 | Cl | NO₂ | Cl | |
| 25.042 | Cl | NO₂ | O | |
| 25.043 | F | Cl | H | m.p. 152° C. |

TABLE 26

Compounds of the formula Ixx

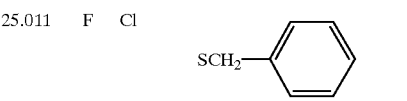

(Ixx)

| Compound No. | R₁ | R₂ | A | Physical data |
|---|---|---|---|---|
| 26.001 | F | Cl | H | m.p. 141–142° C. |
| 26.002 | F | Cl | OH | |
| 26.003 | F | Cl | OCH₃ | solid |
| 26.004 | F | Cl | OCH₂—C₆H₅ | |
| 26.005 | F | Cl | OCH₂COOCH₃ | |
| 26.006 | F | Cl | OCH₂COOC(CH₃)₃ | |
| 26.007 | F | Cl | OCH(CH₃)COOH | |
| 26.008 | F | Cl | OCH(CH₃)COOCH₂CH₃ | |

TABLE 26-continued

Compounds of the formula Ixx (Ixx)

| Compound No. | R₁ | R₂ | A | Physical data |
|---|---|---|---|---|
| 26.009 | F | Cl | OCH(CH$_3$)COOCH$_2$–C$_6$H$_5$ | |
| 26.010 | F | Cl | OCH(CH$_3$)COOCH$_2$–(2-F-C$_6$H$_4$) | |
| 26.011 | F | Cl | I | solid |
| 26.012 | F | Cl | OC(CH$_3$)$_2$COOH | |
| 26.013 | F | Cl | OC(CH$_3$)$_2$COOCH$_3$ | |
| 26.014 | F | Cl | OC(CH$_3$)$_2$COOCH$_2$–C$_6$H$_5$ | |
| 26.015 | F | Cl | SH | |
| 26.016 | F | Cl | SCH$_3$ | |
| 26.017 | F | Cl | SCH$_2$–C$_6$H$_5$ | |
| 26.018 | F | Cl | SCH(CH$_3$)$_2$ | |
| 26.019 | F | Cl | SCH$_2$COOCH$_3$ | |
| 26.020 | F | Cl | NH$_2$ | m.p. 134–136° C. |
| 26.021 | F | Cl | NHSO$_2$CH$_3$ | |
| 26.022 | H | Cl | H | solid |
| 26.023 | F | H | F | m.p. 88–91° C. |
| 26.024 | F | NO$_2$ | F | m.p. 165–166° C. |
| 26.025 | F | NO$_2$ | OCH$_3$ | |
| 26.026 | F | NH$_2$ | OCH$_3$ | |
| 26.027 | Cl | H | Cl | |
| 26.028 | Cl | NO$_2$ | Cl | |
| 26.029 | Cl | NO$_2$ | OCH$_3$ | |
| 26.030 | Cl | NH$_2$ | OCH$_3$ | |
| 26.031 | F | F | H | |
| 26.032 | F | F | NO$_2$ | |
| 26.033 | F | Cl | NO$_2$ | m.p. 163–166° C. |
| 26.034 | F | Cl | NH$_2$ | m.p. 134–136° C. |

TABLE 27

Compounds of the formula Iww (Iww)

| Compound No. | R₁ | R₂ | R$_{102}$ | R$_8$ | Physical data |
|---|---|---|---|---|---|
| 27.001 | H | Cl | Cl | H | |
| 27.002 | F | Cl | Cl | H | solid |
| 27.003 | Cl | Cl | Cl | H | |
| 27.004 | H | Cl | Cl | CH$_3$ | |
| 27.005 | F | Cl | Cl | CH$_3$ | |
| 27.006 | Cl | Cl | Cl | CH$_3$ | |
| 27.007 | H | Br | Cl | CH$_3$ | |
| 27.008 | F | Br | Cl | CH$_3$ | |
| 27.009 | Cl | Br | Cl | CH$_3$ | |
| 27.010 | H | Cl | Cl | CH$_2$CH$_3$ | |
| 27.011 | F | Cl | Cl | CH$_2$CH$_3$ | |
| 27.012 | Cl | Cl | Cl | CH$_2$CH$_3$ | |
| 27.013 | F | NO$_2$ | Cl | CH$_2$CH$_3$ | |
| 27.014 | F | NH$_2$ | Cl | CH$_2$CH$_3$ | |
| 27.015 | F | I | Cl | CH$_2$CH$_3$ | |
| 27.016 | H | NO$_2$ | Cl | CH$_2$CH$_3$ | |
| 27.017 | H | NH$_2$ | Cl | CH$_2$CH$_3$ | |
| 27.018 | H | I | Cl | CH$_2$CH$_3$ | |
| 27.019 | F | Cl | Br | H | |
| 27.020 | F | Cl | Br | CH$_3$ | |
| 27.021 | F | Cl | Br | CH$_2$CH$_3$ | |

TABLE 28

Compounds of the formula Ivv (Ivv)

| Compound No. | R₁ | R₂ | A | Physical data |
|---|---|---|---|---|
| 28.001 | H | Cl | H | solid |
| 28.002 | H | Cl | Br | |
| 28.003 | H | Cl | OCH$_3$ | |
| 28.004 | H | Cl | NO$_2$ | |
| 28.005 | H | Cl | SCH$_3$ | |
| 28.006 | H | Cl | COOH | |
| 28.007 | H | Cl | COOCH$_2$–C$_6$H$_5$ | |
| 28.008 | F | Cl | H | m.p. 125–126° C. |
| 28.009 | F | Cl | NO$_2$ | |
| 28.010 | F | Cl | NH$_2$ | |
| 28.011 | F | Cl | SH | |
| 28.012 | F | Cl | SCH$_3$ | |
| 28.013 | F | Cl | OH | |
| 28.014 | F | Cl | OCH$_3$ | solid |
| 28.015 | F | Cl | COOH | |

TABLE 28-continued

Compounds of the formula Ivv (Ivv)

| Compound No. | $R_1$ | $R_2$ | A | Physical data |
|---|---|---|---|---|
| 28.016 | F | Cl | COOCH$_2$–phenyl | |
| 28.017 | F | Cl | Br | |
| 28.018 | F | Cl | I | |
| 28.019 | F | Br | H | |
| 28.020 | F | Br | NO$_2$ | |
| 28.021 | F | Br | NH$_2$ | |
| 28.022 | F | Br | SH | |
| 28.023 | F | Br | SCH$_3$ | |
| 28.024 | F | Br | OH | |
| 28.025 | F | Br | OCH$_3$ | |
| 28.026 | F | Br | COOH | |
| 28.027 | F | Br | COOCH$_2$–phenyl | |
| 28.028 | F | Br | I | |
| 28.029 | F | Br | OSO$_2$CF$_3$ | |
| 28.030 | F | Cl | OSO$_2$CF$_3$ | |
| 28.031 | Cl | Cl | H | m.p. 154–155° C. |
| 28.032 | Cl | Cl | NO$_2$ | |
| 28.033 | Cl | Cl | NH$_2$ | |
| 28.034 | Cl | Cl | OH | |
| 28.035 | Cl | Cl | OCH$_3$ | |
| 28.036 | Cl | Cl | SH | |
| 28.037 | Cl | Cl | SCH$_3$ | |
| 28.038 | Cl | Cl | COOH | |
| 28.039 | Cl | Cl | COOCH$_2$–phenyl | |
| 28.040 | Cl | Cl | Br | |
| 28.041 | Cl | Cl | I | |
| 28.042 | F | H | F | m.p. 106–107° C. |
| 28.043 | Cl | H | Cl | |
| 28.044 | F | F | H | m.p. 91–92° C. solid |
| 28.045 | F | Cl | OCH(CH$_3$)$_2$ | |

TABLE 29

Compounds of the formula Iuu (Iuu)

| Compound No. | $R_{61}$ | $R_{22}$ | $R_{19}$ | Physical data |
|---|---|---|---|---|
| 29.001 | H | H | H | |
| 29.002 | H | F | H | |
| 29.003 | H | Cl | H | |
| 29.004 | H | H | CH(CH$_3$)$_2$ | |
| 29.005 | H | F | CH(CH$_3$)$_2$ | |
| 29.006 | H | Cl | CH(CH$_3$)$_2$ | |
| 29.007 | CH$_3$ | H | H | |
| 29.008 | CH$_3$ | F | H | |
| 29.009 | CH$_3$ | Cl | H | |
| 29.010 | CH$_3$ | H | CH(CH$_3$)$_2$ | |
| 29.011 | CH$_3$ | F | CH(CH$_3$)$_2$ | m.p. 208–210° C. |
| 29.012 | CH$_3$ | Cl | CH(CH$_3$)$_2$ | |
| 29.013 | CH$_3$ | H | CH$_2$CH=CH$_2$ | |
| 29.014 | CH$_3$ | F | CH$_2$CH=CH$_2$ | |
| 29.015 | CH$_3$ | Cl | CH$_2$CH=CH$_2$ | |
| 29.016 | CH$_3$ | H | CH$_2$C≡CH | |
| 29.017 | CH$_3$ | F | CH$_2$C≡CH | |
| 29.018 | CH$_3$ | Cl | CH$_2$C≡CH | |
| 29.019 | CH$_3$ | H | CH$_2$COOH | |
| 29.020 | CH$_3$ | F | CH$_2$COOH | |
| 29.021 | CH$_3$ | Cl | CH$_2$COOH | |
| 29.022 | CH$_3$ | H | CH$_2$—COOCH$_3$ | |
| 29.023 | CH$_3$ | F | CH$_2$—COOC$_2$H$_5$ | |
| 29.024 | CH$_3$ | F | CH(CH$_3$)COOC$_2$H$_5$ | |

TABLE 30

Compounds of the formula Itt (Itt)

| Compound No. | $R_{61}$ | $R_{22}$ | $R_{19}$ | Physical data |
|---|---|---|---|---|
| 30.001 | R | H | H | |
| 30.002 | H | F | H | |
| 30.003 | H | Cl | H | |
| 30.004 | H | H | CH$_2$CH=CH$_2$ | |
| 30.005 | H | F | CH$_2$CH=CH$_2$ | |
| 30.006 | H | Cl | CH$_2$CH=CH$_2$ | |
| 30.007 | H | H | CH$_2$C≡CH | |
| 30.008 | H | F | CH$_2$C≡CH | |
| 30.009 | H | Cl | CH$_2$C≡CH | |
| 30.010 | H | Cl | CH(CH$_3$)C≡CH | |

TABLE 31

Compounds of the formula Iu (Iu)

| Compound No. | $R_{102}$ | $R_1$ | $R_2$ | A | Physical data |
|---|---|---|---|---|---|
| 31.001 | H | H | Cl | H | |
| 31.002 | H | H | Cl | COOCH$_3$ | |
| 31.003 | H | H | Cl | NO$_2$ | |
| 31.004 | H | H | H | NH$_2$ | |
| 31.005 | H | H | Cl | I | |
| 31.006 | Cl | H | Cl | COOCH$_3$ | |
| 31.007 | Cl | H | C1. | NO$_2$ | |
| 31.008 | Cl | H | Cl | NH$_2$ | |
| 31.009 | Cl | H | Cl | I | |
| 31.010 | Cl | F | Cl | COOCH$_3$ | |
| 31.011 | Cl | F | Cl | NO$_2$ | |
| 31.012 | Cl | F. | Cl | NH$_2$ | |
| 31.013 | Cl | F | Cl | I | m.p. 208–211° C. |
| 31.014 | H | F | Cl | OH | |
| 31.015 | H | F | Cl | OCH$_3$ | |
| 31.016 | H | F | Cl | OCH(CH$_3$)$_2$ | |
| 31.017 | Cl | F | Cl | OH | |
| 31.018 | Cl | F | Cl | OCH$_3$ | m.p. 212–213° C. |
| 31.019 | Cl | F | Cl | OCH(CH$_3$)$_2$ | |
| 31.020 | Cl | F | Cl | OCH$_2$C≡CH | |
| 31.021 | Cl | F | Cl | COOCH(CH$_3$)$_2$ | |
| 31.022 | Cl | F | Br | OH | |
| 31.023 | Cl | F | Br | COOCH$_3$ | |
| 31.024 | Cl | F | Cl | Br | |
| 31.025 | Cl | F | Cl | H | solid |
| 31.026 | Cl | F | Cl | SH | |
| 31.027 | Cl | F | Cl | SCH$_3$ | |
| 31.028 | Cl | F | Cl | COOCH$_2$CH$_3$ | |
| 31.029 | Br | F | Cl | OCH$_3$ | solid |
| 31.030 | Br | F | Cl | SCH$_3$ | |
| 31.031 | Br | F | Cl | COOCH$_3$ | |
| 31.032 | Br | F | Cl | COOCH$_2$CH$_3$ | |
| 31.033 | Br | F | Cl | I | solid |
| 31.034 | Br | F | Cl | OH | |
| 31.035 | Br | F | Cl | SH | |
| 31.036 | Br | F | Cl | NH$_2$ | |
| 31.037 | Cl | Cl | Cl | OH | |
| 31.038 | Cl | Cl | Cl | OCH$_3$ | |
| 31.039 | Cl | Cl | Cl | SH | |
| 31.040 | Cl | Cl | Cl | SCH$_3$ | |
| 31.041 | Cl | Cl | Cl | COOCH$_2$CH$_3$ | |
| 31.042 | Cl | Cl | Cl | COOCH$_3$ | |
| 31.043 | Cl | F | H | F | |
| 31.044 | Br | F | H | F | m.p. 181–183° C. |
| 31.045 | Cl | F | F | H | |
| 31.046 | Br | F | F | H | |
| 31.047 | Cl | F | Cl | H | solid |
| 31.048 | Br | F | Cl | H | m.p. 196–198° C. |

TABLE 32

Compounds of the formula Irr (Irr)

| Compound No. | $R_{102}$ | $R_{22}$ | $R_{19}$ | Physical data |
|---|---|---|---|---|
| 32.001 | H | H | H | |
| 32.002 | H | H | CH(CH$_3$)$_2$ | |
| 32.003 | H | H | CH$_2$C≡CH | |
| 32.004 | H | H | CH$_2$COOC$_2$H$_5$ | |
| 32.005 | Cl | H | CH(CH$_3$)$_2$ | |
| 32.006 | Cl | H | CH$_2$C≡CH | |
| 32.007 | Cl | H | CH$_2$COOC$_2$H$_5$ | |
| 32.008 | Cl | H | CH(CH$_3$)C≡CH | |
| 32.009 | Cl | H | CH(CH$_3$)COOCH$_3$ | |
| 32.010 | Cl | F | CH(CH$_3$)$_2$ | |
| 32.011 | Cl | F | CH$_2$C≡CH | |
| 32.012 | Cl | F | CH$_2$CH=CH$_2$ | |
| 32.013 | Cl | F | CH(CH$_3$)C≡CH | |
| 32.014 | Cl | F | CH$_2$COOCH$_3$ | |
| 32.015 | Cl | F | CH$_2$COOCH$_2$CH$_3$ | |
| 32.016 | Cl | F | CH(CH$_3$)COOCH$_3$ | |
| 32.017 | Cl | F | CH(CH$_3$)COOCH$_2$CH$_3$ | |

TABLE 33

Compounds of the formula Iqq (Iqq)

| Compound No. | $R_{102}$ | $R_{22}$ | $R_{19}$ | Physical data |
|---|---|---|---|---|
| 33.001 | H | H | H | |
| 33.002 | H | F | H | |
| 33.003 | H | F | CH(CH$_3$)$_2$ | |
| 33.004 | H | F | CH$_2$—C≡CH | |
| 33.005 | H | F | CH$_2$—CH=CH$_2$ | |
| 33.006 | H | F | CH$_2$COOCH$_3$ | |
| 33.007 | H | F | CH(CH$_3$)COOCH$_3$ | |
| 33.008 | H | H | CH(CH$_3$)$_2$ | |
| 33.009 | H | H | CH$_2$C≡CH | |
| 33.010 | H | H | CH$_2$COOCH$_3$ | |
| 33.011 | Cl | F | CH(CH$_3$)$_2$ | m.p. 260–262° C. |
| 33.012 | Cl | F | CH$_2$C≡CH | |
| 33.013 | Cl | F | CH$_2$CH=CH$_2$ | |
| 33.014 | Cl | F | CH$_2$COOCH$_3$ | |

TABLE 34

Compounds of the formula Ipp

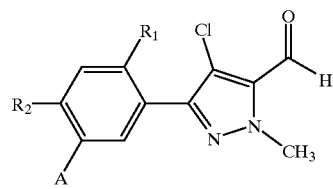

(Ipp)

| Compound No. | R₁ | R₂ | A | Physical data |
|---|---|---|---|---|
| 34.001 | H | Cl | COOCH₃ | |
| 34.002 | H | Cl | COOCH(CH₃)₂ | |
| 34.003 | H | Cl | COOH | |
| 34.004 | H | Cl | COOC(CH₃)₂COOCH₂CH=CH₂ | |
| 34.005 | F | Cl | OH | |
| 34.006 | F | Cl | OCH₃ | |
| 34.007 | F | Cl | OCH(CH₃)₂ | solid |
| 34.008 | F | Cl | OCH₂C≡CH | |
| 34.009 | F | Cl | OCH(CH₃)C≡CH | |
| 34.010 | F | Cl | OCH₂COOCH₃ | |
| 34.011 | F | Cl | OCH₂COOH | |
| 34.012 | F | Cl | OCH₂COO(CH₂)₄CH₃ | |
| 34.013 | F | Cl | SH | |
| 34.014 | F | Cl | SCH₃ | |
| 34.015 | F | Cl | Br | |
| 34.016 | F | Cl | I | |
| 34.017 | F | Cl | NH₂ | |
| 34.018 | F | Cl | COOCH₂CH₃ | |
| 34.019 | F | Cl | H | solid |
| 34.020 | F | Br | H | |
| 34.021 | F | Br | OH | |
| 34.022 | F | Br | OCH₃ | |
| 34.023 | F | Br | SH | |
| 34.024 | F | Br | SCH₃ | |
| 34.025 | F | Br | COOH | |
| 34.026 | F | Br | COOCH₂CH₃ | |
| 34.027 | F | Br | NH₂ | |
| 34.028 | F | Br | I | |
| 34.029 | Cl | Cl | OH | |
| 34.030 | Cl | Cl | OCH₃ | |
| 34.031 | Cl | Cl | SH | |
| 34.032 | Cl | Cl | SCH₃ | |
| 34.033 | Cl | Cl | COOH | |
| 34.034 | Cl | Cl | COOCH | |
| 34.035 | Cl | Cl | Br | |
| 34.036 | Cl | Cl | I | |
| 34.037 | Cl | Cl | NH₂ | |
| 34.038 | F | Cl | NO₂ | |
| 34.039 | F | Br | NO₂ | |
| 34.040 | Cl | Cl | NO₂ | |

TABLE 35

Compounds of the formula Ioo

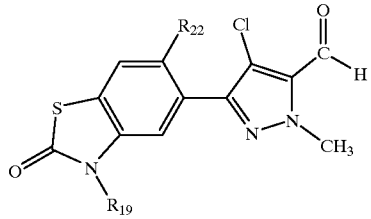

(Ioo)

| Compound No. | R₂₂ | R₁₉ | Physical data |
|---|---|---|---|
| 35.001 | H | H | |
| 35.002 | H | CH(CH₃)₂ | |
| 35.003 | H | CH₂COOH | |
| 35.004 | H | CH₂COOCH₃ | |
| 35.005 | H | CH₂C≡CH | |
| 35.006 | H | CH(CH₃)C≡CH | |
| 35.007 | F | H | |
| 35.008 | F | CH(CH₃)₂ | |
| 35.009 | F | CH₂COOH | |
| 35.010 | F | CH₂COOCH₃ | |
| 35.011 | F | CH₂C≡CH | |
| 35.012 | F | CH(CH₃)C≡CH | |
| 35.013 | F | CH(CH₃)COOC₂H₅ | |

TABLE 36

Compounds of the formula Inn

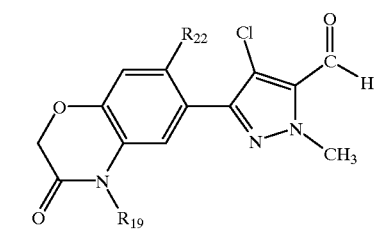

(Inn)

| Compound No. | R₂₂ | R₁₉ | Physical data |
|---|---|---|---|
| 36.001 | H | H | |
| 36.002 | H | CH(CH₃)₂ | |
| 36.003 | H | CH₂C≡CH | |
| 36.004 | H | CH₂COOH | |
| 36.005 | H | CH₂COOC₂H₅ | |
| 36.006 | H | CH₂COOCH₃ | |
| 36.007 | H | CH(CH₃)COOH | |
| 36.008 | H | CH(CH₃)COOCH₃ | |
| 36.009 | H | CH(CH₃)C≡CH | |
| 36.010 | F | H | |
| 36.011 | F | CH(CH₃)₂ | |
| 36.012 | F | CH₂C≡CH | |
| 36.013 | F | CH₂COOH | |
| 36.014 | F | CH₂COOCH₃ | |
| 36.015 | F | CH(CH₃)COOH | |
| 36.016 | F | CH(CH₃)COOCH₃ | |
| 36.017 | F | CH(CH₃)C≡CH | |

TABLE 37

Compounds of the formula Imm

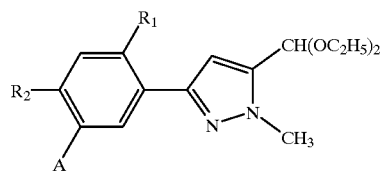
(Imm)

| Compound No. | R₁ | R₂ | A | Physical data |
|---|---|---|---|---|
| 37.001 | H | Cl | COOCH₃ | |
| 37.002 | H | Cl | COOH | |
| 37.003 | F | Cl | COOCH₃ | |
| 37.004 | F | Cl | COOCH(CH₃)₂ | |
| 37.005 | Cl | Cl | NO₂ | |
| 37.006 | Cl | Cl | NHSO₂CH₃ | |
| 37.007 | F | Cl | OH | |
| 37.008 | F | Cl | OCH₃ | m.p. 73–74° C. |
| 37.009 | F | Cl | OCH(CH₃)₂ | solid |
| 37.010 | F | Cl | OCH₂C≡CH | |
| 37.011 | F | Cl | OCH(CH₃)C≡CH | |
| 37.012 | F | Cl | OCH₂COO(CH₂)₄CH₃ | |
| 37.013 | Cl | Cl | OCH₃ | |
| 37.014 | Cl | Cl | COOCH₂CH₃ | |
| 37.015 | Cl | Cl | COOCH₃ | |
| 37.016 | Cl | Cl | SCH₃ | |
| 37.017 | Cl | Cl | I | |
| 37.018 | Cl | Cl | Br | |
| 37.019 | F | Cl | Br | |
| 37.020 | F | Cl | I | |
| 37.021 | H | Cl | H | oil |
| 37.022 | F | Cl | OCH₃ | oil |

TABLE 38

Compounds of the formula Ikk

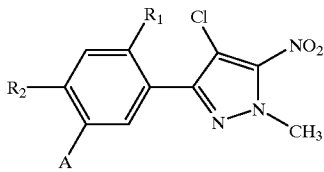
(Ikk)

| Compound No. | R₁ | R₂ | A | Physical data |
|---|---|---|---|---|
| 38.001 | H | NO₂ | F | |
| 38.002 | H | NO₂ | H | |
| 38.003 | H | NH₂ | H | |
| 38.004 | H | Cl | H | |
| 38.005 | H | Br | H | |
| 38.006 | H | CN | H | |
| 38.007 | H | CH₃ | H | |
| 38.008 | H | Cl | NO₂ | |
| 38.009 | H | Cl | NH₂ | |
| 38.010 | H | Cl | I | |
| 38.011 | H | Cl | COOH | |
| 38.012 | H | Cl | COCl | |
| 38.013 | H | Cl | COOCH₃ | |
| 38.014 | H | Cl | COOCH₂C₆H₅ | |
| 38.015 | H | Cl | COOCH₂CH=CH₂ | |
| 38.016 | F | NO₂ | H | |
| 38.017 | F | NO₂ | F | |
| 38.018 | F | NO₂ | COOCH₃ | |
| 38.019 | F | NO₂ | OH | |
| 38.020 | F | NO₂ | OCH₃ | |
| 38.021 | F | NO₂ | OCH₂OCH₃ | |

TABLE 38-continued

Compounds of the formula Ikk

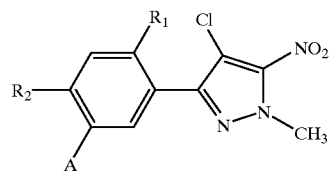
(Ikk)

| Compound No. | R₁ | R₂ | A | Physical data |
|---|---|---|---|---|
| 38.022 | F | NO₂ | OCH₂C₆H₅ | |
| 38.023 | F | NH₂ | OCH₃ | |
| 38.024 | F | NH₂ | OCH₂C₆H₅ | |
| 38.025 | F | NH₂ | OCH₂OCH₃ | |
| 38.026 | F | NH₂ | COOCH₂C₆H₅ | |
| 38.027 | F | Cl | H | |
| 38.028 | F | CL | NO₂ | |
| 38.029 | F | Cl | NH₂ | |
| 38.030 | F | Cl | OH | |
| 38.031 | F | Cl | I | |
| 38.032 | F | Cl | COOCH₃ | |
| 38.033 | F | Cl | CH₂OH | |
| 38.034 | F | Cl | CH₂Cl | |
| 38.035 | F | Cl | CHO | |
| 38.036 | F | Cl | —COCH₃ | |
| 38.037 | F | Cl | —CH(OCH₃)₂ | |
| 38.038 | F | Cl | —COOH | |
| 38.039 | F | Cl | —COOCH₂C₆H₅ | |
| 38.040 | F | Cl | —COOCH(CH₃)₂ | |
| 38.041 | F | Cl | —COO—CH₂CH=CH₂ | |
| 38.042 | F | Cl | —COOCH₂COOCH₃ | |
| 38.043 | F | Cl | —COOCH₂COOCH₂C₆H₅ | |
| 38.044 | F | Cl | —COOCH₂COOH | |
| 38.045 | F | Cl | —COOCH₂COCl | |
| 38.046 | F | Cl | —OCH₃ | |
| 38.047 | F | Cl | —OCH₂—CH=CH₂ | |
| 38.048 | F | Cl | —OCH₂COOCH₃ | |
| 38.049 | F | Cl | —OCH₂COOH | |
| 38.050 | F | Cl | —OCH₂COCl | |
| 38.051 | F | Cl | —OCH₂—C≡CH | |
| 38.052 | F | Cl | —OCH(CH₃)₂ | |

TABLE 39

Compounds of the formula IIc

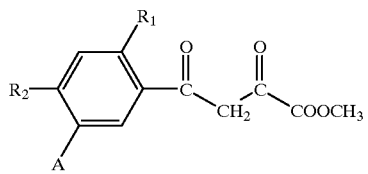
(IIc)

| Compound No. | R₁ | R₂ | A | Physical data |
|---|---|---|---|---|
| 39.001 | F | Cl | H | |
| 39.002 | F | Cl | OCH₃ | solid |
| 39.003 | F | Cl | SCH₃ | |
| 39.004 | F | Cl | COOCH₂CH₃ | |
| 39.005 | F | Cl | COOCH₃ | |
| 39.006 | F | Cl | Br | |
| 39.007 | F | Cl | I | |
| 39.008 | F | Cl | COOH | |
| 39.009 | F | Br | H | |
| 39.010 | F | Br | OCH₃ | |
| 39.011 | F | Br | SCH₃ | |
| 39.012 | F | Br | COOH | |

TABLE 39-continued

Compounds of the formula IIc

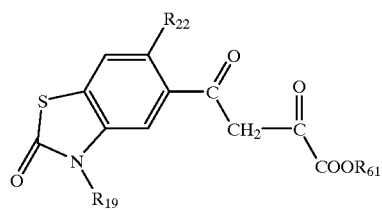

(IIc)

| Compound No. | $R_1$ | $R_2$ | A | Physical data |
|---|---|---|---|---|
| 39.013 | F | Br | $COOCH_3$ | |
| 39.014 | F | Br | $COOCH_2CH_3$ | |
| 39.015 | F | Br | I | |
| 39.016 | Cl | Cl | H | m.p. 135–137° C. |
| 39.017 | Cl | Cl | $OCH_3$ | |
| 39.018 | Cl | Cl | $SCH_3$ | |
| 39.019 | Cl | Cl | COOH | |
| 39.020 | Cl | Cl | $COOCH_3$ | |
| 39.021 | Cl | Cl | $COOCH_2CH_3$ | |
| 39.022 | Cl | Cl | Br | |
| 39.023 | Cl | Cl | I | |
| 39.024 | F | H | F | m.p. 141–143° C. |
| 39.025 | F | F | H | |
| 39.026 | F | Cl | $OCH(CH_3)_2$ | solid |

TABLE 40

Compounds of the formula IIii (IIii)

| Compound No. | $R_{61}$ | $R_{22}$ | $R_{19}$ | Physical data |
|---|---|---|---|---|
| 40.001 | H | H | $CH(CH_3)_2$ | |
| 40.002 | H | F | $CH(CH_3)_2$ | |
| 40.003 | H | Cl | $CH(CH_3)_2$ | |
| 40.004 | $CH_3$ | H | $CH(CH_3)_2$ | |
| 40.005 | $CH_3$ | F | $CH(CH_3)_2$ | m.p. 172° C. |
| 40.006 | $CH_3$ | Cl | $CH(CH_3)_2$ | |
| 40.007 | $CH_2CH_3$ | H | $CH(CH_3)_2$ | |
| 40.008 | $CH_2CH_3$ | F | $CH(CH_3)_2$ | |
| 40.009 | $CH_2CH_3$ | Cl | $CH(CH_3)_2$ | |
| 40.010 | H | H | $CH_2CH=CH_2$ | |
| 40.011 | H | F | $CH_2CH=CH_2$ | |
| 40.012 | H | Cl | $CH_2CH=CH_2$ | |
| 40.013 | $CH_3$ | H | $CH_2CH=CH_2$ | |
| 40.014 | $CH_3$ | F | $CH_2CH=CH_2$ | |
| 40.015 | $CH_3$ | Cl | $CH_2CH=CH_2$ | |
| 40.016 | H | H | H | |
| 40.017 | H | F | H | |
| 40.018 | H | Cl | H | |
| 40.019 | $CH_3$ | H | H | |
| 40.020 | $CH_3$ | F | H | |
| 40.021 | $CH_3$ | Cl | H | |

TABLE 41

Compounds of the formula IIb

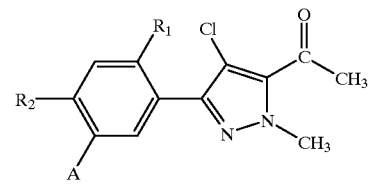

(IIb)

| Compound No. | $R_{61}$ | $R_{22}$ | $R_{19}$ | Physical data |
|---|---|---|---|---|
| 41.001 | H | H | H | |
| 41.002 | H | F | H | |
| 41.003 | H | Cl | H | |
| 41.004 | H | H | $CH_2CH=CH_2$ | |
| 41.005 | H | F | $CH_2CH=CH_2$ | |
| 41.006 | H | Cl | $CH_2CH=CH_2$ | |
| 41.007 | $CH_3$ | H | H | m.p. 227–232° C. |
| 41.008 | $CH_3$ | F | H | |
| 41.009 | $CH_3$ | Cl | H | |
| 41.010 | $CH_3$ | H | $CH_2CH=CH_2$ | |
| 41.011 | $CH_3$ | F | $CH_2CH=CH_2$ | |
| 41.012 | $CH_3$ | Cl | $CH_2CH=CH_2$ | |
| 41.013 | $CH_3$ | H | $CH_2C\equiv CH$ | m.p. 166–168° C. |
| 41.014 | $CH_3$ | F | $CH_2C\equiv CH$ | |
| 41.015 | $CH_3$ | Cl | $CH_2C\equiv CH$ | |
| 41.016 | $CH_3$ | H | $CH_2COOH$ | |
| 41.017 | $CH_3$ | F | $CH_2COOH$ | |
| 41.018 | $CH_3$ | Cl | $CH_2COOH$ | |

TABLE 42

Compounds of the formula Ihh (Ihh)

| Compound No. | $R_1$ | $R_2$ | A | Physical data |
|---|---|---|---|---|
| 42.001 | H | Cl | COOH | |
| 42.002 | H | Cl | $COOCH_3$ | |
| 42.003 | F | Cl | COOH | |
| 42.004 | F | Cl | $COOCH_3$ | |
| 42.005 | H | Cl | $COOCH(CH_3)_2$ | |
| 42.006 | F | Cl | $COOCH(CH_3)_2$ | |
| 42.007 | Cl | Cl | $NO_2$ | |
| 42.008 | Cl | Cl | $NH_2$ | |
| 42.009 | Cl | Cl | $NH(SO_2CH_3)$ | |
| 42.010 | Cl | Cl | $N(SO_2CH_3)_2$ | |
| 42.011 | F | Cl | OH | |
| 42.012 | F | Cl | $OCH_3$ | |
| 42.013 | F | Cl | $OCH(CH_3)_2$ | resin |
| 42.014 | F | Cl | $OCH_2C\equiv CH$ | |
| 42.015 | F | Cl | $OCH(CH_3)C\equiv CH$ | |
| 42.016 | F | Cl | $COSCH(CH_3)_2$ | |
| 42.017 | Cl | Cl | COOH | |
| 42.018 | F | Cl | $COOCH_2CH=CH_2$ | |
| 42.019 | F | Cl | $COOCH_2CH_3$ | |
| 42.020 | F | Cl | $COOC(CH_3)_2COOCH_2CH_3$ | |
| 42.021 | F | Cl | $COOC(CH_3)_2COOH$ | |
| 42.022 | F | Cl | $COOCH(CH_3)COOCH_3$ | |

TABLE 42-continued

Compounds of the formula Ihh

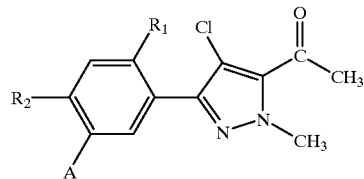

(Ihh)

| Compound No. | $R_1$ | $R_2$ | A | Physical data |
|---|---|---|---|---|
| 42.023 | F | Cl | COOCH$_2$COOH | |
| 42.024 | F | Cl | Br | |
| 42.025 | F | Cl | I | |
| 42.026 | F | Cl | NO$_2$ | |
| 42.027 | F | Cl | NH$_2$ | |
| 42.028 | F | Cl | N(SO$_2$CH$_3$)$_2$ | |
| 42.029 | F | Cl | NHSO$_2$CH$_3$ | |
| 42.030 | F | Cl | SH | |
| 42.031 | F | Cl | SCH$_3$ | |
| 42.032 | F | Cl | SCH(CH$_3$)COOCH$_2$CH$_3$ | |
| 42.033 | F | Cl | OCH(CH$_3$)COOH | |
| 42.034 | F | Cl | OCH(CH$_3$)COOCH$_2$CH=CH$_2$ | |

TABLE 43

Compounds of the formula IIIvv

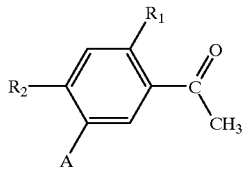

(IIIvv)

| Compound No. | $R_1$ | $R_2$ | A | Physical data |
|---|---|---|---|---|
| 43.001 | F | NO$_2$ | H | |
| 43.002 | F | NO$_2$ | OH | |
| 43.003 | F | NO$_2$ | OCH$_3$ | m.p. 111–112° C. |
| 43.004 | F | NO$_2$ | OCH$_2$CH=CH$_2$ | |
| 43.005 | F | NO$_2$ | OCH(CH$_3$)$_2$ | |
| 43.006 | F | NO$_2$ | Cl | |
| 43.007 | F | NO$_2$ | F | oil |
| 43.008 | F | NO$_2$ | NH$_2$ | |
| 43.009 | F | NO$_2$ | I | |
| 43.010 | F | NO$_2$ | Br | |
| 43.011 | F | NO$_2$ | COOH | |
| 43.012 | F | NO$_2$ | COOCH$_3$ | |
| 43.013 | F | NO$_2$ | SH | |
| 43.014 | F | NO$_2$ | SCH$_3$ | |
| 43.015 | F | NH$_2$ | OH | |
| 43.016 | F | NH$_2$ | OCH$_3$ | solid |
| 43.017 | F | NH$_2$ | SH | |
| 43.018 | F | NH$_2$ | SCH$_3$ | |
| 43.019 | F | NH$_2$ | COOH | |
| 43.020 | F | NH$_2$ | COOCH$_3$ | |
| 43.021 | F | NH$_2$ | I | |
| 43.022 | F | NH$_2$ | Br | |
| 43.023 | F | Cl | H | oil |
| 43.024 | F | Cl | OCH(CH$_3$)$_2$ | solid |
| 43.025 | F | Cl | OCH$_2$CH=CH$_2$ | |
| 43.026 | F | Cl | OCH$_2$C≡CH | |
| 43.027 | F | Cl | OCOOCH$_3$ | |
| 43.028 | F | Cl | NO$_2$ | |
| 43.029 | F | Cl | COOH | |
| 43.030 | F | Cl | COOCH$_3$ | |

TABLE 43-continued

Compounds of the formula IIIvv

| Compound No. | $R_1$ | $R_2$ | A | Physical data |
|---|---|---|---|---|
| 43.031 | F | Cl | NH$_2$ | |
| 43.032 | F | Cl | I | |
| 43.033 | F | Cl | Br | |
| 43.034 | F | Cl | COOCH(CH$_3$)$_2$ | |
| 43.035 | F | Cl | Cl | |
| 43.036 | F | Cl | OCH$_2$COOC$_2$H$_5$ | |
| 43.037 | F | Cl | SH | |
| 43.038 | F | Cl | SCH$_3$ | |
| 43.039 | F | Cl | CH$_2$Cl | |
| 43.040 | F | Br | COOH | |
| 43.041 | F | Br | COOCH$_3$ | |
| 43.042 | F | Br | OH | |
| 43.043 | F | Br | OCH$_3$ | |
| 43.044 | F | Br | NH$_2$ | |
| 43.045 | F | Br | NO$_2$ | |
| 43.046 | F | Br | H | |
| 43.047 | F | Br | SH | |
| 43.048 | F | Br | SCH$_3$ | |
| 43.049 | F | Br | SO$_2$Cl | |
| 43.050 | F | Br | CH$_2$Cl | |
| 43.051 | F | Br | COOH | |
| 43.052 | F | Br | COOCH$_3$ | |
| 43.053 | F | Br | OH | |
| 43.054 | F | Br | OCH$_3$ | |
| 43.055 | F | Br | NO$_2$ | |
| 43.056 | F | Br | SH | |
| 43.057 | F | Br | SCH$_3$ | |
| 43.058 | F | Br | CH$_2$Cl | |
| 43.059 | F | OCHF$_2$ | H | |
| 43.060 | F | OCF$_3$ | H | |
| 43.061 | F | OH | OH | |
| 43.062 | F | —O—CF$_2$—O— | | |
| 43.063 | F | OH | OCH$_3$ | |
| 43.064 | F | OH | COOH | |
| 43.065 | F | OH | COOCH$_3$ | |
| 43.066 | F | OH | SCH$_3$ | |
| 43.067 | F | OCH$_3$ | SH | |
| 43.068 | H | OH | OH | |
| 43.069 | F | OH | NO$_2$ | |
| 43.070 | F | OCH$_3$ | NH$_2$ | |
| 43.071 | F | OH | NH$_2$ | |
| 43.072 | F | OCH$_3$ | COOH | |
| 43.073 | F | OCH$_3$ | NO$_2$ | |
| 43.074 | F | OCH$_3$ | COOCH$_3$ | |
| 43.075 | F | OCH$_3$ | NH$_2$ | |
| 43.076 | F | OCH$_3$ | I | |
| 43.077 | F | OCH$_3$ | SH | |
| 43.078 | F | OCF$_3$ | COOH | |
| 43.079 | F | OCF$_3$ | SH | |
| 43.080 | F | OCF$_3$ | OH | |
| 43.081 | F | OCHF$_2$ | OH | |
| 43.082 | F | OCHF$_2$ | COOH | |
| 43.083 | F | OCHF$_2$ | SH | |
| 43.084 | F | CF$_3$ | NO$_2$ | |
| 43.085 | F | CF$_3$ | NH$_2$ | |
| 43.086 | F | CF$_3$ | OH | |
| 43.087 | F | CF$_3$ | COOH | |
| 43.088 | F | CF$_3$ | SH | |
| 43.089 | F | CF$_3$ | SCH$_3$ | |
| 43.090 | F | CF$_3$ | OCH$_3$ | |
| 43.091 | F | CF$_3$ | COOCH$_3$ | |
| 43.092 | F | CN | OH | |
| 43.093 | F | CN | SH | |

TABLE 43-continued

Compounds of the formula IIIvv

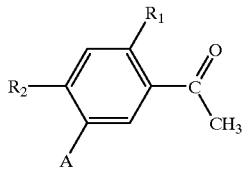

(IIIvv)

| Compound No. | $R_1$ | $R_2$ | A | Physical data |
|---|---|---|---|---|
| 43.094 | F | CN | $OCH_3$ | |
| 43.095 | F | CN | $SCH_3$ | |
| 43.096 | F | CN | $NH_2$ | |
| 43.097 | F | CN | $NO_2$ | |
| 43.098 | F | CN | COOH | |
| 43.099 | F | CN | $COOCH_3$ | |
| 43.100 | Cl | Cl | Br | |
| 43.101 | Cl | Cl | I | |
| 43.102 | Cl | Cl | COOH | |
| 43.103 | Cl | Cl | $COOCH_3$ | |
| 43.104 | Cl | Cl | $COOCH_2CH_3$ | |
| 43.105 | Cl | Cl | $OCH_3$ | |
| 43.106 | Cl | Cl | OH | |
| 43.107 | Cl | Cl | $SCH_3$ | |
| 43.108 | Cl | Cl | SH | |
| 43.109 | F | Cl | $OCH_3$ | solid |
| 43.110 | F | Cl | $NO_2$ | |
| 43.111 | Cl | Cl | $NO_2$ | solid |

TABLE 44

Compounds of the formula IIIa

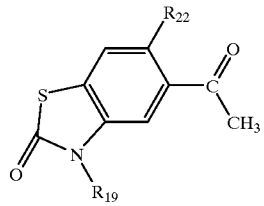

(IIIa)

| Compound No. | $R_{22}$ | $R_{19}$ | Physical data |
|---|---|---|---|
| 44.001 | H | H | m.p. 197–199° C. |
| 44.002 | F | H | m.p. 248–250° C. |
| 44.003 | Cl | H | |
| 44.004 | H | $CH(CH_3)_2$ | |
| 44.005 | F | $CH(CH_3)_2$ | m.p. 194–196° C. |
| 44.006 | Cl | $CH(CH_3)_2$ | |
| 44.007 | H | $CH_2CH=CH_2$ | |
| 44.008 | F | $CH_2CH=CH_2$ | |
| 44.009 | Cl | $CH_2CH=CH_2$ | |
| 44.010 | H | $CH_2COOH$ | |
| 44.011 | F | $CH_2COOH$ | |
| 44.012 | Cl | $CH_2COOH$ | |
| 44.013 | H | $CH_2COOCH_3$ | |
| 44.014 | F | $CH_2COOCH_3$ | |
| 44.015 | Cl | $CH_2COOCH_3$ | |
| 44.016 | H | $CH_2C\equiv CH$ | |
| 44.017 | F | $CH_2C\equiv CH$ | |
| 44.018 | Cl | $CH_2C\equiv CH$ | |
| 44.019 | H | $CH_2COOH$ | |
| 44.020 | F | $CH_2COOH$ | |
| 44.021 | Cl | $CH_2COOH$ | |
| 44.022 | H | $CH(CH_3)COOC_2H_5$ | m.p. 85–87° C. |

TABLE 45

Compounds of the formula IIIb

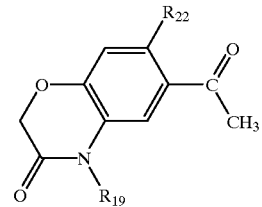

(IIIb)

| Compound No. | $R_{22}$ | $R_{19}$ | Physical data |
|---|---|---|---|
| 45.001 | H | H | |
| 45.002 | F | H | |
| 45.003 | Cl | H | |
| 45.004 | H | $CH_2CH=CH_2$ | |
| 45.005 | F | $CH_2CH=CH_2$ | |
| 45.006 | Cl | $CH_2CH=CH_2$ | |
| 45.007 | H | $CH_2COOH$ | |
| 45.008 | F | $CH_2COOH$ | |
| 45.009 | Cl | $CH_2COOH$ | |
| 45.010 | H | $CH_2COOCH_3$ | |
| 45.011 | F | $CH_2COOCH_3$ | |
| 45.012 | Cl | $CH_2COOCH_3$ | |
| 45.013 | H | $CH_2C\equiv CH$ | m.p. 123–125° C. |
| 45.014 | F | $CH_2C\equiv CH$ | |
| 45.015 | Cl | $CH_2C\equiv CH$ | |

Formulation examples for active ingredients of the formula I (%=percent by weight)

| F1. Emulsion concentrates | a) | b) | c) | d) |
|---|---|---|---|---|
| Active ingredient according to Tables 1–18 and 23–31 | 5% | 10% | 25% | 50% |
| Calcium dodecylbenzenesulfonate | 6% | 8% | 6% | 8% |
| Castor oil polyglycol ether (36 mol of EO) | 4% | — | 4% | 4% |
| Octylphenol polyglycol ether (7–8 mol of EO) | — | 4% | — | 2% |
| Cyclohexanone | — | — | 10% | 20% |
| Aromatic $C_9$–$C_{12}$ hydrocarbon mixture | 85% | 78% | 55% | 16% |

Emulsions of any desired concentration can be prepared from such concentrates by dilution with water.

| F2. Solutions | a) | b) | c) | d) |
|---|---|---|---|---|
| Active ingredient according to Tables 1–18 and 23–31 | 5% | 10% | 50% | 90% |
| 1-Methoxy-3-(3-methoxy-propoxy)-propane | — | 20% | 20% | — |
| Polyethylene glycol MW 400 | 20% | 10% | — | — |
| N-Methyl-2-pyrrolidone | — | — | 30% | 10% |
| Aromatic $C_9$–$C_{12}$ hydrocarbon mixture | 75% | 60% | — | — |

The solutions are suitable for use in the form of tiny drops.

| F3. Wettable powders | a) | b) | c) | d) |
|---|---|---|---|---|
| Active ingredient according to Tables 1–18 and 23–31 | 5% | 25% | 50% | 80% |
| Sodium ligninsulfonate | 4% | — | 3% | — |
| Sodium lauryl sulfate | 2% | 3% | — | 4% |
| Sodium diisobutyl-naphthalenesulfonate | — | 6% | 5% | 6% |
| Octylphenol polyglycol ether (7–8 mol of EO) | — | 1% | 2% | — |
| Highly disperse silicic acid | 1% | 3% | 5% | 10% |
| Kaolin | 88% | 62% | 35% | — |

The active ingredient is mixed thoroughly with the additives and the mixture is ground thoroughly in a suitable mill. Wettable powders which can be diluted with water to give suspensions of any desired concentration are obtained.

| F4. Coated granules | a) | b) | c) |
|---|---|---|---|
| Active ingredient according to Tables 1–18 and 23–31 | 0.1% | 5% | 15% |
| Highly disperse silicic acid | 0.9% | 2% | 2% |
| Inorganic carrier material (∅0.1–1 mm) for example CaCO$_3$ or SiO$_2$ | 99.0% | 93% | 83% |

The active ingredient is dissolved in methylene chloride and sprayed onto the carrier and the solvent is then evaporated off in vacuo.

| F5. Coated granules | a) | b) | c) |
|---|---|---|---|
| Active ingredient according to Tables 1–18 and 23–31 | 0.1% | 5% | 15% |
| Polyethylene glycol MW 200 | 1.0% | 2% | 3% |
| Highly disperse silicic acid | 0.9% | 1% | 2% |
| Inorganic carrier material (∅0.1–1 mm) for example CaCO$_3$ or SiO$_2$ | 98.0% | 92% | 80% |

The finely ground active ingredient is uniformly applied, in a mixer, to the carrier material which has been moistened with polyethylene glycol. Dust-free coated granules are obtained in this manner.

| F6. Extruded granules | a) | b) | c) | d) |
|---|---|---|---|---|
| Active ingredient according to Tables 1–18 and 23–31 | 0.1% | 3% | 5% | 15% |
| Sodium ligninsulfonate | 1.5% | 2% | 3% | 4% |
| Carboxymethylcellulose | 1.4% | 2% | 2% | 2% |
| Kaolin | 97.0% | 93% | 90% | 79% |

The active ingredient is mixed with the additives and the mixture is ground and moistened with water. This mixture is extruded and then dried in a stream of air.

| F7. Dusts | a) | b) | c) |
|---|---|---|---|
| Active ingredient according to Tables 1–18 and 23–31 | 0.1% | 1% | 5% |
| Talc | 39.9% | 49% | 35% |
| Kaolin | 60.0% | 50% | 60% |

Ready-to-use dusts are obtained by mixing the active ingredient with the carriers and grinding the mixture on a suitable mill.

| F8. Suspension concentrates | a) | b) | c) | d) |
|---|---|---|---|---|
| Active ingredient according to Tables 1–18 and 23–31 | 3% | 10% | 25% | 50% |
| Ethylene glycol | 5% | 5% | 5% | 5% |
| Nonylphenol polyglycol ether (15 mol of EO) | — | 1% | 2% | — |
| Sodium ligninsulfonate | 3% | 3% | 4% | 5% |
| Carboxymethylcellulose | 1% | 1% | 1% | 1% |
| 37% aqueous formaldehyde solution | 0.2% | 0.2% | 0.2% | 0.2% |
| Silicone oil emulsion | 0.8% | 0.8% | 0.8% | 0.8% |
| Water | 87% | 79% | 62% | 38% |

The finely ground active ingredient is intimately mixed with the additives. A suspension concentrate is thus obtained, from which suspensions of any desired concentration can be prepared by dilution with water.

Biological Examples

EXAMPLE B1

Herbicidal Action before Emergence of the Plants (Pre-emergence)

Monocotyledonous and dicotyledonous test plants are sown in sandy soil in plastic pots. Immediately after sowing, the test substances are sprayed on in an aqueous suspension prepared from a 25% wettable powder (Example F3, b)), corresponding to a dosage of 2000 g of AS/ha (500l of water/ha). The test plants are then grown in a greenhouse under optimum conditions. After a test period of 3 weeks, the test is evaluated with a nine-level scale of ratings (1=complete damage, 9=no action). Rating scores of 1 to 4 (in particular 1 to 3) mean a good to very good herbicidal action.

Test plants: Setaria, Sinapis, Solanum, Stellaria, Ipomoea.

The compounds according to the invention show a good herbicidal action.

Examples of the good herbicidal action are listed in Table B1.

TABLE B1

| | Pre-emergence action: | | | |
|---|---|---|---|---|
| Test plant: Active ingredient No. | Setaria | Solanum | Stellaria | Ipomoea |
| 1.032 | 1 | 1 | 1 | 1 |
| 1.045 | 6 | 1 | 1 | 4 |
| 4.005 | 3 | 1 | 1 | 2 |
| 6.011 | 1 | 1 | 1 | 3 |
| 6.025 | 1 | 1 | 1 | 2 |
| 6.034 | 1 | 1 | 1 | 2 |
| 6.064 | 9 | 1 | 1 | 1 |
| 6.098 | 1 | 1 | 1 | 2 |

TABLE B1-continued

| | Pre-emergence action: | | | |
|---|---|---|---|---|
| Test plant:<br>Active<br>ingredient No. | Setaria | Solanum | Stellaria | Ipomoea |
| 6.129 | 1 | 1 | 2 | 6 |
| 6.174 | 4 | 1 | 4 | 5 |
| 6.193 | 1 | 1 | 1 | 3 |
| 11.07 | 1 | 1 | 1 | 3 |
| 12.15 | 8 | 1 | 1 | 3 |
| 15.009 | 1 | 1 | 1 | 2 |
| 15.031 | 1 | 1 | 1 | 2 |
| 42.013 | 1 | 1 | 3 | 4 |

The same results are obtained if the compounds of the formula I are formulated according to Examples F1, F2 and F4 to F8.

EXAMPLE B2

Post-emergence Herbicidal Action (Contact Herbicide)

Monocotyledonous and dicotyledonous test plants are grown in a greenhouse in plastic pots with standard soil, and in the 4- to 6-leaf stage are sprayed with an aqueous suspension of the test substances of the formula I prepared from a 25% wettable powder (Example F3, b)), corresponding to a dosage of 2000 g of AS/ha (500 l of water/ha). The test plants are then grown on in a greenhouse under optimum conditions. After a test period of about 18 days, the experiment is evaluated with a nine-level scale of ratings (1=complete damage, 9=no action). Rating scores of 1 to 4 (in particular 1 to 3) mean a good to very good herbicidal action.

In this experiment also, the compounds of the formula I according to the invention show a good herbicidal action.

Table B2 shows examples of the good herbicidal activity of the compounds of the formula I.

TABLE B2

| | Post-emergence action: | | | | |
|---|---|---|---|---|---|
| Test plant:<br>Active<br>ingredient No. | Setaria | Sinapis | Solanum | Stellaria | Ipomoea |
| 1.032 | 1 | 2 | 1 | 2 | 1 |
| 1.045 | 3 | 1 | 1 | 1 | 1 |
| 4.005 | 2 | 1 | 1 | 1 | 1 |
| 6.011 | 1 | 1 | 1 | 1 | 1 |
| 6.025 | 1 | 1 | 1 | 1 | 1 |
| 6.034 | 2 | 1 | 1 | 1 | 1 |
| 6.064 | 6 | 2 | 1 | 2 | 1 |
| 6.098 | 1 | 1 | 1 | 1 | 1 |
| 6.129 | 2 | 1 | 1 | 2 | 1 |
| 6.174 | 3 | 1 | 1 | 1 | 1 |
| 6.193 | 2 | 1 | 1 | 1 | 1 |
| 11.07 | 1 | 1 | 1 | 1 | 1 |
| 12.15 | 5 | 1 | 1 | 1 | 1 |
| 15.009 | 1 | 1 | 1 | 1 | 1 |
| 15.031 | 2 | 1 | 1 | 1 | 1 |
| 42.013 | 1 | 3 | 1 | 2 | 1 |

The same results are obtained if the compounds of the formula I are formulated according to Examples F1, F2 and F4 to F8.

What is claimed is:

1. A compound of the formula I

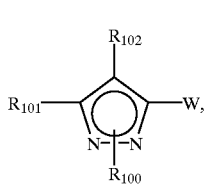

(I)

in which
$R_{100}$ is hydrogen, $C_1$–$C_6$alkyl, $C_3$–$C_8$cycloalkyl, $C_3$–$C_8$cycloalkyl-$C_1$–$C_8$alkyl, $C_3$–$C_6$alkenyl, $C_4$–$C_8$cycloalkenyl, $C_4$–$C_8$cycloalkenyl-$C_1$–$C_6$alkyl, $C_3$–$C_6$alkynyl, phenyl, phenyl-$C_1$–$C_6$alkyl or cyano, where the groups listed for $R_{100}$, with the exception of hydrogen and cyano, can be substituted by halogen, $C_1$–$C_6$alkyl, $C_1$–$C6$halogenoalkyl, cyano, or nitro;
$R_{101}$ is cyano;
$R_{102}$ is halogen;
W is a group $W_1$

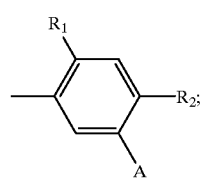

($W_1$)

in which
$R_1$ is hydrogen or halogen;
$R_2$ is halogen or cyano;
A is —$X_4R_4$,
in which
$X_4$ is oxygen or sulfur;
$R_4$ is hydrogen, $C_1$–$C_{10}$alkyl, $C_1$–$C_4$alkoxy-$C_1$–$C_4$alkyl, $C_1$–$C_4$alkylthio-$C_1$–$C_4$alkyl, di-$C_1$–$C_4$alkylamino-$C_1$–$C_4$alkyl, $C_1$–$C_8$halogenoalkyl, $C_2$–$C_8$alkenyl, $C_2$–$C_8$halogenoalkenyl, $C_3$–$C_8$alkynyl, $C_3$–$C_7$cycloalkyl, oxetan-3-yl, halogeno-$C_3$–$C_7$-cycloalkyl, $C_1$–$C_8$alkylcarbonyl, $C_1$–$C_8$alkoxycarbonyl, allylcarbonyl, —$SO_2CF_3$, —$SO_2C_6H_5$, $C_3$–$C_7$cycloalkylcarbonyl, benzoyl, which is unsubstituted or substituted on the phenyl ring up to three times in an identical or different manner by halogen, $C_1$–$C_4$alkyl, $C_1$–$C_4$halogenoalkyl, $C_1$–$C_4$halogenoalkoxy or $C_1$–$C_4$alkoxy; $C_1$–$C_8$alkyl substituted by cyano, nitro, carboxyl, $C_1$–$C_8$alkylthio-$C_1$–$C_8$alkoxycarbonyl, phenyl, halogenophenyl, $C_1$–$C_4$alkylphenyl, $C_1$–$C_4$alkoxyphenyl, $C_1$–$C_4$halogenoalkylphenyl, $C_1$–$C_4$halogenoalkoxyphenyl, $C_1$–$C_6$alkoxycarbonyl, $C_1$–$C_4$alkoxy-$C_1$–$C_4$alkoxyl, $C_1$–$C_4$alkoxy-$C_1$–$C_8$alkoxycarbonyl, $C_3$–$C_8$alkenyloxycarbonyl, $C_3$–$C_8$alkynyloxycarbonyl, $C_1$–$C_8$alkylthiocarbonyl, $C_3$–$C_8$alkenylthiocarbonyl, $C_3$–$C_8$alkinylthiocarbonyl, carbamoyl, $C_1$–$C_4$alkylaminocarbonyl, di-$C_1$–$C_4$alkylaminocarbonyl, $C_3$–$C_8$alkenylaminocarbonyl, di-$C_3$–$C_8$-alkenylaminocarbonyl, $C_1$–$C_4$alkyl-$C_3$–$C_8$alkenylaminocarbonyl, phenyloxycarbonyl or phenyl-$C_1$–$C_8$alkyloxycarbonyl, which is unsubstituted or substituted on the phenyl up to three times in an identical or different manner by halogen, $C_1$–$C_4$alkyl, cyano, nitro or amino; phenylaminocarbonyl, which is unsubstituted or substituted on the phenyl up to three times in an identical or different manner by halogen, $C_1$–$C_4$alkyl, $C_1$–$C_4$halogenoalkyl, $C_1$–$C_4$halogenoalkoxy or $C_1$–$C_4$alkoxy or once by cyano or nitro; dioxolan-2-yl, which is unsubstituted or substituted by one or two $C_1$–$C_4$alkyl radicals; or dioxanyl, which is unsubstituted or substituted by one or two $C_1$–$C_4$alkyl radicals;

or a pyrazole N-oxide, salt, or stereoisomer of a compound of the formula I.

2. A process for the preparation of a compound of the formula I

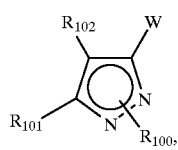
(I)

in which

W, $R_{100}$ and $R_{102}$ are as defined in claim 1 and $R_{101}$ is the radical —CN, which process comprises
a) dehydrating a compound of the formula XXIIa or XXIIb

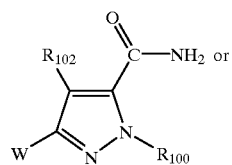
(XXIIa)

(XXIIb)

in which W, $R_{100}$ and $R_{102}$ are as defined; or
b) first diazotizing a compound of the formula XXIIIa or XXIIIb

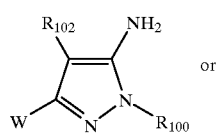
(XXIIIa)

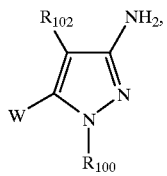
(XXIIIb)

in which W, $R_{100}$ and $R_{102}$ are as defined, and then reacting the diazonium salt formed with a salt of the formula XXXI $M^{\oplus}CN^{\ominus}$ (XXXI), in which $M^{\oplus}$ is an alkali metal, alkaline earth metal or transition metal ion; or
c) reacting a compound of the formula XXIVa or XXIVb

(XXIVa)

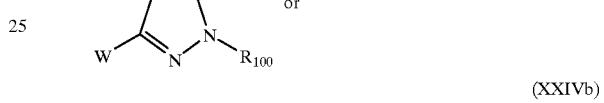
(XXIVb)

in which W, $R_{100}$ and $R_{102}$ are as defined, with hydroxylamine and dehydrating the oxime intermediately formed; or
d) reacting a compound of the formula XXVa or XXVb

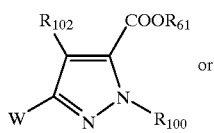
(XXVa)

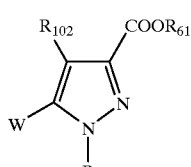
(XXVb)

in which W, $R_{100}$ and $R_{102}$ are as defined, $R_{61}$ is hydrogen, $C_1$–$C_{10}$alkyl, $C_1$–$C_4$alkoxy-$C_1$–$C_4$alkyl, $C_2$–$C_8$halogenoalkyl, $C_1$–$C_8$ alkylthio-$C_1$–$C_4$alkyl, di-$C_1$–$C_4$alkylamino-$C_1$–$C_4$alkyl, cyano-$C_1$–$C_8$alkyl, $C_3$–$C_8$alkenyl, $C_3$–$C_8$halogenoalkenyl, $C_3$–$C_8$alkynyl $C_3$–$C_7$cycloalkyl, oxetan-3-yl, $C_3$–$C_7$ cycloalkyl-$C_1$–$C_4$alkyl, halogeno-$C_3$–$C_7$cycloalkyl or benzyl which is unsubstituted or substituted on the phenyl ring up to three times in an identical or different manner by halogen, $C_1$–$C_4$alkyl, $C_1$–$C_4$halogenoalkyl, $C_1$–$C_4$halogenoalkoxy or $C_1$–$C_4$alkoxy; alkali metal, alkaline earth metal or ammonium ions; or $C_1$–$C_6$alkyl-$COOR_7$, in which $R_7$ is hydrogen, $C_1$—$C_6$alkyl, $C_3$–$C_8$alkenyl, $C_3$–$C_8$alkynyl, $C_1$–$C_8$alkoxy-$C_2$–$C_8$alkyl, $C_1$–$C_8$alkylthio-$C_1$–$C_8$alkyl or $C_3$–$C_7$cycloalkyl;
with dimethylaluminium amide in the presence of an inert organic solvent.

3. A compound according to claim 1, in which $R_{102}$ is hydrogen, halogen, $C_1$–$C_4$alkyl, $C_1$–$C_4$halogenoalkyl, cyano or $C_2$–$C_4$alkynyl.

4. A herbicidal composition which inhibits plant growth, which comprises one or more compounds of the formula I according to claim 1.

5. A composition according to claim 4, which comprises between 0.1% and 95% of active ingredient of the formula I.

6. A method of controlling undesirable plant growth, which comprises applying an active amount of an active ingredient of the formula I according to claim 1 or of a composition comprising this active ingredient to the plants or their environment.

7. A method according to claim 6, wherein an amount of active ingredient of between 0.001 and 2 kg per hectare is applied.

8. A method of inhibiting plant growth, which comprises applying an active amount of an active ingredient of the formula I according to claim 1 or of a composition comprising this active ingredient to the plants or their environment.

9. A compound according to claim 1, which has the formula

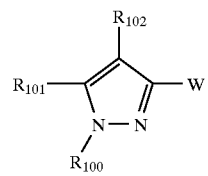

in which W, $R_{100}$, $R_{101}$, and $R_{102}$ are defined in claim 34.

* * * * *